(12) United States Patent
Noguchi et al.

(10) Patent No.: US 7,905,831 B2
(45) Date of Patent: Mar. 15, 2011

(54) ENDOSCOPE WASHING/DISINFECTING SYSTEM, ENDOSCOPE, AND ENDOSCOPE WASHING/DISINFECTING DEVICE

(75) Inventors: Toshiaki Noguchi, Tachikawa (JP); Eiri Suzuki, Sagamihara (JP); Masanori Gocho, Hachioji (JP); Hisashi Kuroshima, Hachioji (JP); Hitoshi Hasegawa, Yokohama (JP); Satoshi Itoya, Tachikawa (JP); Akio Ogawa, Tokyo (JP); Noriaki Ito, Hachioji (JP)

(73) Assignee: Olympus Corporation, Tokyo (JP)

( * ) Notice: Subject to any disclaimer, the term of this patent is extended or adjusted under 35 U.S.C. 154(b) by 1117 days.

(21) Appl. No.: 11/645,203

(22) Filed: Dec. 22, 2006

(65) Prior Publication Data
US 2007/0185385 A1    Aug. 9, 2007

Related U.S. Application Data

(63) Continuation of application No. PCT/JP2005/011541, filed on Jun. 23, 2005.

(30) Foreign Application Priority Data

Jun. 24, 2004 (JP) ................... 2004-186951
Jun. 24, 2004 (JP) ................... 2004-186955
Jun. 24, 2004 (JP) ................... 2004-186956

(51) Int. Cl.
  *A61B 1/04* (2006.01)
(52) U.S. Cl. ......... 600/132; 600/118; 600/133; 600/155; 600/157
(58) Field of Classification Search ............ 600/101, 600/133, 136, 153, 155, 157
See application file for complete search history.

(56) References Cited

U.S. PATENT DOCUMENTS

| | | | |
|---|---|---|---|
| 4,862,872 A | | 9/1989 | Yabe et al. |
| 5,573,494 A | * | 11/1996 | Yabe et al. ................ 600/121 |
| 5,723,090 A | * | 3/1998 | Beerstecher et al. .......... 422/26 |
| 6,814,932 B2 | * | 11/2004 | Hlebovy et al. ................ 422/28 |
| 6,860,516 B2 | * | 3/2005 | Ouchi et al. ................ 285/124.1 |
| 6,884,392 B2 | * | 4/2005 | Malkin et al. .................. 422/26 |
| 7,115,091 B2 | * | 10/2006 | Root et al. .................... 600/133 |
| 7,138,087 B1 | * | 11/2006 | Malkin et al. .................. 422/26 |
| 7,353,692 B2 | * | 4/2008 | Gocho .......................... 73/49.2 |
| 7,686,761 B2 | * | 3/2010 | Jackson et al. ............... 600/155 |
| 2004/0156744 A9 | * | 8/2004 | Stanley ......................... 422/28 |
| 2005/0209507 A1 | * | 9/2005 | Suzuki et al. ................ 600/133 |

FOREIGN PATENT DOCUMENTS

| | | |
|---|---|---|
| JP | 62-49823 | 3/1987 |
| JP | 63-260523 | 10/1988 |
| JP | 04-317623 | 11/1992 |
| JP | 09-164117 | 6/1997 |
| JP | 2001-299697 | 10/2001 |
| JP | 2002-238847 | 8/2002 |
| JP | 2002-263066 | 9/2002 |
| JP | 2003-088499 | 3/2003 |

* cited by examiner

*Primary Examiner* — Matthew J Kasztejna
(74) *Attorney, Agent, or Firm* — Scully, Scott, Murphy & Presser, P.C.

(57) ABSTRACT

In a washing/disinfecting tank of an endoscope washing/disinfecting device, an endoscope connection portion to be joined to a connector portion of an endoscope body is provided, and receiving-side bases to be connected to each of pipelines of the endoscope body are provided. In washing/disinfecting the endoscope body, the connector portion is opposed to the endoscope connection portion in the predetermined positioned state, and then, a switch is turned on. Then, an electromagnet disposed at the endoscope connection portion is excited so as to attract and fix the connector portion by a generated magnetic force.

5 Claims, 37 Drawing Sheets

FIG.35

ENDOSCOPE WASHING/DISINFECTING SYSTEM, ENDOSCOPE, AND ENDOSCOPE WASHING/DISINFECTING DEVICE

CROSS REFERENCE TO RELATED APPLICATION

This application is a continuation application of PCT/JP2005/011541 filed on Jun. 23, 2005 and claims the benefit of Japanese Applications No. 2004-186951 filed in Japan on Jun. 24, 2004, No. 2004-186955 filed in Japan on Jun. 24, 2004, and No. 2004-186956 filed in Japan on Jun. 24, 2004, the entire contents of each of which are incorporated herein by their reference.

BACKGROUND OF THE INVENTION

1. Field of the Invention

The present invention relates to an endoscope washing/disinfecting system for automatically washing/disinfecting a used endoscope, an endoscope washed/disinfected by an endoscope washing/disinfecting device and an endoscope washing/disinfecting device.

2. Description of the Related Art

To an endoscope used for the purpose of inspection or treatment in a body cavity, filthy matters adhere not only to the outer surface of an insertion portion to be inserted into the body cavity but also each of endoscope pipelines such as an air/water supply pipeline, a suction pipeline or a forceps pipeline. Therefore, used endoscopes should be washed and disinfected.

In general, when an endoscope is to be given washing treatment and disinfection treatment using a washing/disinfecting device, as disclosed in Japanese Unexamined Patent Application Publication No. 2002-263066, first, a used endoscope is set in a washing/disinfecting tank and pipeline connection ports opened on the washing/disinfecting device side and the endoscope are connected through a washing tube.

Next, a treatment start switch is turned on. Then, first, a washing process is started and secondarily, a disinfection process is started.

In the washing process, first, washing water is supplied into the washing/disinfecting tank. After this washing water reaches a predetermined water level, washing is started. The washing water is circulated and the outer surface of the endoscope is washed by the water flow. Also, within each of the endoscope pipelines, the washing water in the washing/disinfecting tank is sucked by a circulating pump, and washing is carried out by pressure of water discharged from the circulating pump.

When the washing process is finished, the process moves on to a disinfecting process, but before that, the washing water is washed off as predetermined with tap water. When the process moves on to the disinfecting process, in place of the washing water supplied in the above-mentioned washing process, a disinfectant solution diluted to a predetermined concentration is supplied to the washing/disinfecting tank, and the disinfectant solution in the washing/disinfecting tank is sucked by the circulation pump and the disinfectant solution is supplied into the endoscope pipeline by pressure of water discharged from there. After the disinfectant solution is supplied into the endoscope pipeline, the endoscope is soaked in the disinfectant solution for a while for disinfection. After the disinfecting process is finished as predetermined, the disinfectant solution is washed off by tap water and then, the endoscope is dried and a series of the processes is finished.

SUMMARY OF THE INVENTION

In order to achieve the above objects, a first endoscope washing/disinfecting system is an endoscope washing/disinfecting system including an endoscope and an endoscope washing/disinfecting device, comprising a connector portion provided on the endoscope side and an endoscope connection portion fixed to a washing/disinfecting tank in the endoscope washing/disinfecting device, in which the endoscope and the endoscope connection portion are directly connected to each other in washing/disinfection of the endoscope.

A second endoscope washing/disinfecting system is an endoscope washing/disinfecting system including an endoscope and an endoscope washing/disinfecting device, comprising a connector portion which is provided on the endoscope side and can detachably connect the endoscope body and a universal cord and an endoscope connection portion fixed to a washing/disinfecting tank in the endoscope washing/disinfecting device, in which the universal cord is removed from the body of the endoscope and the body of the endoscope and the endoscope connection portion are directly connected to each other in washing/disinfection of the endoscope.

A third endoscope washing/disinfecting system comprises information transmission portion capable of bidirectional wireless communication and power transmission portion for transmitting power in the electrically non-contact manner both on the endoscope body and the washing/disinfecting device for washing/disinfecting the endoscope body.

A fourth endoscope washing/disinfecting system comprises an endoscope body provided with battery power supply portion for power supply and endoscope-side power transmission portion connected to the battery portion for transmitting power in the electrically non-contact manner, and an endoscope washing/disinfecting device for washing and disinfecting the endoscope body, and the endoscope washing/disinfecting device has device-side power transmission portion for transmitting power in the electrically non-contact state and when the device-side power transmission portion transmits power in the non-contact manner to the endoscope-side power transmission portion, power can be supplied and charged to the battery power supply portion.

A first endoscope is characterized in that characterized in that a connector portion is provided to an endoscope body having an insertion portion which can be inserted into a body cavity and an operation portion provided at the hand side of the insertion portion, connection portion being able to detachably connect a universal cord and being able to be directly and detachably connected to an endoscope connection portion fixed in a washing/disinfecting tank in an endoscope washing/disinfecting device.

A first endoscope washing/disinfecting device is characterized in that an endoscope connection portion which can directly and detachably connect a connector portion which can detachably connect a universal cord to an endoscope body having an insertion portion which can be inserted into a body cavity and an operation portion provided at the hand side of the insertion portion is fixedly provided in a washing/disinfecting tank.

A second endoscope washing/disinfecting device is an endoscope washing/disinfecting device for washing and disinfecting an endoscope set in a washing tank comprising a connection pipe into which at least a washing liquid is supplied, a movement mechanism for moving the connection pipe in a direction of a channel port of the endoscope set in the washing tank, and a first artificial muscle member, which is a seal member for sealing a space between the connection pipe and the channel port and can form a seal state and a non-seal state between the connection pipe and the channel port by applying a predetermined voltage.

BRIEF DESCRIPTION OF THE DRAWINGS

FIG. 35 is a view showing a state where the endoscope is set in a washing/disinfecting tank according to the sixth embodiment.

DETAILED DESCRIPTION OF THE PREFERRED EMBODIMENTS

First Embodiment

Figure 1:
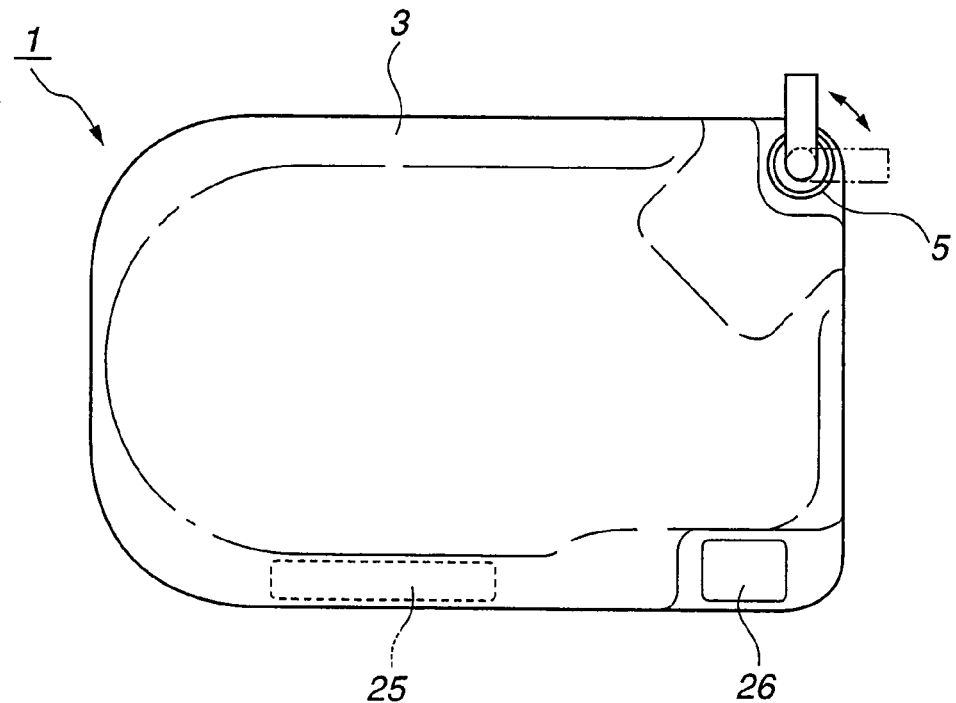
FIG. 1 is a plan view of an endoscope washing/disinfecting device according to a first embodiment.
Figure 2:
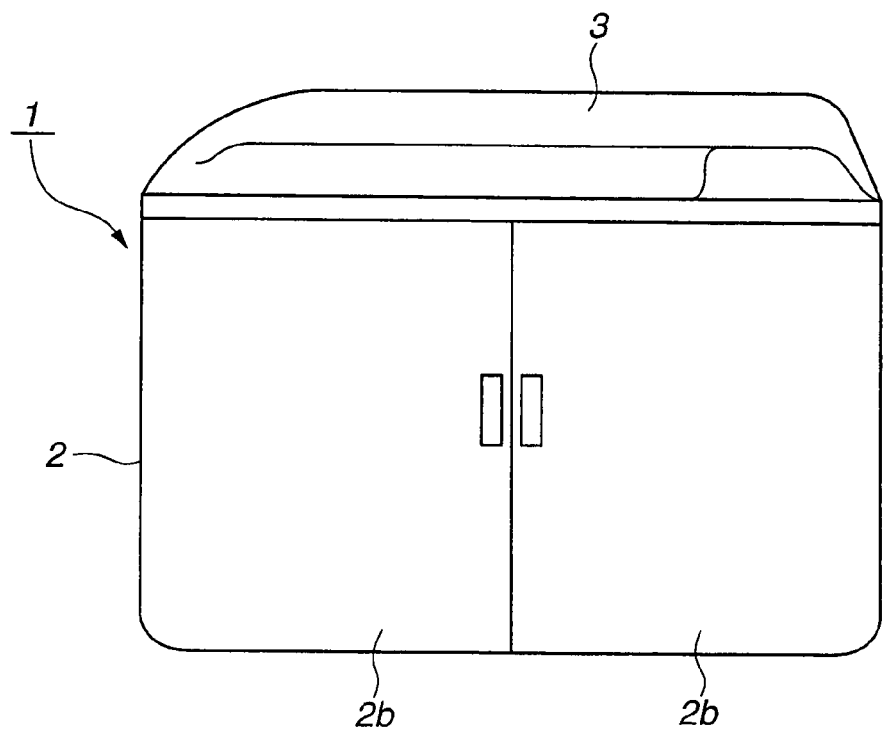
FIG. 2 is a front view of the endoscope washing/disinfecting device according to the first embodiment.
Figure 3:
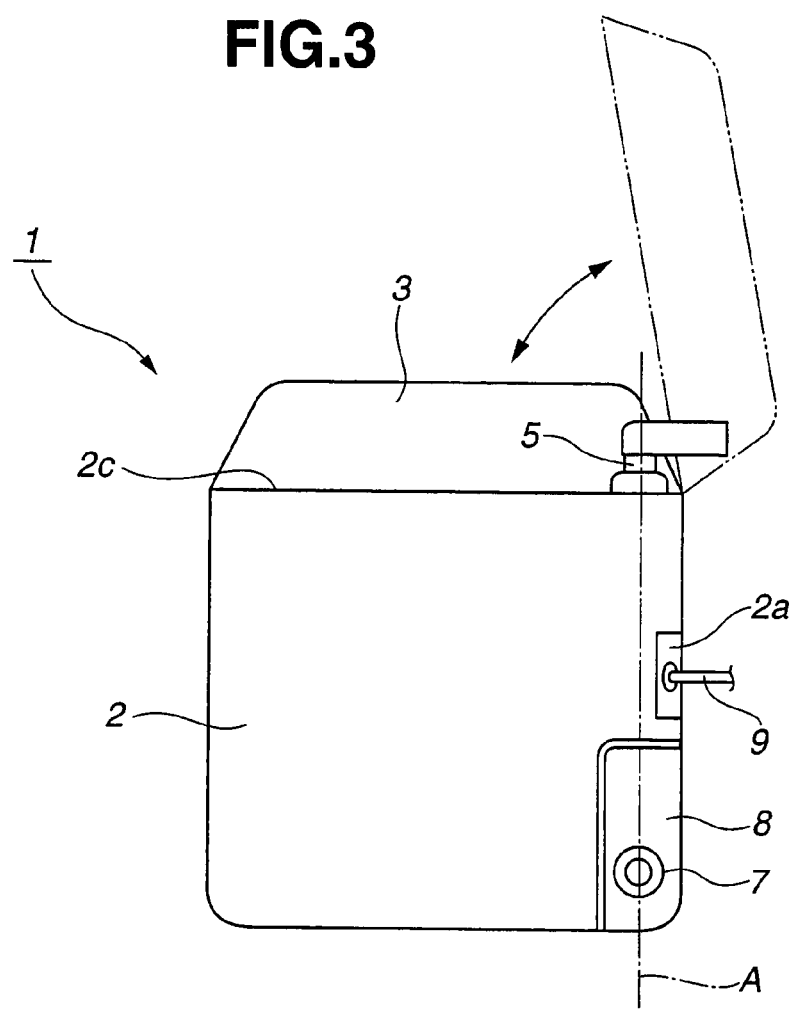
FIG. 3 is a right side view of FIG. 2 according to the first embodiment.

Embodiments of the present invention will be described below on the basis of the attached drawings. FIGS. 1 to 16 show a first embodiment of the present invention. In FIGS. 1 to 3, a plan view and a front view of an endoscope washing/disinfecting device and a right side view of FIG. 2 are shown.

An endoscope washing/disinfecting device 1 has a device body 2 and a top cover 3 for opening/closing its upper part, and a washing/disinfecting tank 4 is provided at an upper face (hereinafter referred to as "body upper face") 2c of the device body 2. This washing/disinfecting tank 4 is to wash/disinfect an endoscope body 101 by setting the body (hereinafter referred to as "endoscope body") 101 of an endoscope 100 (See FIG. 12) therein.

Figure 4:
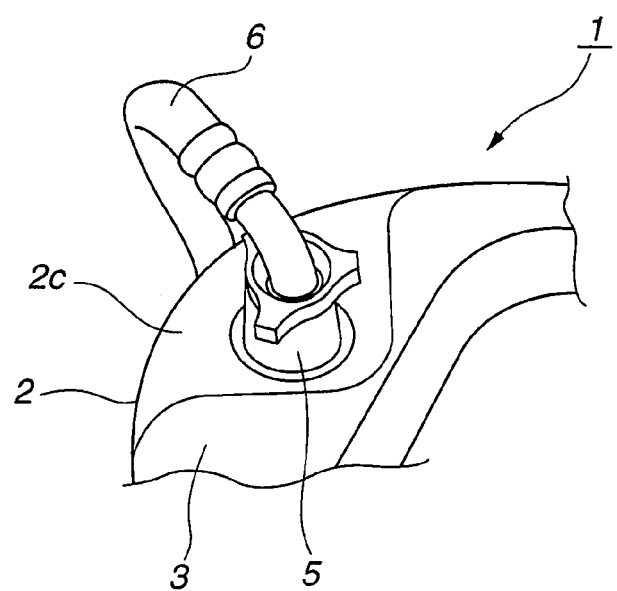
FIG. 4 is a perspective view of an essential part of FIG. 1 according to the first embodiment.

Also, at the corner on the back side of the body upper face 2c (right corner in the figure), a water feed connector 5 also functioning as a water feed valve is provided. As shown in FIGS. 1 and 4, a water feed connector 5 is rotatably supported with respect to the device body 2 and connected to a tap, not shown, through a water feed hose 6.

As shown in FIG. 3, a water discharge bracket 8 supporting a water discharge hose 7 is disposed at a lower part of the device body 2. The water discharge bracket 8 is rotatably supported around the same central axis A as that of the water feed connector 5, and an end of a water discharge passage (not shown) laid inside the device body 2 is connected to this rotation center so that this water discharge passage communicates with the water discharge hose 7 through the water discharge bracket 8. Also, in the middle of the side at the back corner of the device body 2 where the water feed connector 5 and the water discharge bracket 8 are disposed, a chamfered portion 2a is formed, and from this chamfered portion 2a, a power cord 9 connected to an external AC outlet 81 (See FIG. 5) is extended.

Figure 5:
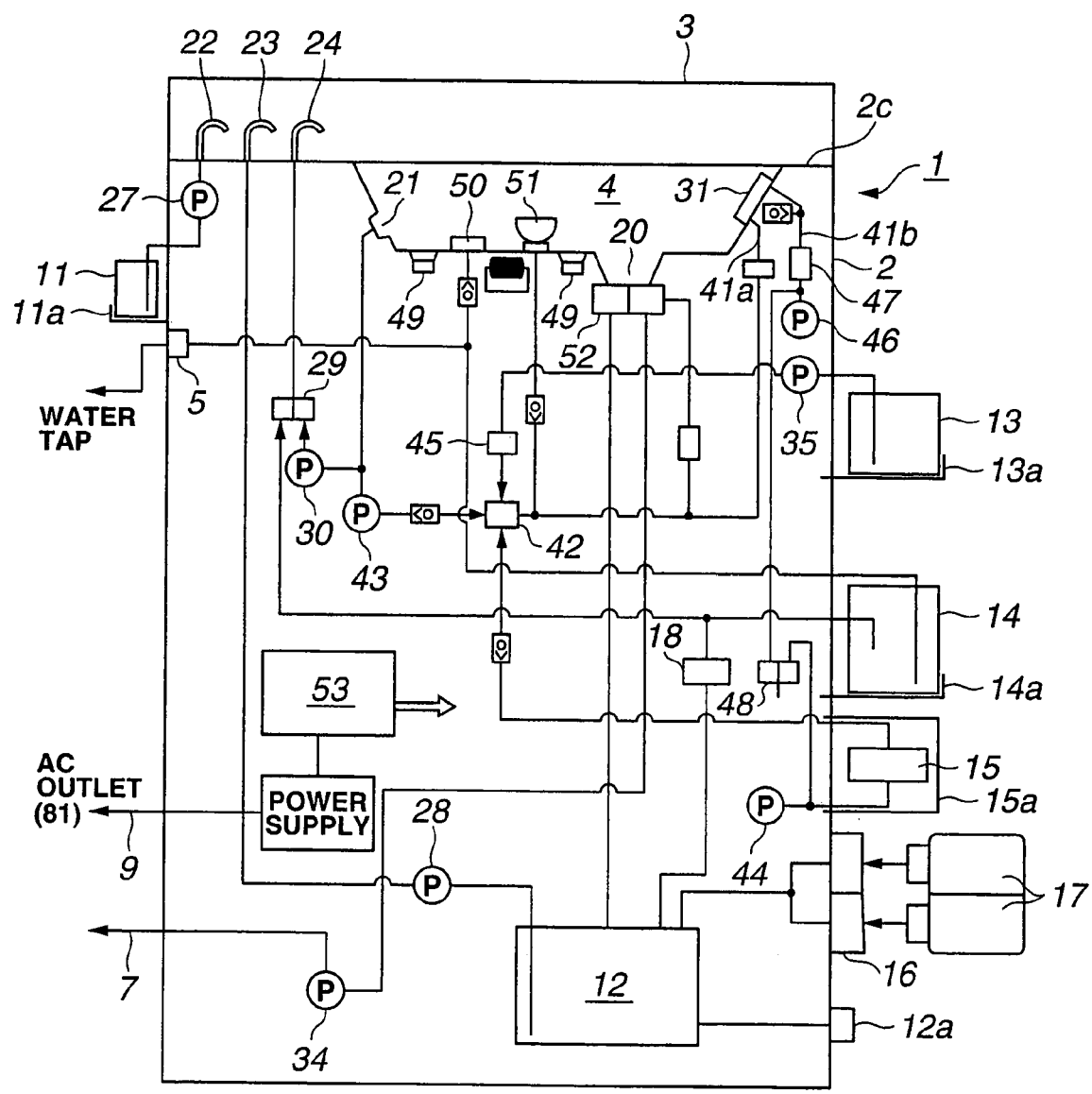
FIG. 5 is a schematic configuration diagram of the endoscope washing/disinfecting device according to the first embodiment.

As shown in FIG. 5, in the device body 2, a detergent tank 11 for reserving a liquid detergent, a disinfectant tank 12 for reserving a disinfectant diluted to a predetermined concentration, an alcohol tank 13 for reserving alcohol, a water filter 14 for filtering tap water supplied from the water tap, and an air filter 15 are disposed. The disinfectant tank 12 is fixed to the inside of the device body 2. Reference character 12a denotes a disinfectant drain port and it is usually closed.

The detergent tank 11, the alcohol tank 13, the water filter 14, and the air filter 15 are mounted on each of trays 11a, 13a to 15a. Each tray 11a, 13a to 15a are capable of being withdrawn forward by opening a front door 2b of the device body 2 so that the liquid can be replenished or parts can be replaced as predetermined.

In replenishment of the disinfectant in the disinfectant tank 12, the front door 2b of the device body 2 is opened, and a disinfectant bottle 17 filled with a disinfectant is connected to a bottle connector 16 fixed to the inside of the device. At that time, tap water filtered by the water filter 14 is supplied to the disinfectant tank 12 through a dilution valve 18. Therefore, a disinfectant diluted to a predetermined concentration is reserved in the disinfectant tank 12. FIG. 5 shows a state where each tray 11a, 13a to 15a has been withdrawn.

Figure 6:
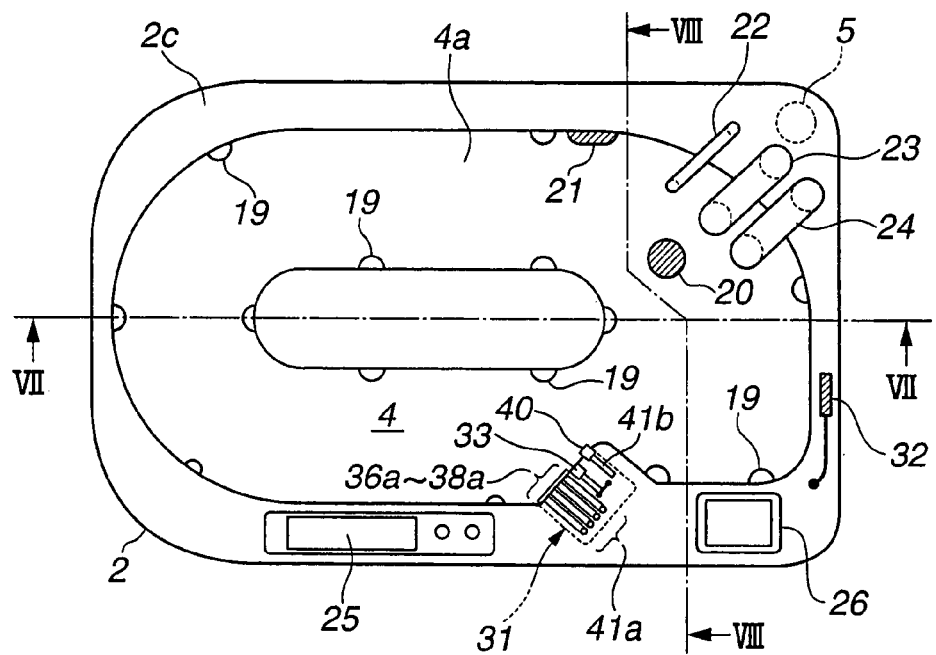
FIG. 6 is a plan view of a washing/disinfecting tank according to the first embodiment.
Figure 7:
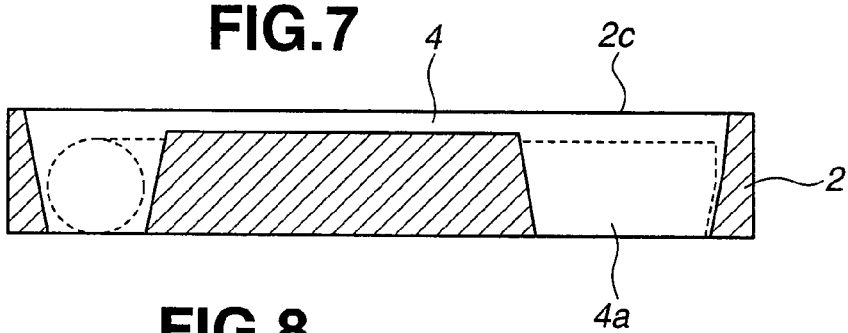
FIG. 7 is a VII-VII sectional outline view of FIG. 6 according to the first embodiment.
Figure 8:
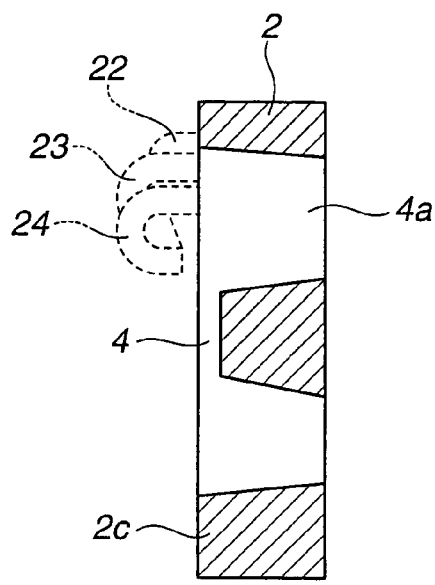
FIG. 8 is VIII-VIII sectional outline view of FIG. 6 according to the first embodiment.

FIG. 6 shows the body upper face 2c with the top cover 3 removed. The washing/disinfecting tank 4 disposed on the body upper face 2c has a storing recess portion 4a for storing the endoscope body 101 in a laterally long oval shape, and high-pressure nozzles 19 are disposed per predetermined interval on the outer circumferential wall surface and the inner circumferential wall surface of this storing recess portion 4a. Also, a drain port 20 is provided on the bottom surface of the storing recess portion 4a. Moreover, a circulation port 21 is provided on one side on the outer circumferential wall surface of the storing recess portion 4a.

At the corner on the side where the water feed connector 5 of the body upper face 2c is disposed, a detergent nozzle 22, a disinfectant nozzle 23, and a water-feed/circulation nozzle 24 are disposed. Moreover, on the front face side of the body upper face 2c, an operation panel 25 and a monitor 26 using a liquid crystal device or the like are disposed.

As shown in FIG. 5, the detergent nozzle 22 communicates to the detergent tank 11 through a detergent pump 27, and the disinfectant nozzle 23 communicates with the disinfectant tank 12 through a drug pump 28. Moreover, the water-feed/circulation nozzle 24 is capable of selective connection to the water filter 14 and a liquid pump 30 through a three-way switching valve 29.

In the state where the feed-water/circulation nozzle 24 is connected to the water filter 14 side through the tree-way switching valve 29, tap water filtered by the water filter 14 is discharged from the water-feed/circulation nozzle 24. On the other hand, in the state where the water-feed/circulation nozzle 24 is connected to the liquid pump 30 through the three-way switching valve 29, the washing water or the disinfectant reserved in the storing recess portion 4a taken in from the circulation port 21 is discharged and circulated. Though not shown, the high-pressure nozzle 19 is connected between the water-feed/circulation nozzle 24 and the three-way switching valve 29 through a high-pressure pump, and the liquid (tap water, washing water) is also injected from this high-pressure nozzle 19 at a high pressure similarly to the water-feed/circulation nozzle 24. A water flow is generated in the storing recess portion 4a by the liquid discharged from this high-pressure nozzle 19 and the water-feed/circulation nozzle 24 and by this water flow, the outer surface of the endoscope body 101 is washed in a washing process and the washing liquid or the disinfectant is washed off in a rinsing process.

Figure 12:
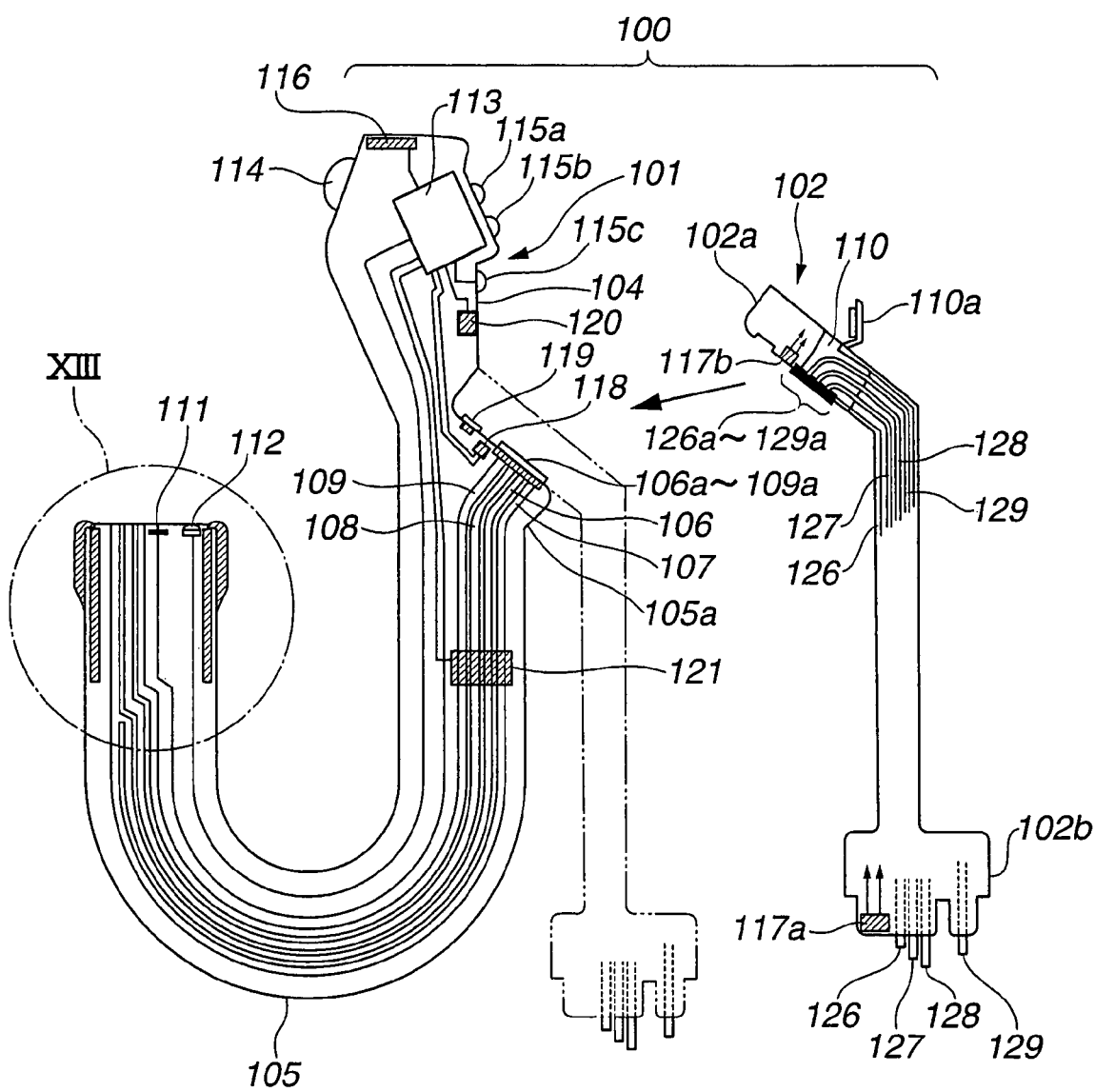
FIG. 12 is a schematic sectional view of the endoscope according to the first embodiment.
Figure 13:
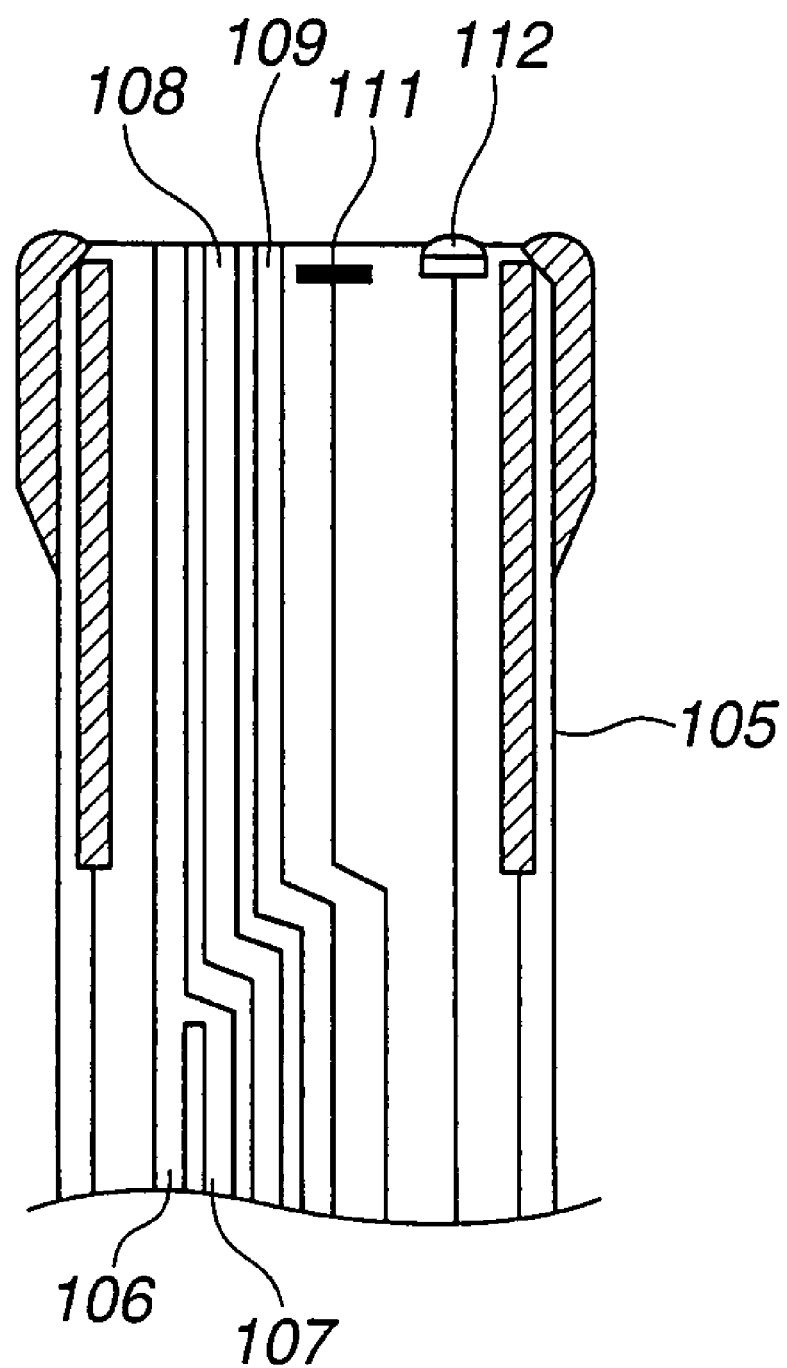
FIG. 13 is an enlarged view of XIII part of FIG. 12 according to the first embodiment.

Here, a construction of the endoscope 100 employed in this embodiment will be described referring to FIGS. 12 and 13.

As shown in the figures, the endoscope 100 is constructed by the endoscope body 101 and a universal cord 102, and both parts 101, 102 are separatable. The universal cord 102 is a disposable type and is discharged after each completion of an endoscopipc inspection. Therefore, a part requiring washing and disinfecting is only the endoscope body 101.

The endoscope body 101 comprises a hand-side operation portion 104 and an endoscope insertion portion 105 extending from this operation portion 104. Also, at the hand side of the endoscope insertion portion 105, a scope connector portion 105a on the body side is provided, and a cord-side connector portion 102a provided at the base end of the universal cord 102 is connected to this body-side scope connector portion 105a. Though not shown, the scope connector portion 105a and the cord-side connector portion 102a are mechanically fitted/fixed through a hook or the like.

At the endoscope insertion portion 105 of the endoscope body 101, an air supply pipeline 106, a water supply pipeline 107, a sub water supply pipeline 108, a suction pipeline 109 and the like representing the endoscope pipeline are disposed from the body-side scope connector portion 105a to the tip end side and opened on the tip end face (endoscope tip end face). The air supply pipeline 106 and the water supply pipeline 107 are collected at the middle of the tip end side and opened on the endoscope tip end face.

At the body-side scope connector portion 105a, pipeline bases 106a to 109a as connection ports communicating with the base ends of the pipelines 106 to 109 are provided.

To each of the pipeline bases 106a to 109a, bases 126a to 129a disposed at pipeline connector receiving portion 102a of the universal cord 102 are connected, respectively. To each of the bases 126a to 129a, the base end sides of pipelines 126 to 129 disposed in the universal cord 102 are connected. The tip end side of each of the pipelines 126 to 129 is opened at the scope connector portion 102b provided at the extended end side of the universal cord 102. At the pipeline connector receiving portion 102a, a forceps port 110 branched and connected to the pipeline 129 communicating with the suction pipeline 109 is opened, and the forceps port 110 is capable of being blocked by a forceps plug 110a.

The scope connector portion 102b provided at the universal cord 102 is connected to an endoscope control unit, not shown. At the endoscope control unit, a power supply portion for supplying driving electricity to the endoscope 100, a switching valve for supplying air/water to the air supply pipeline 106 (106b), the water supply pipeline 107 (107b), a valve for supplying water to the sub water supply pipeline 108 (108b) and a valve for supplying a negative pressure to the suction pipeline 109 (109b) are provided.

On the other hand, on the tip end face of the endoscope 100, an image pickup device 111 as image-capturing portion made of a CCD and the like for capturing a subject and an illuminating device 112 as illuminating portion made of an LED and the like for illuminating the subject. The both devices 111, 112 are connected to an endoscope-side control circuit 113 provided at the operation portion 104.

The endoscope-side control circuit 113 is provided with a power supply circuit and supplies power for light emission to the illuminating device 112. Moreover, the endoscope-side control circuit 113 has an image processing portion as image processing portion for signal processing of an image signal captured by the image pickup device 111, an operation signal input portion and readable/writable non-volatile memory device or the like as memory portion for storing information such as scope individual information relating to the endoscope body 101 such as a model number, recognition information, various history information including repair and washing number of times and the like.

On the outer circumference of the operation portion 104, a track ball 114 for curved operation of the endoscope tip end portion and operation switches such as scope switches 115a to 115c for various operations represented by air supply/water supply are disposed, and an operation signal from each of these operation switches is inputted to the operation signal input portion provided at the endoscope-side control circuit 113.

The endoscope-side control circuit 113 sends in a wireless manner the image signal captured by the image pickup device 111 and a signal corresponding to the operation signal outputted from each of the operation switches to the endoscope control unit through a sending/receiving antenna 116 incorporated in the operation portion 104. In the endoscope control unit, on the basis of the signal sent from the endoscope-side control circuit 113, an endoscopic image is displayed on a monitor (not shown) and control operation such as air supply/water supply is carried out by operating valves communicating with each of the pipelines 106 (106b) to 109 (109b) corresponding to each operation signal.

Since the control operation such as air supply/water supply to each of the pipelines 106 (106b) to 109 (109b) is carried out by the valves provided at the endoscope control unit in this way, valves or a mechanism to operate them are not incorporated in each of the pipelines 106 to 109 disposed in the endoscope body 101 and moreover, since the universal cord 102 is separated from the endoscope body 101, each of the pipelines 106 to 109 is substantially straight piping.

Electric power to the power supply circuit provided at the endoscope-side control circuit 113 is supplied from a power supply portion (not shown) provided at the endoscope control unit through the universal cord 102. At the scope connector portion 102b of the universal cord 102, a secondary-side sending/receiving coil 117a is provided, and a primary-side sending/receiving coil (not shown) for electromagnetic induction/coupling with the secondary-side sending/receiving coil 117a is provided.

At the pipeline connector receiving portion 102a of the universal cord 102, a primary-side sending/receiving coil 117b to be connected to the secondary-side sending/receiving coil 117a is provided, and a secondary-side sending/receiving coil 118 to be electromagnetically induced/coupled to this primary-side sending/receiving coil 117b is provided at the body-side scope connector portion 105a of the endoscope body 101. Therefore, electric power is transmitted in the non-contact state from the endoscope control unit side to the power supply circuit.

Also, at the body-side scope connector portion 105a, a base 119 for water leakage detection as a connection port for water leakage detection is provided. This water-leakage detection base 119 communicates with inside of the endoscope body 101 and increases the internal pressure by feeding air from the water-leakage detection base 119 and checks if a small hole, crack or the like is opened on the outer surface of the endoscope body 101 from the degree of leakage. Also, a pressure sensor 120 is disposed as internal pressure detecting portion in the operation portion 104. The endoscope-side control circuit 113 checks if there is any water leakage in the endoscope body 101, that is, if leakage by a crack or the like is generated or not on the basis of the internal pressure of the endoscope body 101 detected by the pressure sensor 120.

Moreover, a pipeline sensor as state detecting portion is disposed at each of the pipelines 106 to 109. The pipeline sensor 121 is a collective name of sensors for detecting the state of each of the pipelines 106 to 109 such as a flow-rate sensor, pressure sensor, transparency sensor and the like for detecting the flow rate, pressure, transparency of a fluid flowing through each of the pipelines 106 to 109.

Figure 9:
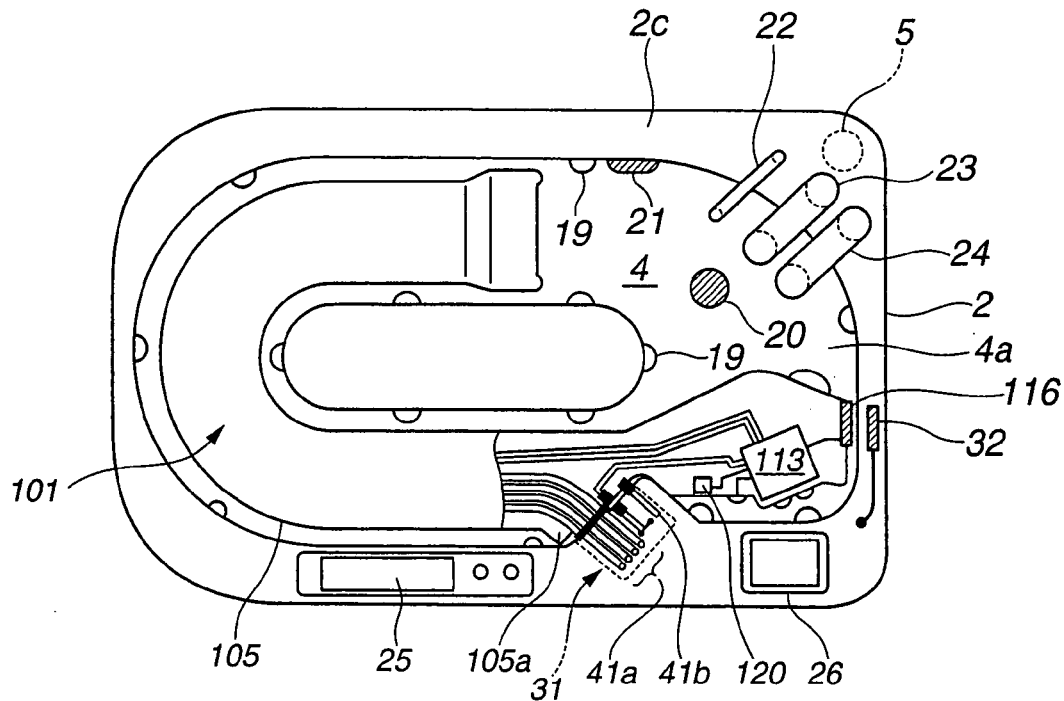
FIG. 9 is a plan view of the washing/disinfecting tank in the state where the endoscope body is set according to the first embodiment.

On the other hand, as shown in FIGS. 5 and 6, an endoscope connection portion 31 to be connected to the body-side scope connector portion 105a provided at the endoscope body 101 is disposed on one side of the washing/disinfecting tank 4 provided at the endoscope washing/disinfecting device 1, and moreover, as shown in FIGS. 6 and 9, a device-side sending/receiving antenna 32 for receiving a signal from the sending/receiving antenna 116 provided at the endo scope body 101 or for sending a signal to this sending/receiving antenna 116 is provided.

Figure 10:
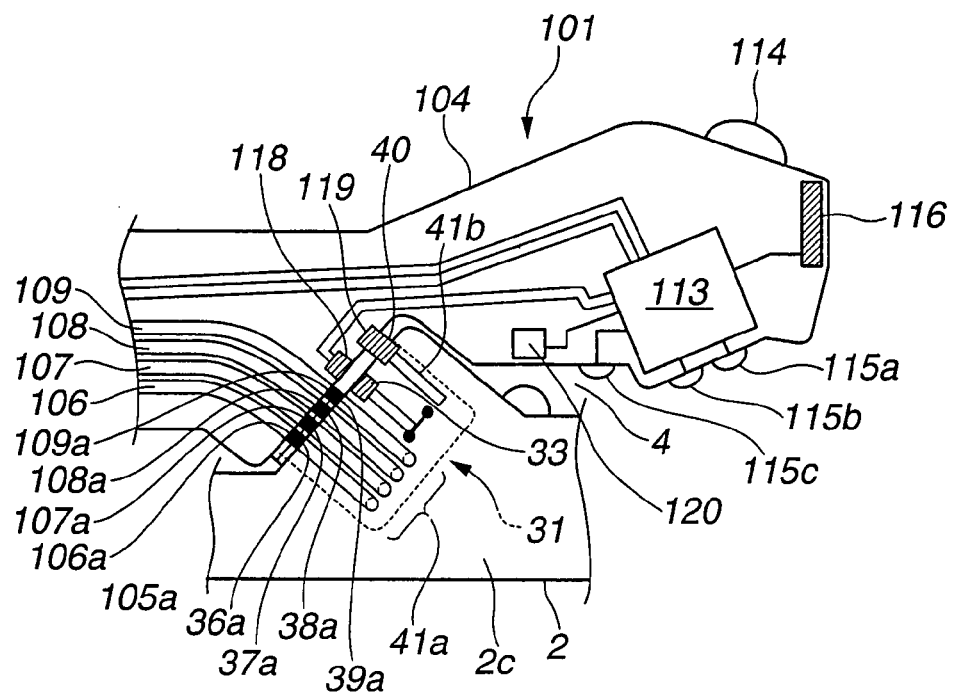
FIG. 10 is an enlarged view of an essential part of FIG. 9 according to the first embodiment.

The endoscope connection portion 31 has the similar construction as that of the pipeline connector receiving portion 102a provided at the above-mentioned universal cord 102 in principle. In detail, as shown in FIG. 10, receiving-side bases 36a to 39a, 40 as receiving-side connection ports are disposed on the tip end face of the endoscope connection portion 31, and a primary-side sending/receiving coil 33 for electromagnetic induction/coupling to the secondary-side sending/receiving coil 118 is provided at the body-side scope connector portion 105a of the endoscope body 101. Therefore, to the power circuit provided at the endoscope-side control circuit 113 of the endoscope body 101, electric power is transmitted in the non-contact state from the device body 2 side.

Each of the receiving-side bases 36a to 39a, 40 provided at the endoscope connection portion 31 is disposed at a position corresponding to each of the pipeline bases 106a to 109a and the water-leakage detection base 119 provided at the body-side scope connector portion 105a of the endoscope body 101. When the body-side scope connector portion 105a is connected to the endoscope connection portion 31, each of the receiving-side bases 36a to 39a, 119 on the body-side scope connector portion 105a side is connected to the receiving-side bases 36a to 39a, 40 of the endoscope connection portion 31. At this endoscope connection portion 31, an electromagnet unit 56 (See FIG. 11) as attaching/detaching portion is disposed, and in the state where bases 106a to 109a, 119 of the body-side scope connector portion 105a are connected to the receiving-side bases 36a to 39a, 40 of the endoscope connection portion 31 and positioned as appropriate, when a start switch (not shown) provided at the operation panel 25 of the device body 2 is turned ON, an electromagnet 56b of the electromagnetic unit 56 is excited, and the body-side scope connector portion 105a is attracted and fixed to the endoscope connection portion 31. In this embodiment, an electromagnet method is used as the detaching portion of the endoscope connection portion 31, but it may be attaching/detaching portion using air pressure or mechanical moving portion.

At each of the receiving-side bases 36a to 39a, a single washing/disinfecting tube 41a is branched/connected, and this washing/infecting tube 41a communicates with a discharge port of a channel block 42 made of a four-way valve. Also, with each inlet port branched into three of the channel block 42, the circulation port 21, the alcohol tank 13 and a compressor 44 are made to communicate. Also, between the circulation port 21 and the channel block 42, a channel pump 43 for sucking a fluid (tap water, washing water, disinfectant) from the circulation port 21 is interposed. Moreover, between the alcohol tank 13 and the channel block 42, an alcohol valve 45 for opening/closing a flow passage is interposed. Also, between the compressor 44 and the channel block 42, the air filter 15 is interposed.

By switching operation of the channel block 42 and making each inlet port selectively communicate with a discharge port, the liquid (tap water, washing water, disinfectant) reserved in the washing/disinfecting tank 4 or alcohol reserved in the alcohol tank 13 or air from the compressor 44 is supplied from each of the receiving-side bases 36a to 39a.

On the other hand, a water-leakage detection pump 46 is connected to the base 40 through a water-leakage detection tube 41b, and a block valve 47 is interposed in this water-leakage detection tube 41b. At detection of a small hole, a crack or the like on the outer surface of the endoscope body 101, first, the block valve 47 is opened and air from the water-leakage detection pump 46 is supplied into the endoscope body 101 through the water-leakage detection base 119 so as to increase the internal pressure to a predetermined. After that, the block valve 47 is closed so as to maintain the internal pressure in the endoscope body 101. And from the change in the internal pressure of the endoscope body 101 during that period, it is checked if a small hole, a crack or the like is opened or not on the outer surface of the endoscope body 101. The change in the internal pressure is detected by the pressure sensor 120 provided at the endoscope body 101. Reference numeral 48 denotes an exhaust valve, and by opening this, air from the water-leakage detection pump 46 and the compressor 44 can be made to escape to the outside.

Also, at the washing/disinfecting tank 4, an ultrasonic vibrator 49, a connector 50 for water feed pipeline disinfection, a washing case 51 and the like are disposed as appropriate, and moreover, a switching valve 52 is disposed at the discharge port 20. The ultrasonic vibrator 49 applies vibration to the washing water or tap water reserved in the washing/disinfecting tank 4 so as to apply ultrasonic washing or rinsing of the outer surface of the endoscope body 101. To the water-feed pipeline disinfection connector 50, a disinfectant nozzle 23 is connected through a hose or the like to supply the disinfectant to a water-feed pipe communicating with the water filter 14 and to disinfect this water-feed pipe. The washing case 51 accommodates detachable parts provided at the endoscope body 101 such as buttons of the scope switches 115a to 115c of the endoscope body 101 therein so that they can be washed/disinfected along with the endoscope body 101.

Moreover, a switching valve 52 disposed at the discharge port 20 is to switch a water discharge passage at discharge, and when tap water or washing water is reserved in the washing/disinfecting tank 4, the discharge port 20 is made to communicate with the discharge hose 7 side for discharge. On the other hand, if the disinfectant is reserved in the washing/disinfecting tank 4, the water discharge port 20 is made to communicate with the disinfectant tank 12 side and the disinfectant after disinfection is recovered in the disinfectant tank 12. Therefore, the disinfectant is used repeatedly.

Figure 11:
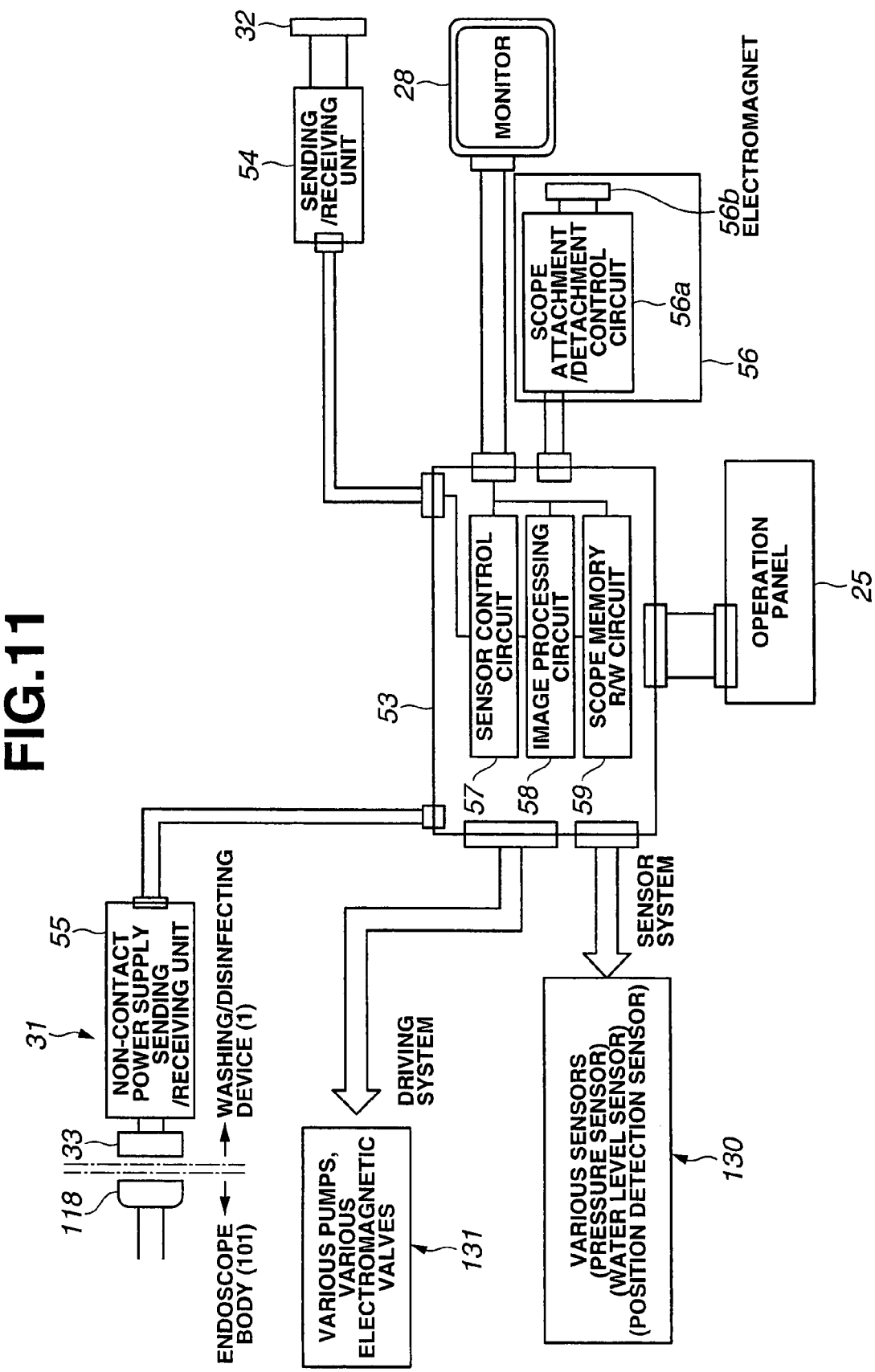
FIG. 11 is a schematic configuration diagram showing an internal circuit of the endoscope washing/disinfecting device according to the first embodiment.

The switching operation to each valve in the device is controlled by the device-side control circuit 53 incorporated in the device body 2. As shown in FIG. 11, to the input side of the device-side control circuit 53, a sensor system 130 including sensors, the sending/receiving unit 54 to be connected to the device-side sending/receiving antenna 32 and the like are connected. To the output side, a driving system 131 such as the non-contact power supply sending/receiving unit 55 for supplying power to the primary-side sending/receiving coil 33, the electromagnet unit 56, various pumps and valves, the monitor 26 displaying the endoscopic image and the like, the operation panel 25 and the like are connected. The electromagnet unit 56 is provided with the electromagnet 56b and a scope attachment/detachment control circuit 56a for exciting this electromagnet 56b.

Moreover, the device-side control circuit 53 is provided with a sensor control circuit 57, an image processing circuit 58, a scope memory R/W circuit 59. The sensor control circuit 57 receives and processes image information, sensor information, history information such as scope individual information such as a model number of the endoscope body 101, recognition information, repair history, washing number of times and the like received by the sending/receiving unit 54 and sent from the endoscope body 101.

The image processing circuit 58 executes signal processing of image information, outputs it as an image signal to the monitor 26 and displays the endoscopic image on the monitor 26. By checking the endoscopic image on the monitor 26 during washing and disinfecting, it can be confirmed that the image pickup device 111 is normally operating.

The scope memory R/W circuit 59 reads scope individual information of the endoscope body 101, displays the information on the monitor 26 and stores it in the memory device. Moreover, the scope memory RJW circuit 59 sends information such as time and date of this washing, disinfecting and the like to the endoscope body 101 side through the sending/receiving unit 54 and writes it in the memory device provided at the endoscope-side control circuit 113 of the endoscope body 101. On the monitor 26, information relating to washing, disinfecting such as washing remaining time, disinfecting remaining time and the like other than the endoscopic image and scope individual information are displayed. Also, on the operation panel 25, setting switches such as a mode selection switch are disposed other than the start switch.

Next, operation at washing and disinfecting of the used endoscope 100 using the endoscope washing/disinfecting device 1 constructed as above will be described.

As for the used endoscope 100 after an endoscopic inspection has been completed, first, the pipeline connector receiving portion 102a of the disposable type universal cord 102 is removed from the body-side scope connector portion 105a of the endoscope body 101 and discarded as predetermined. After that, the endoscope body 101 is given preliminary washing at bed side.

Next, full washing is executed using the endoscope washing/disinfecting device 1. At the full washing, first, the top cover 3 of the endoscope washing/disinfecting device 1 is opened and the endoscope body 101 is set at the washing/disinfecting tank 4 provided on the upper face of device body 2. At the bottom face of the storing recess portion 4a of the washing/disinfecting tank 4, a holding net (not shown) is extended.

When the endoscope body 101 is set at the washing/disinfecting tank 4, the body-side scope connector portion 105a of the endoscope body 101 is opposed to the endoscope connection portion 31 provided on the outer circumferential wall face of the washing/disinfecting tank 4. The endoscope connection portion 31 has the same construction as that of the pipeline connector receiving portion 102a of the universal cord 102 in principle and they can be connected to each other.

Figure 14:
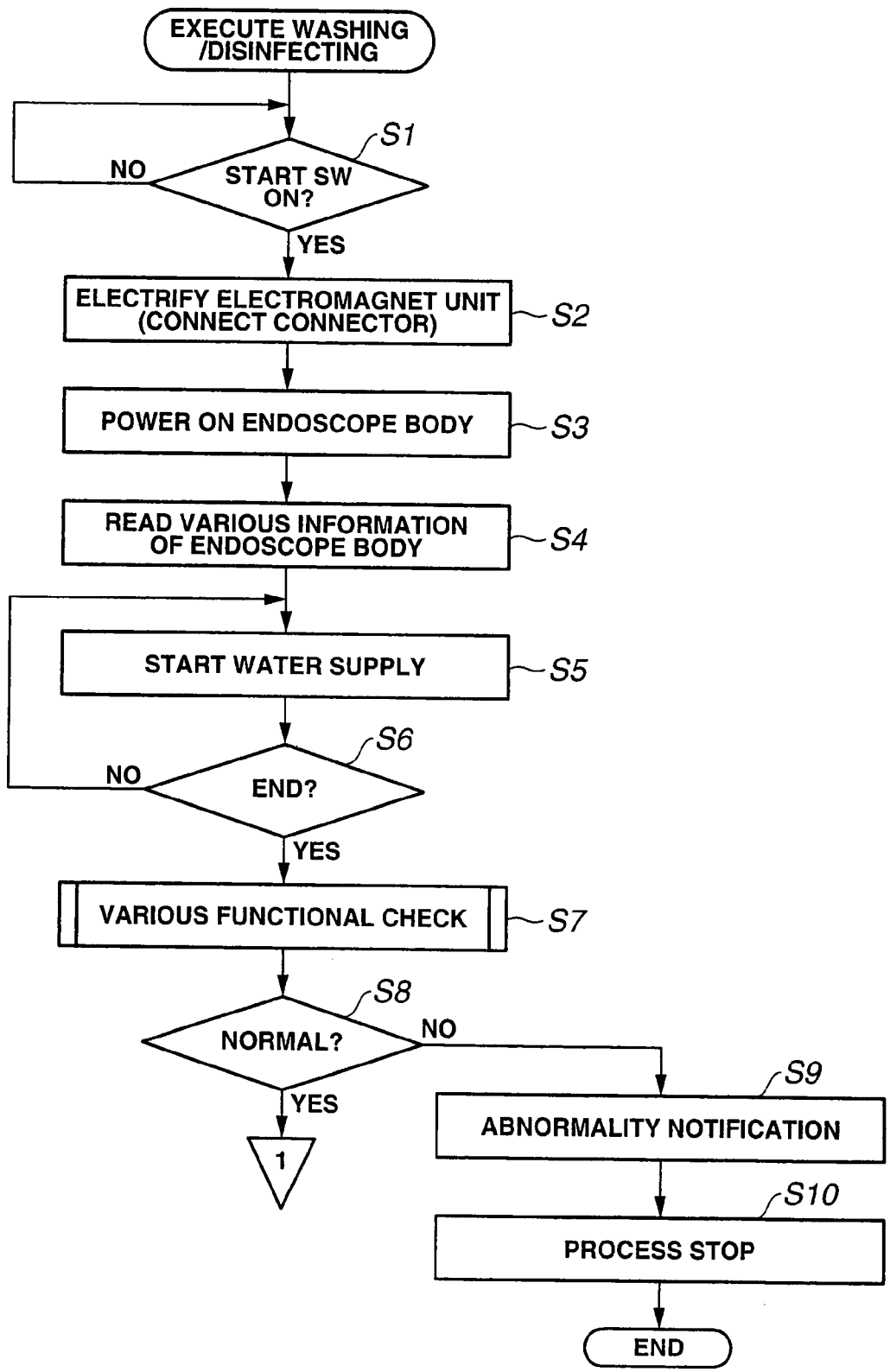
FIG. 14 is a flowchart showing a washing/disinfecting execution routine according to the first embodiment.
Figure 15:
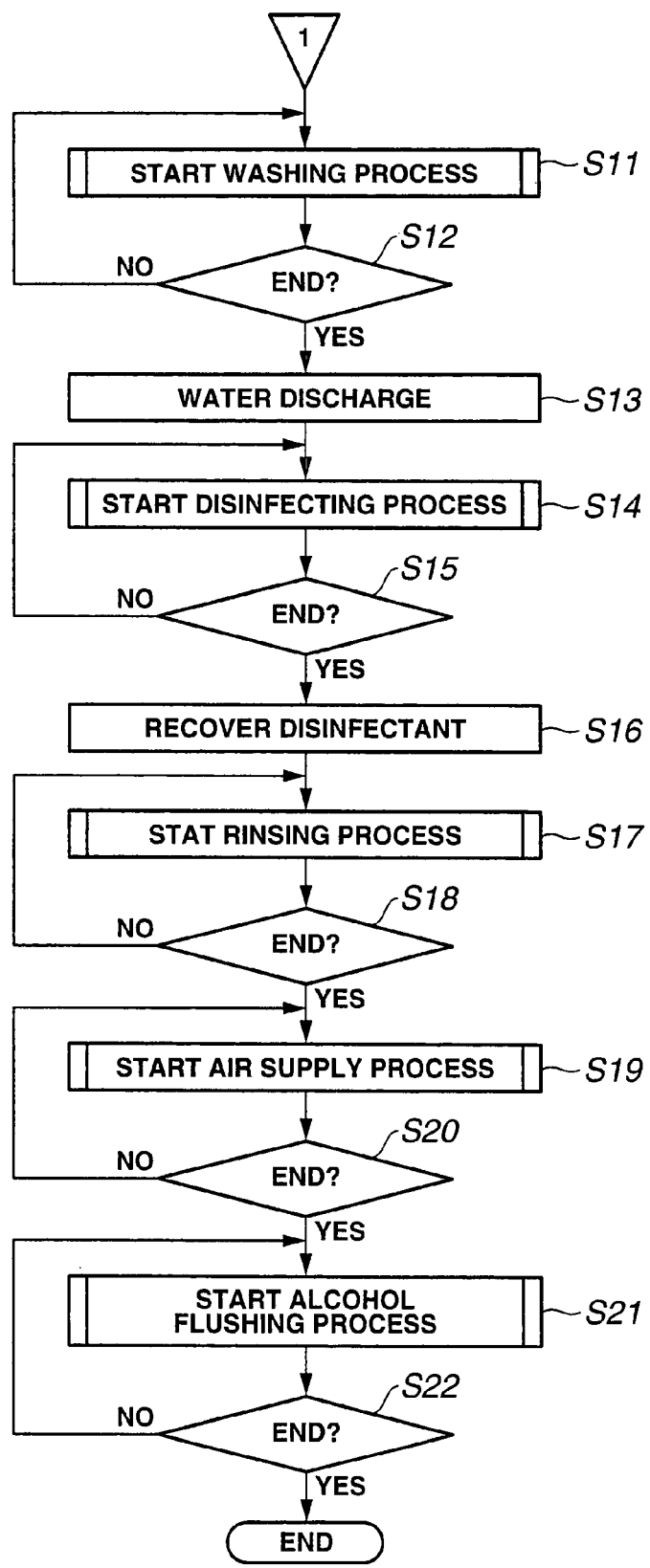
FIG. 15 is a flowchart (continued) showing a washing/disinfecting execution routine according to the first embodiment.

After the endoscope body 101 is set at the washing/disinfecting tank 4 as predetermined, the power switch is turned ON. Then, the device-side control circuit 53 incorporated in the device body 2 is powered on, and a washing/disinfecting execution routine shown in FIGS. 14, 15 is activated in the device-side control circuit 53.

In this routine, first, at Step S1, the start switch is brought into the state waiting for input, and when the start switch is turned ON, the routine goes on to Step S2.

At Step S2, an excitation signal is outputted to the electromagnet unit 56 provided at the endoscope connection portion 31. At the electromagnet unit 56, the scope attachment/detachment control circuit 56a excites the electromagnet 56b according to the excitation signal to have the body-side scope connector portion 105a of the endoscope body 101 attracted by a magnetic force generated at the electromagnet 56b and connects the body-side scope connector portion 105a to the endoscope connection portion 31. As a result, each of the pipeline bases 106a to 109a and the water leakage detection base 119 provided at the body-side scope connector portion 105a are automatically connected to the receiving-side bases 36a to 39a, 40 provided at the endoscope connection portion 31.

Therefore, when the endoscope body 101 is to be set at the washing/disinfecting tank 4 in this embodiment, there is no need to individually connect each of the pipelines 106 to 109 using a tube to the washing/disinfecting pipelines on the endoscope washing/disinfecting device 1 side through a tube or the like but time required for connection can be drastically reduced, connection error or defective connection is not caused but secure connection can be made.

After that, the routine goes on to Step S3, where an alternating voltage at a predetermined frequency is supplied to the primary-side sending/receiving coil 33 provided at the endoscope connection portion 31. As shown in FIG. 10, the primary-side sending/receiving coil 33 and the secondary-side sending/receiving coil 118 constituting the power transmitting portion using the electromagnetic induction coupling are disposed at the body-side scope connector portion 105a of the endoscope body 101 and the endoscope connection portion 31, respectively, and electric power is transmitted from the primary-side sending/receiving coil 33 to the secondary-side sending/receiving coil 118 in the non-contact state.

The power transmitted to the secondary-side sending/receiving coil 118 is rectified at the power supply circuit provided at the endoscope-side control circuit 113 as predetermined so as to generate a power voltage, and this power voltage starts the endoscope-side control circuit 113. Then, the endoscope-side control circuit 113 and the device-side control circuit 53 accommodated in the device body 2 become capable of mutual wireless communication through the sending/receiving antennas 116, 32.

Then, the routine goes on to Step S4, and the scope individual information such as the model number of the endoscope 100, the various history information such as repair history, washing number of times and the like stored in the memory device of the endoscope-side control circuit 113 is read out by wireless communication through the sending/receiving antennas 32, 116 and the information is stored by the scope memory R/W circuit 59 of the device-side control circuit 53 provided at the device body 2 in the memory device (not shown).

After that, the routine goes on to Step S5, and water feed is started. At starting the water feed, first, the three-way switching valve 29 is operated, and the water-feed/circulation nozzle 24 is connected to the water filter 14 side. Then, the tap water filtered by the water filter 14 is supplied form the water-feed/circulation nozzle 24 to the washing/disinfecting tank 4. At Step S6, the water level of the washing/disinfecting tank 4 is detected by a water level sensor or the like, not shown, and the end timing of the water feed is monitored. And when the water level reserved in the washing/disinfecting tank 4 reaches the set water level, the three-way switching valve 29 is operated again to shut off connection between the water-feed/circulation nozzle 24 and the water filter 14 side, the water feed is stopped, and the routine goes on to step S7.

At Step S7, various functional checks are carried out. Functional check items include basic items and model-specific items. The basic items are uniformly executed regardless of the model of the endoscope body 101 to be washed/disinfected, while the model-specific items are automatically set in correspondence to the endoscope 100 based on the read-out model number. The basic items include water leakage check, pipeline clogging check and the like.

For the water leakage check, first, the block valve 47 incorporated in the device body 2 is opened, and air from the water-leakage detection pump 46 is supplied into the endoscope body 101 from the water-leakage detection base 119 provided at the body-side scope connector portion 105a of the endoscope body 101 connected to this base 40 through the water-leakage detection tube 41b, the base 40 so as to pressurize inside the endoscope body 101. When a predetermined pressure is reached, the block valve 47 is closed, and pressure change inside the endoscope body 101 is measured. If the pressure change at this time is large, it is determined that a hole is opened on the outer surface of the endoscope body 101 and air is leaking. Alternately, if the pressure change is small, it is determined as normal. The internal pressure change is detected by the pressure sensor 120.

For the pipeline clogging check, first, the channel block 42 is operated and the circulation port 21 opened at the washing/disinfecting tank 4 is made to communicate with the washing/disinfecting tube 41a. Then, by driving the channel pump 43, the tap water reserved in the washing/disinfecting tank 4 is supplied to each of the pipelines 106 to 109 of the endoscope body 101 through the washing/disinfecting tube 41a for circulation. And the flow rate of the tap water flowing through each of the pipelines 106 to 109 is measured, the value and the reference value are compared and when the flow rate is less than the reference value, it is determined as the pipeline clogging. On the other hand, if the flow rate is at the reference value or above, it is determined as normal.

On the other hand, the model-specific items are different among models, and as in this embodiment, for example, an apparatus provided with the illuminating device 112 at the tip end of the endoscope as the illuminating portion outputs an illumination driving signal from the endoscope-side control circuit 113 to the illuminating device 112, the endoscopic image at that time is displayed on the monitor 26, and it is checked if the illuminating device 112 is lighted or not from the brightness. In this case, for automatic determination on whether the operation is normal or not, a light amount received by the image pickup device 111 is compared with the reference value, for example, and if the light amount is less than a set value, it is determined as abnormal, while if the value is at the set value or above, it is determined as normal.

In the endoscope 100 incorporating angle control portion for curved control of the tip end portion of the endoscope insertion portion 105 using a conductive polymeric artificial muscle (EPAM), which is expanded/contracted by application of a voltage, an angle control signal is outputted from the endoscope-side control circuit 113 to the EPAM, the endoscopic image at that time is displayed on the monitor 26, and it is checked if the operation is normal or not based on the fact that the endoscopic image is moving or not. In this case, too, for automatic determination, continuous movement of an image in a specific pixel area of the endoscopic image captured by the image pickup device 111 is detected, for example, this movement is compared with a driving signal outputted to the EPAM, and if they substantially correspond to each other, it is determined as normal, while if not, it is determined as abnormal.

Then, the routine goes on to Step S8, and if any one of the functional check results is determined as abnormal, the routine branches to Step S9, where the abnormality is notified by displaying that the endoscope body 101 is abnormal on the monitor 26 or the like and then, the routine goes on to Step S10, where the washing/disinfecting process is stopped and the routine is finished.

Portion for notifying abnormality can be anything such as display of the fact on the monitor 26, for example, sounding of a buzzer, or it may be a mimic voice from a speaker. Alternately, an abnormality display lamp may be provided on the operation panel and the lamp may be lighted.

On the other hand, if all the functional check items are determined as normal, the routine goes on to Step S11 and the washing process is started. Since the washing process and after are automatically operated, the top cover 3 is kept closed.

When the washing process is started, first, the liquid detergent reserved in the detergent tank 11 is discharged in an appropriate amount from the detergent nozzle 22 by driving of the detergent pump 27 and is mixed in tap water reserved in the washing/disinfecting tank 4 to generate washing water. In the washing process, the washing water reserved in the washing/disinfecting tank 4 is ejected from the high-pressure nozzle 19 provided on the outer circumferential wall surface and the inner circumferential wall surface of the recess portion 4a accommodating the endoscope body 101 to generate a water flow in the washing/disinfecting tank 4, and moreover, this water flow is vibrated by driving of the ultrasonic vibrator 49. As a result, the outer surface of the endoscope body 101 is washed by the water flow of the washing water and ultrasonic vibration.

Also, the three-way switching valve 29 and the channel block 42 are operated so that the circulation port 21 and the water-feed/circulation nozzle 24 and the washing/disinfecting tube 41a are made to communicate. As a result, by driving of the liquid pump 30 from the water-feed/circulation nozzle 24, the washing water is discharged and circulated. At the same time, the washing water is supplied by the discharge pressure of the channel pump 43 to each of the pipelines 106 to 109 of the endoscope body 101 via the washing/disinfecting tube 41a and each of the pipelines 106 to 109 is washed.

At each of the pipelines 106 to 109 of the endoscope body 101 employed in this embodiment, a valve or a mechanism for operating it is not incorporated, and moreover, since the universal cord 102 is separated, the pipelines 106 to 109 can be piped substantially in the straight state. As a result, each of the pipelines 106 to 109 has little channel resistance but can flow the washing water smoothly and wash inside of each of the pipelines 106 to 109 thoroughly.

After that, the routine goes on to Step S112, where it is determined if the washing process is finished or not based on the fact if the washing time has reached a set time or not, and the washing process is continued till the set time is reached. And when the set time is reached, it is determined that the washing is finished, and the routine goes on to Step S13, where the washing water is discharged. The discharge of the washing water is forced by operating the switching valve 52 provided at the discharge port 20 opened at the bottom portion of the washing/disinfecting tank 4 so as to make the discharge port 20 and the discharge hose 7 communicate with each other and by driving the discharge pump 34.

When the water discharge is finished as predetermined, the switching valve 52 is operated to block the discharge port 20, and moreover, the three-way switching valve 29 is operated to shut off the circulation port 21 and the water-feed/circulation nozzle 24, and the routine goes on to Step S14, where the disinfecting process is started.

When the disinfecting process is started, first, the disinfectant reserved in the disinfectant tank 12 is fed to the disinfectant nozzle 23 by driving the drug pump 28, and the disinfectant is supplied to the washing/disinfecting tank 4 from this disinfectant nozzle 23. In this state, since the circulation port 21 communicates with the washing/disinfecting tube 41a, the disinfectant reserved in the washing/disinfecting tank 4 is poured into each of the pipelines 106 to 109 of the endoscope body 101 by driving of the channel pump 43. And when the level of the disinfectant supplied to the washing/disinfecting tank 4 reaches the set level, the disinfectant is circulated for a set time.

After that, when the set time is reached, the driving of the channel pump 43 is stopped, the endoscope body 101 is soaked in the disinfectant for a set time. In this case, too, since each of the pipelines 106 to 109 of the endoscope body 101 of this embodiment is piped substantially in the straight state, the disinfectant can prevail through each of the pipelines 106 to 109 thoroughly.

Then, a soaking time of the endoscope body 101 is measured at Step S15, and when the soaking time reaches the set time, it is determined that disinfection is finished, and the routine goes on to Step S16. At Step S16, the disinfectant is recovered. Since the disinfectant is used repeatedly several times, the switching valve 52 is operated to make the discharge port 20 communicate with the disinfectant tank 12, and the disinfectant reserved in the washing/disinfecting tank 4 is recovered.

After the disinfectant is recovered in the disinfectant tank 12 as predetermined, the routine goes on to Step S17, and the rinsing process is started. When the rinsing process is started, first, the three-way switching valve 29 is driven, the water-feed/circulation nozzle 24 is made to communicate with the water filter 14 side, and the tap water filtered by the water filter 14 is supplied from the feed-water/circulation nozzle 24 to the washing/disinfecting tank 4. And after the set level is reached, the three-way switching valve 29 is closed, and as with the washing process, the tap water reserved in the washing/disinfecting tank 4 is circulated. And after the set time has elapsed, the water is discharged.

At Step S18, the number of rinsing times N is counted, and when the number of rinsing times N reaches the set number of times, it is determined that the rinsing is finished. And after the tap water used in the last rinsing process is discharged as predetermined, the routine goes on to Step S19, and an air supply process is started. When the air supply process is started, the channel block 42 is operated, the compressor 44 is made to communicate with the washing/disinfecting tube 41a, air is supplied to each of the pipelines 106 to 109 of the endoscope body 101, and the water in each of the pipelines 106 to 109 is removed and dried.

At step S20, air supply time by the compressor 44 is measured, and when a set time is reached, it is determined that the air supply process is finished, and after the compressor 44 is stopped, the routine goes on to Step S21.

At Step S21, an alcohol flushing process is started. In the alcohol flushing process, first, the channel block 42 is driven, the alcohol tank 13 is made to communicate with the washing/disinfecting tube 41a, and only a small amount of alcohol reserved in the alcohol tank 13 is fed to each of the pipelines 106 to 109 of the endoscope body 101 by driving of the alcohol pump 35. Then, the channel block, 42 is driven again, the washing/disinfecting tube 41a is made to communicate with the compressor 44 this time, and air is supplied to each of the pipelines 106 to 109 of the endoscope body 101 by driving of the compressor 44.

And alcohol is supplied together with the air to each of the pipelines 106 to 109 of the endoscope body 101 to accelerate evaporation of slight moisture remaining in each of the pipelines 106 to 109 by the alcohol and dry them early.

At Step S22, the air supply time is measured, and when the set time is reached, it is determined that the alcohol flushing process is finished, and the routine is finished.

In this way, in this embodiment, when washing/disinfecting the used endoscope body 101, the body-side scope connector portion 105a formed in the endoscope body 101 is attached by one touch to the endoscope connection portion 31 of the device body 2, the connection can be completed. Thus, complicated connection work is not needed any more, and work efficiency can be improved. Also, by improving the work efficiency, time required for washing/disinfection is reduced, and operating efficiency of the endoscope 100 can be improved by that amount.

Moreover, since the endoscope body 101 and the device body 2 are all in the non-contact manner except the portions where each of the pipelines 106 to 109 and the water-leakage detection base 119 are joined, liquid such as the washing water, the disinfectant and the like does not intrude into the endoscope body 101 during washing/disinfection, by which favorable waterproof can be obtained.

In various functional checks executed at Step S7 of the washing/disinfecting execution routine shown in FIG. 14, in addition to the basic items, model-specific items are also checked, but the model-specific items may be checked in the background in a series of processes from the washing process to the disinfecting process.

Figure 16:
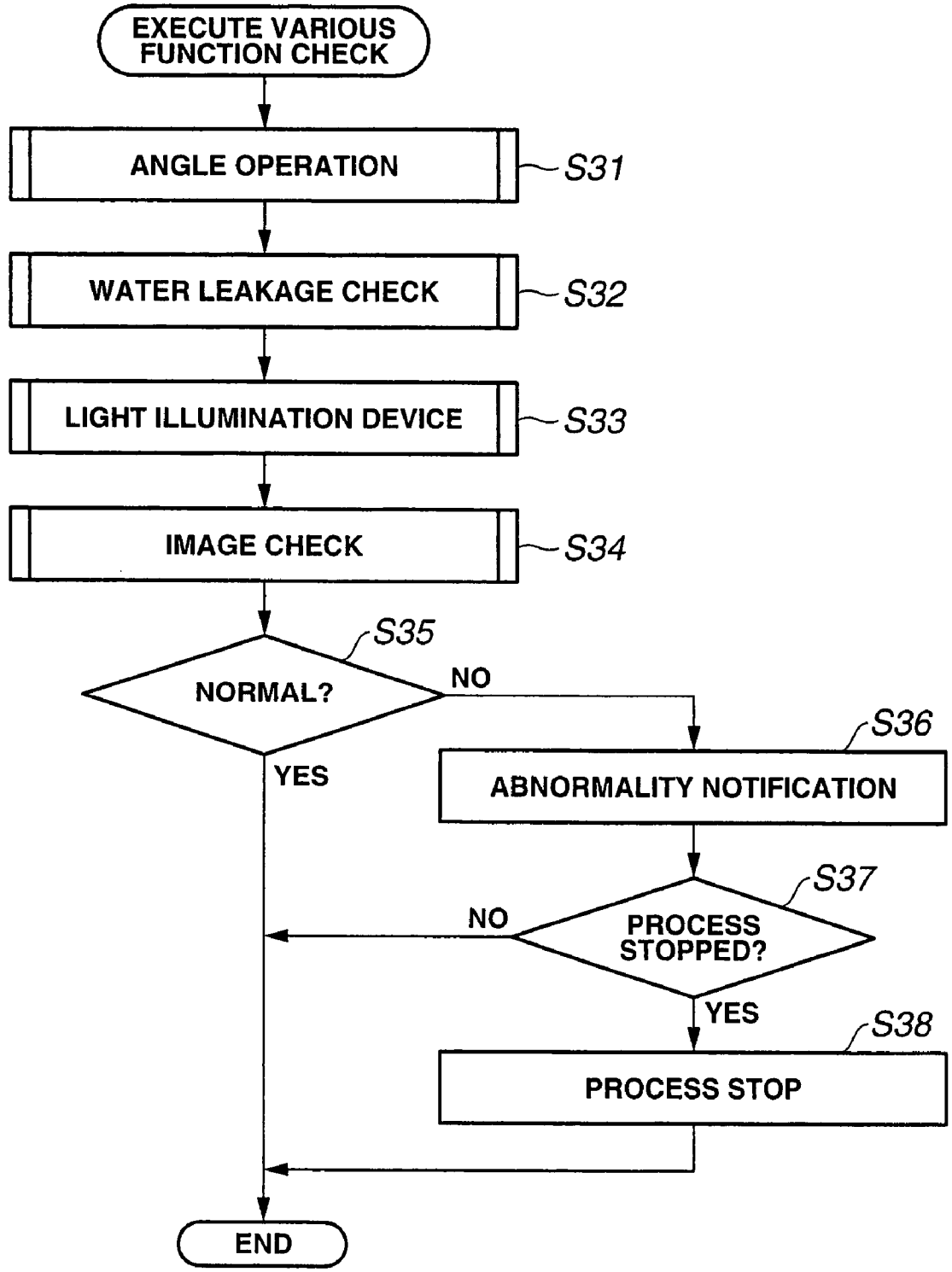
FIG. 16 is a flowchart showing various function check execution routine according to the first embodiment.

An example of the various functional check execution routine executed in the background is shown in FIG. 16.

In this routine, first, at Step S31, angle operation of the tip end portion operated by the EPAM is checked. As angle operation check, an angle operation signal is outputted from the endoscope-side control circuit 113 to the EPAM, and normal operation is checked by movement of the endoscopic image at that time.

At Step S32, the block valve 47 incorporated in the device body 2 is opened, and air from the water-leakage detection pump 46 is supplied into the endoscope body 101 from the water-leakage detection base 119 provided at the body-side scope connector portion 105a of the endoscope body 101 connected to the base 40 through the water-leakage detection tube 41b and the base 40, and the inside of the endoscope body 101 is pressurized to check the water leakage in the endoscope body 101.

At Step S33, a lighting signal is outputted from the endoscope-side control circuit 113 to the illuminating device 112, and it is checked if the illuminating device 112 is normal or not from the light amount of the endoscopic image at that time based on the fact that predetermined brightness has been obtained.

Also, at Step S34, based on the signal outputted from the image pickup device 111, it is checked if the image pickup device 111 is normally operating or not.

And at Step S35, if it is determined that all the operations are normal, the routine is finished there. On the other hand, if even one abnormality is detected, the routine branches to step S36, where abnormality is notified and then, the routine goes on to step S37, and input is awaited to determine if the current process should be stopped or not. If the process is not stopped, the routine is exited. On the other hand, if the process is to be stopped, the routine goes on to Step S38, where the current process is stopped and the routine is finished.

In this way, since the model-specific items are checked in the background of the process, time required for the washing/disinfecting can be further reduced, and operating efficiency of the endoscope 100 can be relatively improved.

Second Embodiment

Figure 17:
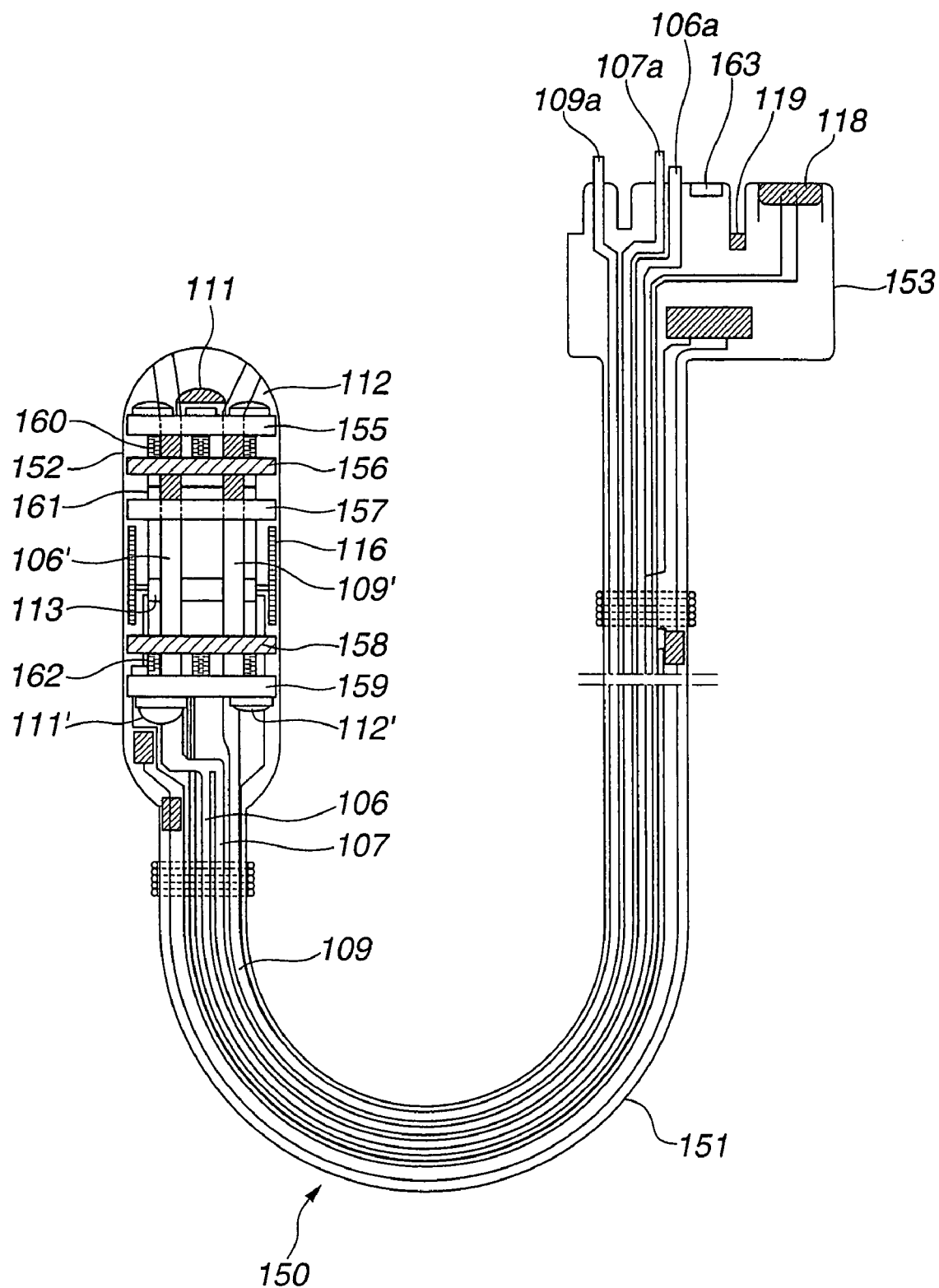
FIG. 17 is a schematic sectional view of a capsule type endoscope body according to a second embodiment.
Figure 18:
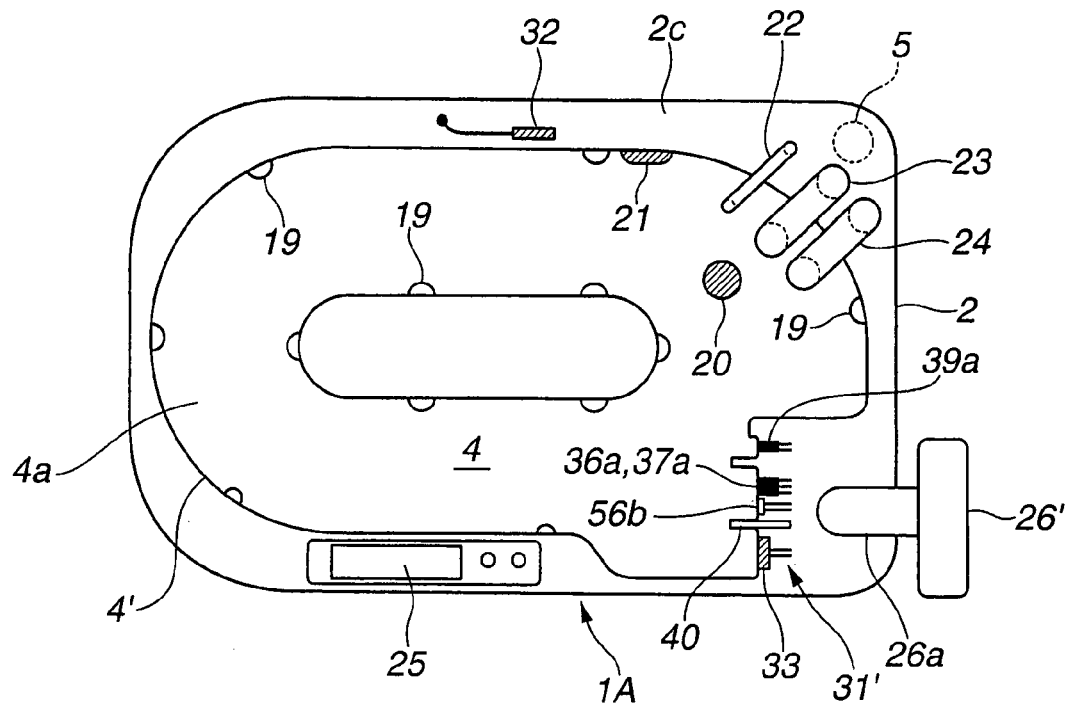
FIG. 18 is a plan view of a washing/disinfecting tank according to the second embodiment.
Figure 19:
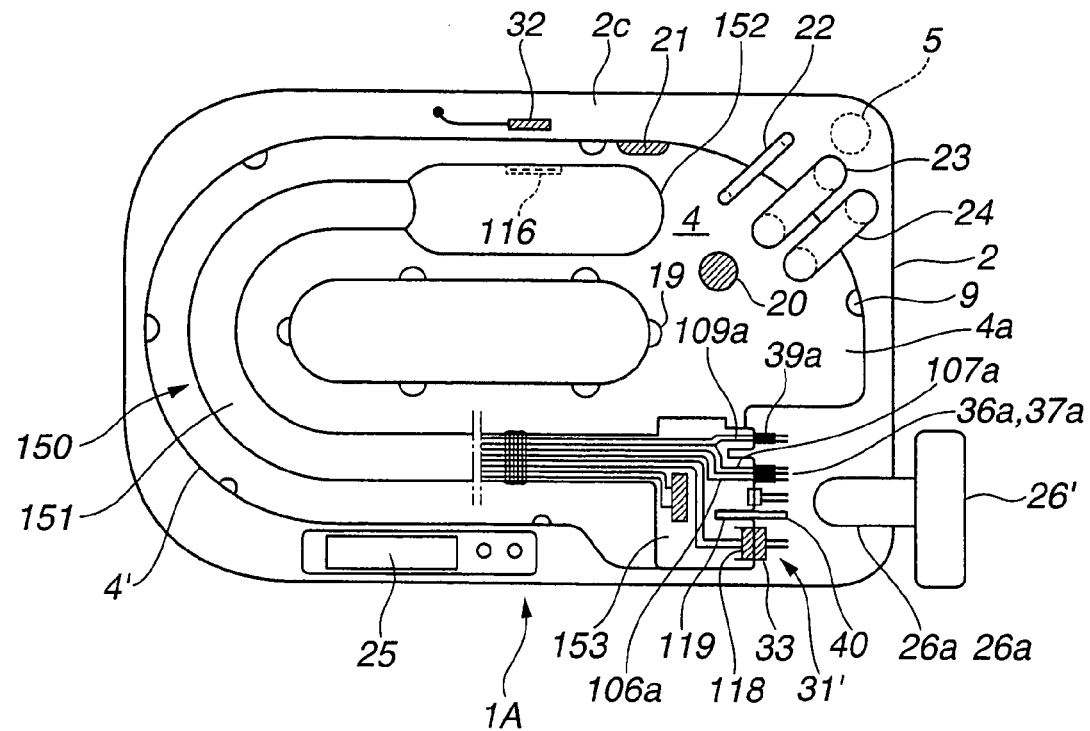
FIG. 19 is a plan view of the washing/disinfecting tank in the state where the capsule type endoscope device is set according to the second embodiment.

Next, a second embodiment of the present invention is shown in FIGS. 17 to 19. In this embodiment, an endoscope washing/disinfecting device 1A employed for washing/disinfecting a capsule-type endoscope body 150 will be described. The same components as those in the first embodiment are given the same reference numerals and the description will be omitted.

First, a construction of the capsule-type endoscope body 150 will be described using FIG. 17. The capsule-type endoscope body 150 comprises an elongated insertion portion 151 having flexibility and a capsule portion 152 in the capsule shape provided integrally at the tip end of this insertion portion 151, and at a rear end of this insertion portion 151, a scope connector portion 153 is provided. In an endoscopic inspection, this scope connector portion 153 is connected to an endoscope control unit or an air/water supply suction (AWS) unit (not shown).

In the insertion portion 151, the air supply pipeline 106, the water supply pipeline 107, the suction pipeline 109 and the like are disposed as predetermined, and in the capsule portion 152, an air supply pipeline 106', a suction pipeline 109' to which the air supply pipeline 106 and the water supply pipeline 107 are merged are disposed as predetermined. A forceps port is not connected to the middle of the suction pipeline 109. Forceps are automatically inserted from the endoscope control unit or the AWS unit into the suction pipeline 109.

Also, in the capsule portion 152, a first to a fifth base members 155 to 159 are disposed along the longitudinal direction. At the first base member 155 at the most tip end side, the image pickup device 111 is arranged, and the illuminating device 112 is disposed around it.

Moreover, a portion between the first base member 155 and the second base member 156 disposed behind it is connected capable of expansion/contraction through a viewing-direction variable member 160 made of the EPAM and the like. The first base member 155 is disposed capable of inclination and can incline the first base member 155 by the expansion/contraction operation of the viewing-direction variable member 160 and change the viewing-direction by inclining the tip end of the capsule portion 152 in an arbitrary direction.

A pivotal movement member 161 constructed by a motor and the like is disposed between the second and the third base members 156, 157, and by driving this pivotal movement member 161, the projecting direction of the forceps projecting forward from the suction pipeline 109' can be variably controlled.

At the fifth base member 159 disposed at the rearmost end side, an image pickup device 111' for capturing the rear and an illuminating device 112' are disposed. Moreover, a portion between this fifth base member 159 and the fourth base member 158 before that is connected capable of expansion/contraction through another viewing-direction variable member 162 made of the EPAM and the like, and similarly to the above-mentioned viewing-direction variable member 160, it inclines the fifth base member 159 by its expansion/contraction operation and can change the rearward viewing direction.

Moreover, in the capsule portion 152, the endoscope-side control circuit 113 provided with a power supply circuit is accommodated, and the sending/receiving antenna 116 for sending information such as an image signal captured by the image pickup devices 111, 111' processed by the endoscope-side control circuit 113 or receiving information inputted from outside is incorporated. At the endoscope-side control circuit 113, a memory device is provided. In this memory device, scope individual information such as a model number, recognition information and various history information such as repair, and washing number of times are stored.

On the other hand, at the scope connector portion 153, the pipeline bases 106a, 107a, 109a communicating with each of the pipelines 106, 107, 109, respectively, are provided. Moreover, the secondary-side sending/receiving coil 118 connected to the power supply circuit provided at the endoscope-side control circuit 113, the water-leakage detection base 119 communicating with the inside of the capsule type endoscope body 150, a magnetic body 163 attracted by a magnetic force generated at the electromagnet unit 56 provided at the endoscope washing/disinfecting device 1A, which will be described later and the like are disposed as predetermined. At the endoscope control unit to which the scope connector portion 153 is connected or the AWS unit and the endoscope washing/disinfecting device 1A, the primary-side sending/receiving coil (33) for electromagnetic induction/coupling to the secondary-side sending/receiving coil 118 is provided.

Next, the construction of the endoscope washing/disinfecting device 1A that washes/disinfects the capsule type endoscope body 150 will be described.

The construction of the endoscope washing/disinfecting device 1A is substantially the same as that of the endoscope washing/disinfecting device 1 according to the above-mentioned first embodiment but is only different in an endoscope connection portion 31' to which the scope connector portion 153 is connected and a monitor 26'.

As shown in FIGS. 18 and 19, the monitor 26' is provided at a monitor arm 26a extending from the upper face of the device body 2. The monitor arm 26a is made rotatable in the horizontal direction, and the monitor 26' is supported by the monitor arm 26a capable of inclination. Therefore, if the endoscope washing/disinfecting device 1A is installed in the longitudinal direction, for example, that is, if it is installed with the left side face close to the wall face and the right side face as the front face in FIG. 18, the monitor 26' can be oriented to the right face side direction. In this case, by constituting the monitor 26' as the touch panel, various setting by the operation panel 25 can be made on the monitor 26' side, which improves operability.

Also, the endoscope connection portion 31' provided on the outer circumferential wall face of a washing/disinfecting tank 4' basically has the same construction as that of the endoscope connection portion provided at the endoscope control unit or the AWS unit. That is, the receiving-side bases 36a, 37a, 39a, 40 are provided that are joined to each of the pipeline bases 106a, 107a, 109a provided at the scope connector portion 153 and the water-leakage detection base 119, and an electromagnet 56b provided at the electromagnet unit 56 (See FIG. 11) is disposed at a portion opposed to the magnetic body 163. Moreover, at a portion opposed to the secondary-side sending/receiving coil 118, the primary-side sending/receiving coil 33 is provided for electromagnetic induction/coupling with the secondary-side sending/receiving coil 118.

Moreover, on the side opposed to the capsule portion 152 of the washing/disinfecting tank 4', the device-side sending/receiving antenna 32 is disposed.

In this construction, the used capsule type endoscope body 150 with which an endoscopic inspection has been finished is given preliminary washing at the bedside and then, at full washing, first, the capsule type endoscope body 150 is set at the washing/disinfecting tank 4' provided at the upper face of the device body 2 of the endoscope washing/disinfecting device 1A as predetermined.

Then, the scope connector portion 153 of the capsule type endoscope body 150 is opposed to the endoscope connection portion 31' provided on the outer circumferential wall surface of the washing/disinfecting tank 4'. Since the endoscope connection portion 31' basically has the same construction as that of the endoscope connection portion provided at the endoscope control unit or the AWS unit, they are in the structure capable of mutual connection.

Then, when the power switch of the endoscope washing/disinfecting device 1A is turned on, the scope attachment/detachment control circuit 56a provided at the electromagnetic unit 56 excites the electromagnet 56b, a magnetic force generated at the electromagnet 56b attracts the magnetic body 163 provided at the scope connector portion 153, and the scope connector portion 153 is connected to the endoscope connection portion 31'.

As a result, each of the pipeline bases 106a, 107a, 109a provided at the scope connector portion 153 and the water-leakage detection base 119 are automatically joined to the receiving-side bases 36a, 37a, 39a, 40 provided at the endoscope connection portion 31.

Therefore, in this embodiment, too, as with the first embodiment, at washing/disinfection of the capsule type endoscope body 150, the scope connector portion 153 can be joined to the endoscope connection portion 31 of the endoscope washing/disinfecting device 1A by one touch, connecting time can be drastically reduced and wrong connection or defective connection does not occur but reliable connection can be made.

Since the subsequent functional checks, washing process and disinfecting process are the same as those of the first embodiment, the description will be omitted.

The capsule type endoscope body 150 employed in this embodiment does not incorporate a valve or a mechanism for operating it from the insertion portion 151 to the capsule portion 152, and moreover, since the pipelines 106, 107, 109 are piped almost in the straight state, washing water and disinfectant can be prevailed through each of the pipelines 106, 107, 109 at washing and disinfection.

Third Embodiment

Figure 20:
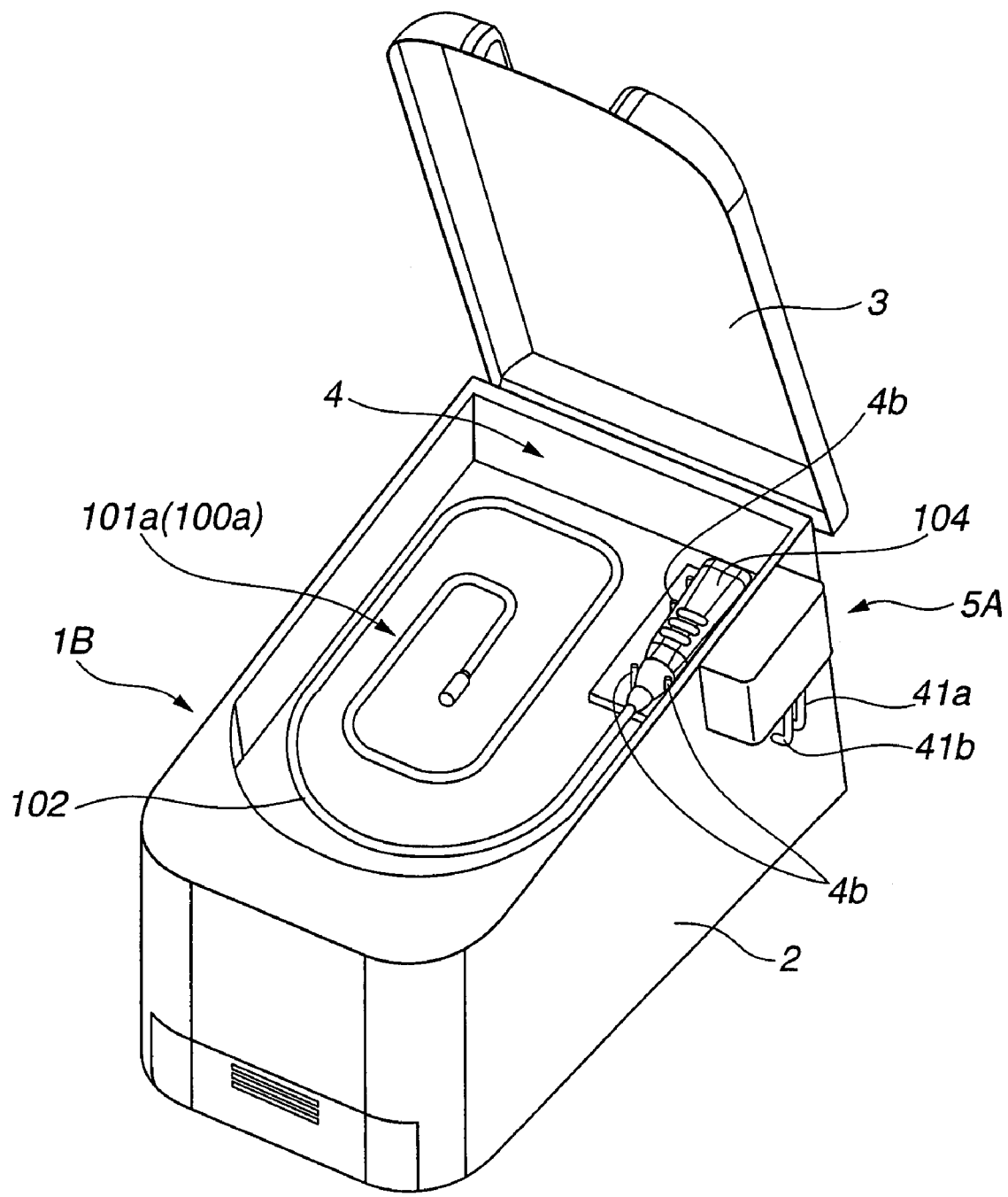
FIG. 20 is a perspective view of the endoscope washing/disinfecting device according to a third embodiment.
Figure 21:
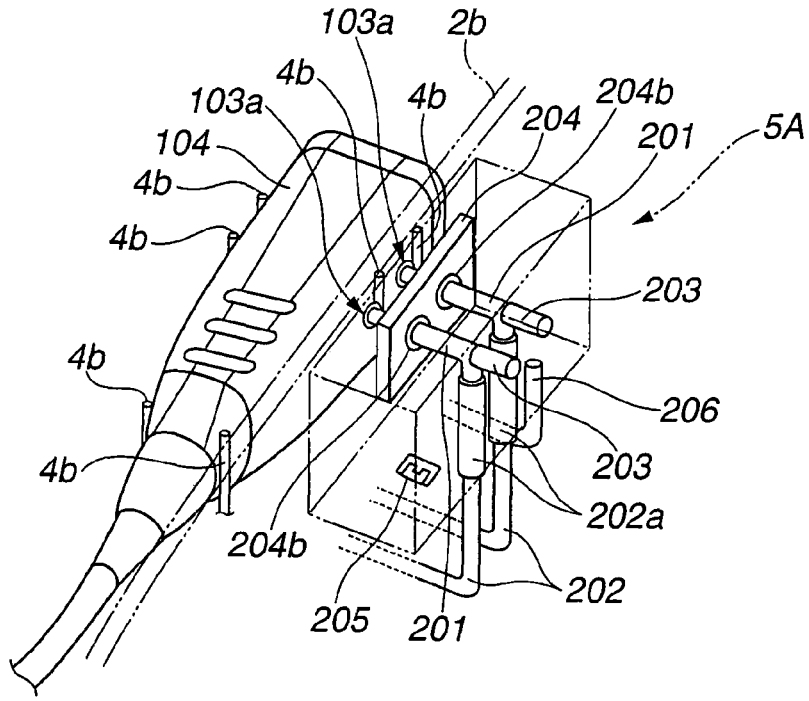
FIG. 21 is a partial perspective view for explaining the configuration of a pipeline automatic connecting unit according to the third embodiment.
Figure 22:
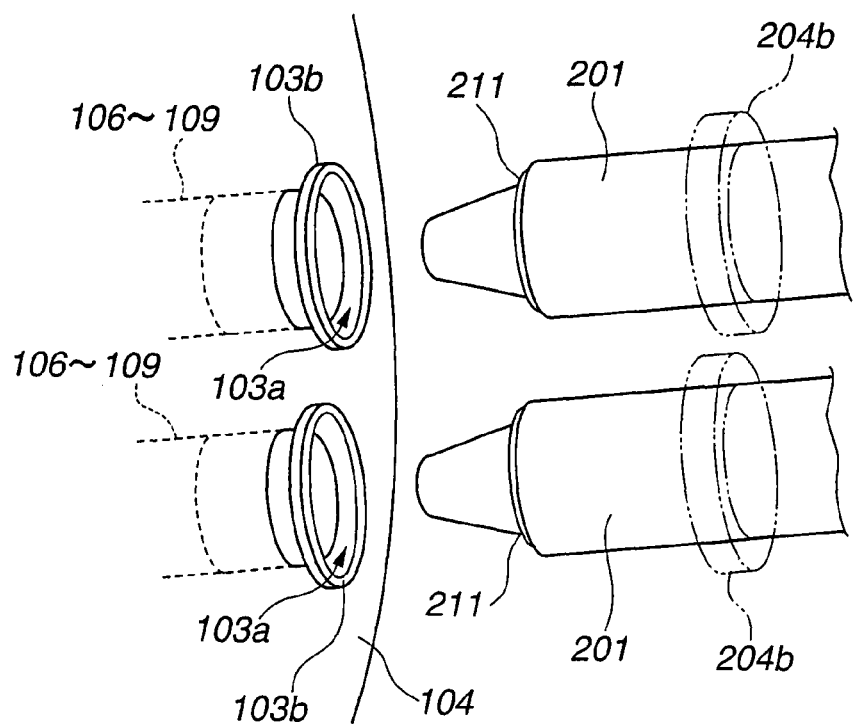
FIG. 22 is a partial perspective view for explaining a channel port of the endoscope and two connecting tubes according to the third embodiment.
Figure 23:
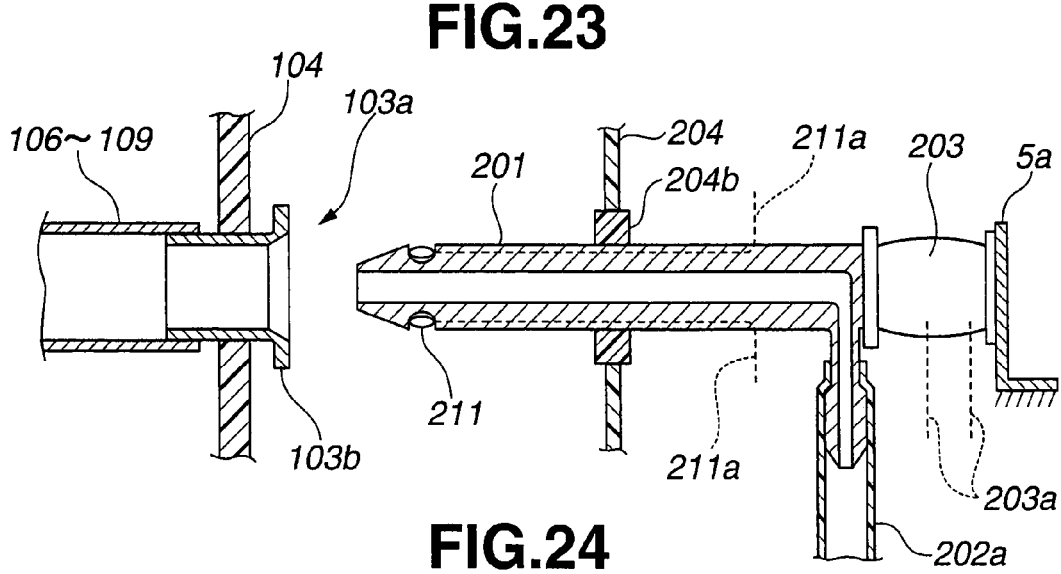
FIG. 23 is a view showing a case where an actuator is not extended according to the third embodiment.

Next, an endoscope washing/disinfecting device according to a third embodiment of the present invention will be described using FIGS. 20 to 30. FIG. 20 is a perspective view of an endoscope washing/disinfecting device according to a third embodiment, FIG. 21 is a block diagram schematically showing a construction of the endoscope washing/disinfecting device, FIG. 22 is a partial perspective view for explaining a construction of a pipeline automatic connection unit, and FIG. 23 is a partial perspective view for explaining a channel port and two connection pipes of an endoscope. The same constituents as those in the first and the second embodiments are given the same reference numerals and the description will be omitted.

In an endoscope body 101*a* accommodated within the washing/disinfecting tank 4 disposed in the device body 2 of an endoscope washing/disinfecting device 1B of this embodiment shown in FIG. 20, washing and disinfecting are carried out according to a predetermined washing/disinfecting sequence, which will be described later, in the state where the top cover 3 is closed so as to cover the washing/disinfecting tank 4 of the device body 2.

With the endoscope body 101*a*, the operation portion 104 is positioned and set between a plurality of pins 4*b* provided within the washing/disinfecting tank 4. A pipeline automatic connecting unit 5A is provided close to the positioned and accommodated operation portion 104 and on the outer wall portion of the device body 2. The pipeline automatic connecting unit 5A has a mechanism for automatically connecting a connection pipe to which the disinfectant or the like is supplied to a channel port of the endoscope body 101*a*, provided on the side wall of the device body 2 in this embodiment instead of the endoscope connection portions 31 shown in FIG. 5 of the first embodiment and connected to a washing/disinfecting tube 41*a* and a water-leakage detection tube 41*b*. The endoscope body 101*a* of this embodiment has substantially the same construction as that of the endoscope body 101 of the first embodiment, and a channel port 103*a* constitutes an opening of the pipelines 106 to 109 of the endoscope body 101*a* provided at the operation portion 104 as shown in FIG. 22. To a connection pipe 201 to which the channel port 103*a* is connected, the disinfectant and the like is supplied. The construction of the pipeline automatic connecting unit 5A will be described later.

FIG. 21 is a partial perspective view for explaining the construction of the pipeline automatic connecting unit 5A. The operation portion 104 of the endoscope body 101*a* is set between the plurality of pins 4*b* projecting within the washing/disinfecting tank 4. The plurality of pins 4*b* are positioning portion for arranging the operation portion 104 at a predetermined position in the washing/disinfecting tank 4 when mounted between the plurality of pins 4*b*. That is, when the operation portion 104 is mounted between the plurality of pins 4*b*, the plurality of pins 4*b* position the operation portion 104 at the predetermined position with respect to a side wall 2*b*, which is a part of the enclosure of the device body 2. Outside the side wall 2*b* opposite to the positioned operation portion 104, the pipeline automatic connecting unit 5A is provided as mentioned above.

The pipeline automatic connecting unit 5A has a sealed space inside, and a part of a connection pipe member penetrating a hole provided at a part of a bulkhead forming the sealed space in the sealed state (hereinafter referred simply as a connection pipe) 201 is arranged. When the two connection pipes 201 are moved by an actuator, which will be described later, the two connection pipes 201 are provided within the pipeline automatic connecting unit 5A so that the respective tip ends of the two connection pipes 201 are brought to positions capable of insertion into the two channel ports 103*a* of the endoscope body 101*a* positioned and set in the washing/disinfecting tank 4. To the two connection pipes 201, pipe members 202 for supplying the disinfectant or the like from the device body 2, respectively, are connected. The pipe member 202 is connected to a channel (channel) valve 38. The two connection pipes 201 are movable in a direction substantially crossing the face where the two channel ports 103*a* of the operation portion 104 are provided, respectively. In order to move the two connection pipes 201, an actuator 203 is provided at the base end portion of each of the connection pipes 201. The actuator 203 is made of a columnar artificial muscle (EPAM) member. The EPAM is a member stretched in a predetermined direction by applying a predetermined voltage. The actuator 203 is fixed in the pipeline automatic connecting unit 5A at one end, and when a predetermined voltage is applied under a control signal from the device-side control circuit 53, the other end is stretched so that the tip end of the connection pipe 201 is moved toward the channel port 103*a*. The EPAM member may be single or a plurality of them may be bundled.

Moreover, a seal guide member 204 having a hole through which each of the connection pipes 201 passes is provided in the pipeline automatic connecting unit 5A. The seal guide member 204 is fixed to the bulkhead portion on the operation portion 104 side in the pipeline automatic connection unit 5A. The seal guide member 204 may be a part of the bulkhead forming the sealed space or a part of the side wall portion of the enclosure on the operation portion 104 side of the device body 2.

At the hole 204*a* through each connection pipe 201 of the seal guide member 204 is inserted, an annular seal member 204*b* sliding with the outer circumferential face of each connection pipe 201 is provided while maintaining air tightness within the pipeline automatic connecting unit 5A even if each connection pipe 201 is moved in the axial direction. In other words, the connection pipe 201 is inserted through the hole of the seal guide member 204, and the annular seal member 204*b* is provided at the hole.

Moreover, an elastic pipeline, a rubber pipe 202*a*, for example, is interposed between each connection pipe 201 and the pipe member 202. This is to maintain the inside of the pipeline automatic connecting unit 5A air tight in the state where the pipe member 202 from the device body 2 is fixed to a part of the bulkhead face of the pipeline automatic connecting unit 5A even if each connection pipe 201 is moved within the pipeline automatic connecting unit 5A.

An electric wiring penetrating the wall portion of the pipeline automatic connecting unit 5A and withdrawn from the sealed space to the outside is sealed by a rubber bush, a seal bond and the like at the wall portion of the pipeline automatic connecting unit 5A.

Also, a water-leakage sensor 205 for detecting water leakage is provided on the bottom face portion within the pipeline automatic connecting unit 5A. This is to detect water leakage of the disinfectant or the like if the sealing performances of the seal member 204b provided at the seal guide member 204 is lost and the disinfectant or the like intrudes into the pipeline automatic connecting unit 5A during washing or the like in the washing/disinfecting tank 4. As will be mentioned later, when the water-leakage sensor 205 detects water leakage of the disinfectant or the like, the device-side control circuit 53 executes error processing such as warning display or warning sound to notify the user of the water leakage or stop of the sequence of the washing or the like.

Moreover, a nozzle, that is, a tip end portion of a pipeline 206 for supplying air into the pipeline automatic connecting unit 5A in order to maintain the internal pressure of the bulkhead of the pipeline automatic connecting unit 5A higher than an ambient pressure is provided inside the bulkhead. The pipeline 206 is connected to the base 40 for supplying air into the pipeline automatic connecting unit 5A, and at least when a liquid such as the disinfectant or the like is filled in the washing/disinfecting tank 4, the pressure inside the sealed space is maintained higher than that in the washing/disinfecting tank 4. As a result, even if the sealing performance is lost due to breakage of the seal guide member 204 or the like, the liquid such as the disinfectant does not intrude from the washing/disinfecting tank 4 immediately.

FIG. 22 is a partial perspective view for explaining the channel port 103a of the endoscope body 101a and the connection pipe 201. Though two connection pipes 201 are shown in FIG. 22, the number of connection pipes 201 matching the number of pipeline openings of the pipelines 106 to 109 of the endoscope body 101a are provided at the pipeline automatic connecting unit 5A. In this embodiment, the two connection pipes 201 are shown and described for simplicity.

The tip end portion of each connection pipe 201 has a conical shape whose outer diameter is reduced toward the tip end portion and the tip end is cut off. At the conical shaped portion of the tip end portion, a packing 211 is provided at a portion substantially equivalent to the inner diameter of the channel port 103a.

In FIG. 22, the seal guide member 204 is omitted and only the seal member 204b is shown by a two-dotted chain line. The seal member 204b is made of an elastic member such as rubber, and the inner circumferential portion of the seal member 204b is brought into close contact with the outer circumferential face of the connection pipe 201 in the state capable of sliding.

To the channel port 103a of the operation portion 104, a base 103b is provided, and the base 103b is connected to each of the pipelines 106 to 109 in the endoscope body 101a.

Figure 24:
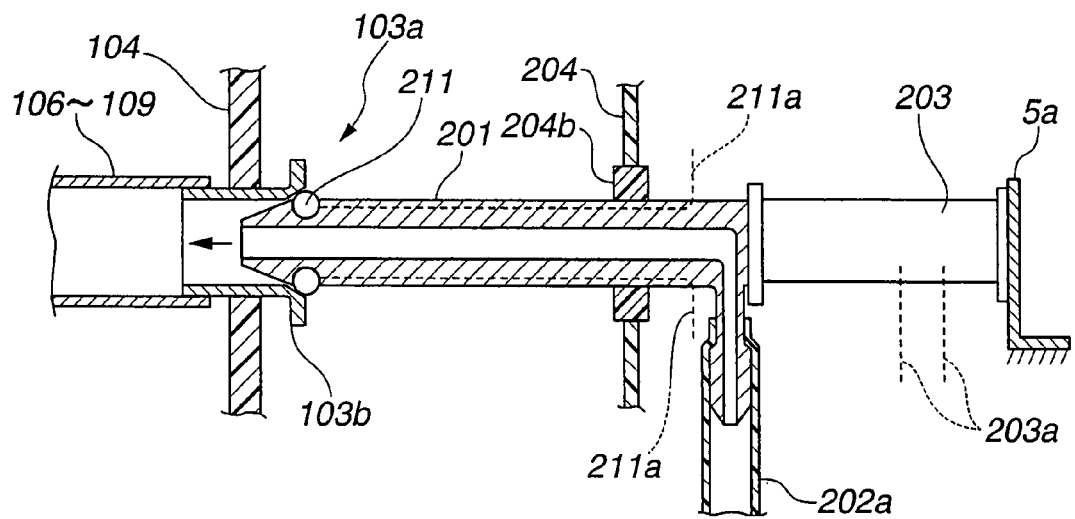
FIG. 24 is a view showing a state where the actuator is extended and a packing is expanded in the outer circumferential direction according to the third embodiment.
Figure 25:
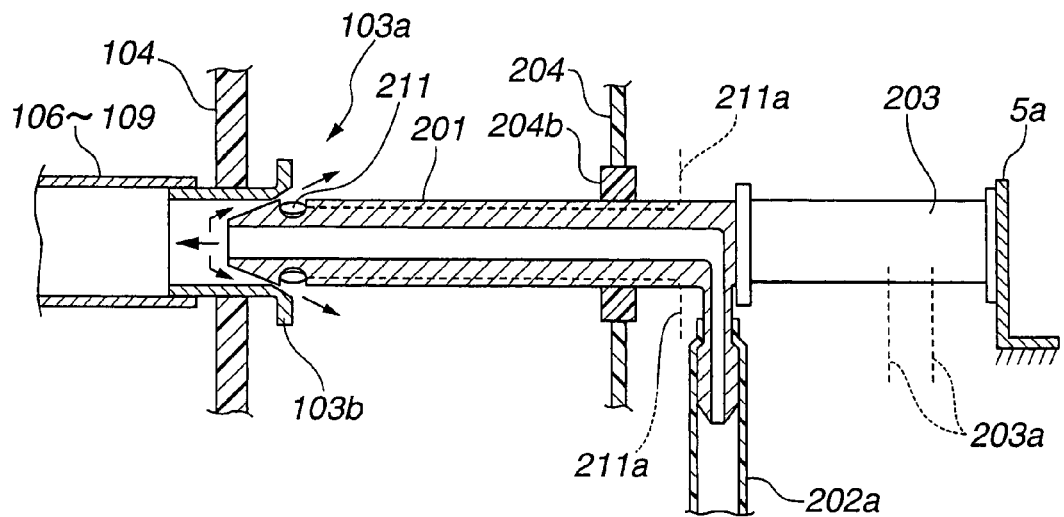
FIG. 25 is a view showing a state where the actuator is extended and the packing is not expanded in the outer circumferential direction according to the third embodiment.

The packing 211 is an annular artificial muscle member. FIGS. 23 to 25 are views for explaining an operation of the actuator 203 and the packing 211. FIG. 23 is a view showing a state where the actuator 203 is not stretched, FIG. 24 is a view showing a state where the actuator 203 is stretched and the packing 211 is extended in the outer circumferential direction, FIG. 25 is a view showing a state where the actuator 203 is stretched and the packing 211 is not extended in the outer circumferential direction. Here, an example that the base 103b is provided at the channel port 103a is described, but the base 103b does not have to be used.

One end of the actuator 203 is fixed to the inner wall of the pipeline automatic connecting unit 5A through a fixing member 5a in the pipeline automatic connecting unit 5A. And as mentioned above, the other end of the actuator 203 is fixed to one end of the connection pipe 201. The actuator 203 is stretched when a predetermined voltage is applied through an electric connection line 203a shown by a dotted line and moves the tip end portion of the connection pipe 201 in the direction of the channel port 103a of the operation portion 104. The packing 211 is also stretched in the radial direction crossing the axial direction of the connection pipe 201 when a predetermined voltage is applied through an electric connection line 211a shown by a dotted line.

In the washing process, the predetermined voltage is applied to the actuator 203 and the connection pipe 201 is moved from a position shown in FIG. 23 to a position shown in FIG. 24. After that, the predetermined voltage is applied to the packing 211, and the packing 211 is expanded in the outer diameter direction. In the state shown in FIG. 24, when the disinfectant passes through the connection pipe 201 and is supplied into the channel of the endoscope body 101a through the channel port 103a, the packing 211 is brought into the close contact state with the base 103b, and insides of the channels of the pipelines 106 to 109 of the endoscope body 101a are washed and disinfected.

When application of the predetermined voltage to the packing 211 is stopped, the packing 211 is contracted from the extended state in the outer diameter direction to the inner diameter direction, and a gap is generated between the channel port 103a and the outer circumferential face of the connection pipe 201. As shown in FIG. 25, when the packing 211 is not extended in the outer diameter direction, the disinfectant or the like is blown out of the channel port 103a of the base 103b. Therefore, in the state in FIG. 25, the inner circumferential face of the base 103b in contact with the packing 211 can be also washed and disinfected in the state in FIG. 24.

Figure 26:
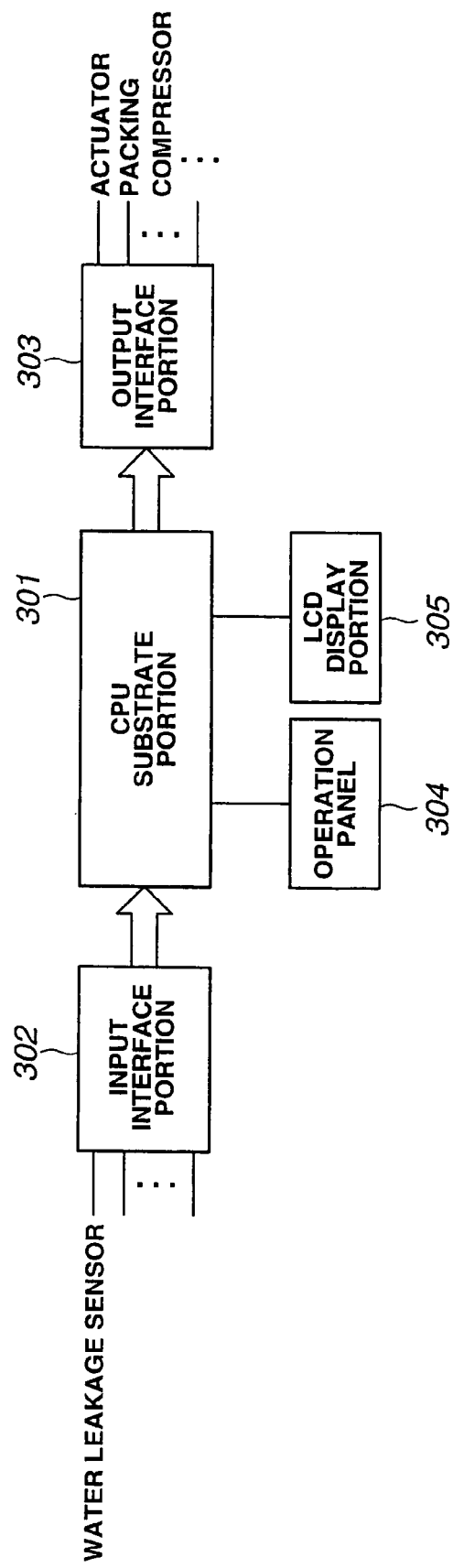
FIG. 26 is a block diagram showing a schematic construction of the endoscope washing/disinfecting device according to the third embodiment.
Figure 27:
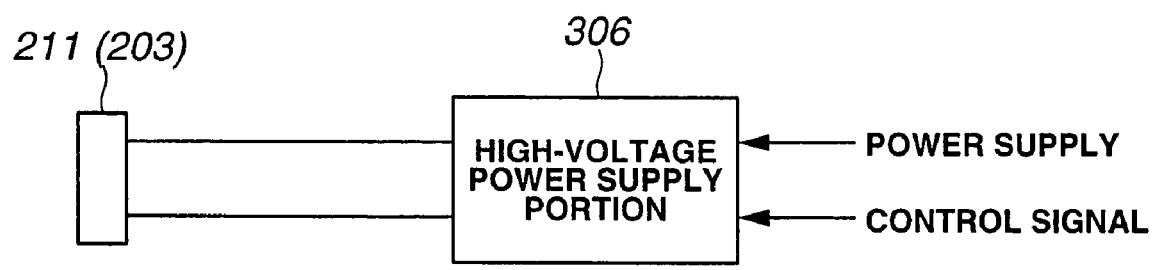
FIG. 27 is a block diagram showing a circuit for operating the packing, which is an artificial muscle member according to the third embodiment.
Figure 28:
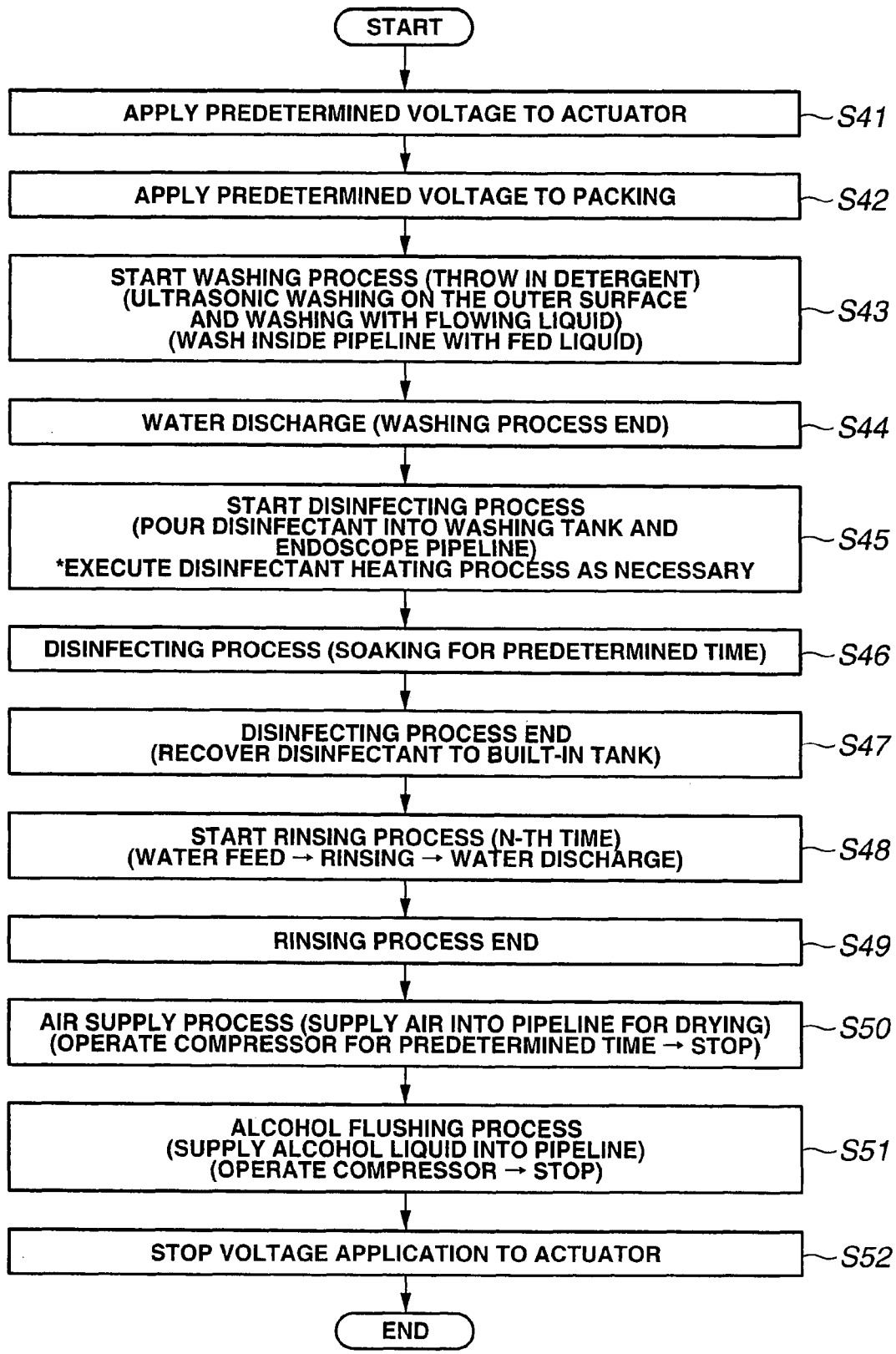
FIG. 28 is a flowchart showing an example of a processing flow of a washing/disinfecting process according to the third embodiment.

Next, electrical constitution of the endoscope washing/disinfecting device 1B will be described. FIG. 26 is a block diagram showing an outline construction of the endoscope washing/disinfecting device 1B, FIG. 27 is a block diagram showing a circuit for operating the packing 211, which is an artificial muscle member, and FIG. 28 is a flowchart showing an example of a flow of the washing/disinfecting process.

As shown in FIG. 26, the device-side control circuit 53 (See FIG. 5) of the endoscope washing/disinfecting device 1B comprises a CPU substrate portion 301, an input interface portion 302 for relaying a signal from sensors or the like to the CPU substrate portion 301, an output interface portions 303 for relaying an output signal to the actuator or the like, an operation panel 304 having operation switches and the like connected to the CPU substrate portion 301, and an LCD display portion 305 as display portion. Though the operation panel 304 and the LCD display portion 305 are not shown in FIG. 20, they are provided on the exterior surface of the enclosure of the endoscope washing/disinfecting device 1B, for example.

The CPU substrate portion 301 has various circuits for executing software programs such as a central processing unit (CPU), a ROM, and a RAM. A program for executing the washing/disinfecting sequence, which will be described later, is recorded in the ROM, and the CPU executes the program. To the input interface portion 302, a signal from various sensors such as the water-leakage sensor 205 is inputted, and the inputted signal is converted to a form which can be processed at the CPU substrate portion 301. The output interface portion 303 converts an output signal from the CPU substrate portion 301 to an output signal to the actuator 203, the packing 211, the compressor and the like.

The operation panel 304 is an input portion for giving an instruction such as start of washing by a user performing the washing/disinfecting work. The LCD display portion 305 is a display portion for the CPU substrate portion 301 to display the instruction contemns inputted by the user and a result of execution of the washing/disinfecting processing.

When the user sets the used endoscope body 101a between the plurality of pins 4b in the washing/disinfecting tank 4 and presses a predetermined switch on the operation panel 304 after the top cover 3 is closed, the washing/disinfecting processing is executed automatically.

FIG. 27 is a block diagram showing a circuit for operating the packing 211, which is an artificial muscle member. As shown in FIG. 27, the packing 211 is connected to a high-voltage power supply portion 306 so that a voltage from the high-voltage power supply portion 306 is applied. Electric power from the power supply and a control signal from the CPU substrate portion 301 through the output interface portion 303 are inputted to the high-voltage power supply portion 306. Thus, under the control signal from the CPU substrate portion 301, the high-voltage power supply portion 306 supplies a predetermined voltage to the packing 211. The circuit configuration for operating the actuator 203 is the same as the block diagram shown in FIG. 27, and the description will be omitted.

Next, using FIG. 28, a flow of the processing in the washing/disinfecting sequence executed by the CPU substrate portion 301 will be described. When a switch for instructing start of the washing/disinfecting processing of the operation panel 304 is pressed, first, a predetermined voltage is applied to each actuator 203 (Step (hereinafter abbreviated as S) 41). By this, the connection pipe 201 is moved to the direction of the channel port 103a and arranged at a position shown in FIG. 25. Then, a predetermined voltage is applied to the packing 211 (S42). By this, the packing 211 is expanded in the outer diameter direction to be brought into the state shown in FIG. 24, and a space between the connection pipe 201 and the base 103b is sealed.

When the switch for instructing start of the washing/disinfecting processing of the operation panel 304 is pressed, the CPU substrate portion 301 monitors output of the water-leakage sensor 205 all the time and if it receives a signal indicating water leakage, it executes the above-mentioned error processing.

Then, the washing process is started (S43). In the washing process, the detergent is supplied from the detergent tank 11 through the detergent pump 27, and under a predetermined control signal from the CPU substrate portion 301, various pumps and valves are controlled and moreover, the ultrasonic vibrator 49 (shown in FIG. 5) and the heater are also started, and the outer surface of the endoscope body 101a is ultrasonic-washed by the washing liquid. At the same time, the washing liquid is supplied from the channel 103a into each of the pipelines 106 to 109 of the endoscope, and washing is carried out in each of the pipelines 106 to 109. Application of the predetermined voltage to the packing 211 is stopped at a predetermined timing and the packing 211 is brought from the state expanded in the outer diameter direction to the state contracted in the inner diameter direction so that a gap is generated between the connection pipe 201 and the base 103b as shown in FIG. 25. In the state shown in FIG. 25, the washing liquid injected out of the connection pipe 201 can flow out to the outside of the endoscope body 101a as shown by an arrow from the gap between the connection pipe 201 and the base 103b, a contact surface of the base 103b of the endoscope body 101a with the connection pipe 201 is also washed by the washing liquid. Timings of change from the state in FIG. 24 to the state in FIG. 25 and return from the state in FIG. 25 to the state in FIG. 24 are executed by a control signal from the CPU substrate portion 301 to the packing 211 for the predetermined number of times and for a predetermined duration.

When the predetermined washing process is executed in this way, the washing process is finished, and water is discharged (S44). The discharge from the discharge port 20 is carried out by controlling the switching valve 52 and the discharge pump 34.

Then, the disinfecting process is started (S45). In the disinfecting process, the disinfectant is supplied from the disinfectant tank 12 through the drug pump 28, and under a predetermined control signal from the CPU substrate portion 301, the various pumps and valves are controlled, and the outer surface of the endoscope body 101a is disinfected by the disinfectant. At the same time, the disinfectant is supplied from the channel port 103a into each of the pipelines 106 to 109 of the endoscope body 101a, and inside of each of the pipelines 106 to 109 is disinfected. At this time, in the packing 211, application of the predetermined voltage is stopped at a predetermined timing as with the washing process, and as shown in FIG. 25, it is brought from the state expanded in the outer diameter direction to the state contracted in the inner diameter direction so that a gap is generated between the connection pipe 201 and the base 103b. In state shown in FIG. 25, the disinfectant injected out of the connection pipe 201 can flow out to the outside of the endoscope body 101a from the gap between the connection pipe 201 and the base 103b, and the contact area of the base 103b of the endoscope body 101a with the connection pipe 201 is also disinfected by the disinfectant. Change from the state in FIG. 24 to the state in FIG. 25 is executed by a control signal from the CPU substrate portion 301 for the predetermined number of times and for a predetermined duration. In the disinfecting process, the disinfectant may be heated by a heater.

Moreover, the disinfecting process for soaking for a specified time is carried out (S46).

When the predetermined disinfecting process is executed as above, the disinfecting process is finished, and the disinfectant is recovered (S47). Recovery of the disinfectant is executed by controlling the switching valve 52.

Then, a rinsing process is started (S48). In the rinsing process, tap water is supplied by the water tap into the washing/disinfecting tank 4 from the connector 50 for water-feed pipeline disinfection through a check valve. The supplied tap water is taken in from the circulation port 21 in the state where the feed-water/circulation nozzle 24 is connected to the liquid pump 30 through the three-way switching valve 29 and circulated. At the same time, circulation water is supplied into each of the pipelines 106 to 109 of the endoscope body 101a from the channel port 103a, and inside of each of the pipelines 106 to 109 is rinsed. At this time, too, change from the state in FIG. 24 to the state in FIG. 25 and return from the state in FIG. 25 to the state in FIG. 24 are executed by a control signal from the CPU substrate portion 301 to the packing 211 for the predetermined number of times and for a predetermined duration.

This rinsing process is carried out the predetermined number of times (N times) with water-feed, rinsing and discharge as 1 cycle.

When the rinsing process is executed as above for the predetermined number of times, the rinsing process is finished (S49).

After that, an air supply process is executed (S50). In the air supply process, air is fed into each of the pipelines 106 to 109 of the endoscope body 101a so as to dry inside of each of the pipelines 106 to 109. Therefore, the compressor 44 is operated for a specified time, and air is supplied into each of the pipelines 106 to 109 of the endoscope body 101a from the connection pipe 201 through the compressor 44 to the air filter 15 and the channel block 42.

When the air supply process is finished, the compressor 44 is stopped, an alcohol flushing process is executed (S51). In the alcohol flushing process, the alcohol pump 35 is started for a predetermined time so as to feed alcohol into each of the pipelines 106 to 109 of the endoscope body 101a. The alcohol pump 35 is stopped after the predetermined time has elapsed.

Lastly, by stopping application of the predetermined voltage to the actuator 203 (S52), the actuator 203 is returned from the stretched state to the original state, and the connection pipe 201 is returned to the state shown in FIG. 23.

As mentioned above, according to this embodiment, insides of the various channels provided within the used endoscope body 101a can be surely washed and disinfected or the like.

Fourth Embodiment

Figure 29:
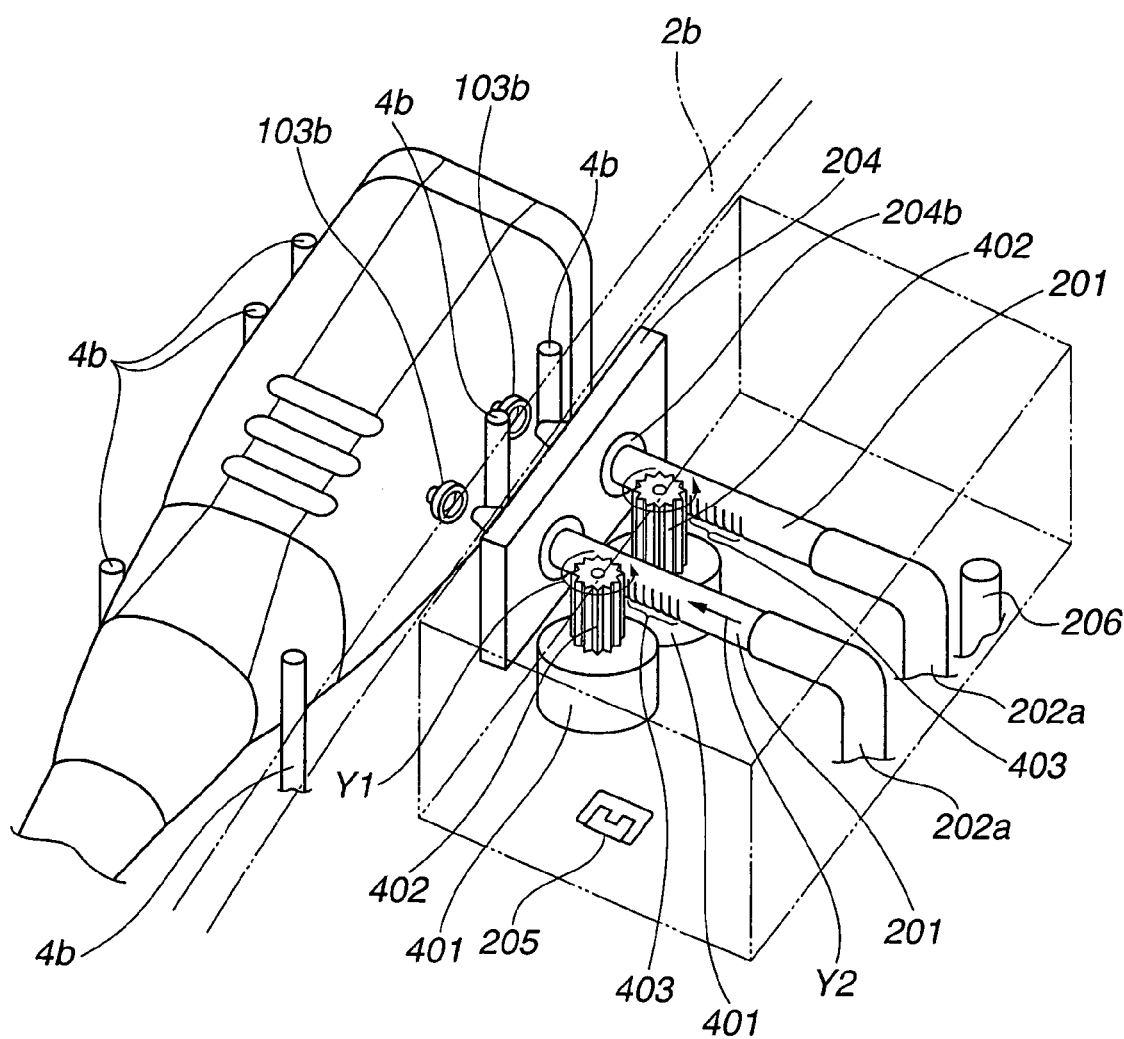
FIG. 29 is a perspective view for explaining the actuator according to a fourth embodiment.
Figure 30:
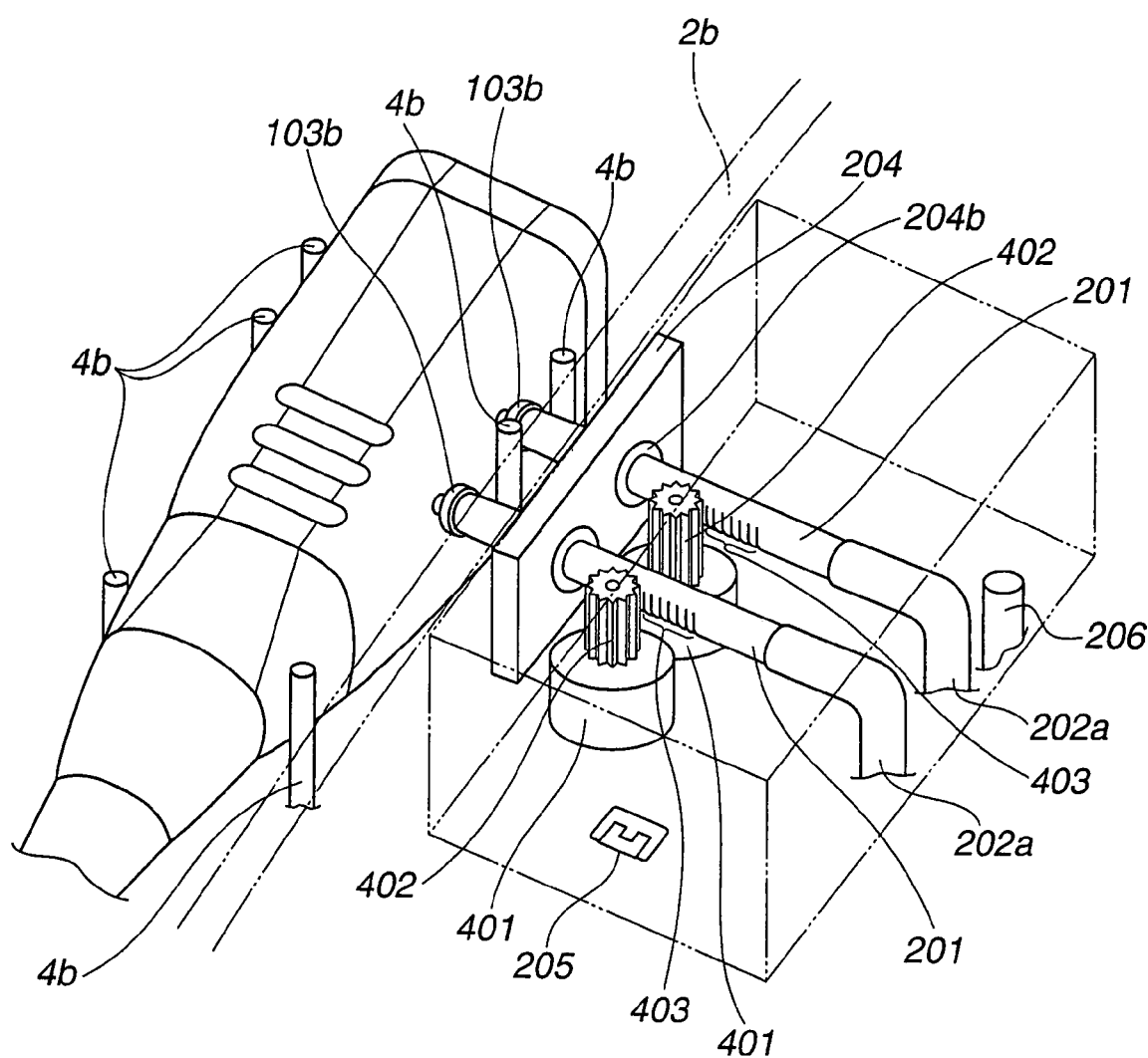
FIG. 30 is a perspective view for explaining the actuator according to the fourth embodiment.

Next, a variation of the actuator will be described as a fourth embodiment. FIGS. 29 and 30 are perspective views for explaining the variation of the actuator of this embodiment according to the third embodiment. In the above example, the actuator 203 uses an artificial muscle member, but in this embodiment, a rack-and-pinion mechanism is used. In this embodiment, too, the same components as those in the embodiments are given the same reference numerals and the description will be omitted.

As shown in FIG. 29, in this embodiment, in the pipeline automatic connecting unit 5A, motors 401 are provided corresponding to the respective connection pipes 201 as actuators. At the shaft of the motor 401, a gear 402 is provided. On the outer surface portion of the connection pipe 201, teeth portions 403 made of a plurality of teeth provided along the axial direction are provided. The gear 402 of the motor 401 and the connection pipe 201 are positioned so that the teeth of the gear 402 and the teeth of the teeth portions 403 are meshed with each other.

Therefore, instead of application of a predetermined voltage to the above actuator 203, when the CPU substrate portion 301 supplies a driving signal to rotate the motor 401 by a predetermined amount to the motor 401, the connection pipe 201 is moved toward the base 103b to the position as shown in FIG. 24. FIG. 30 shows a state where the motor 401 is rotated by the predetermined amount, and the connection pipe 201 is moved to the position shown in FIG. 29. In FIG. 29, when the gear 402 mounted at the shaft of the motor 401 is rotated in the direction shown by an arrow Y1, the connection pipe 201 is moved to the direction shown by an arrow Y2.

Instead of stop of application of the predetermined voltage to the above actuator 203, by supplying a driving signal to reverse the motor 401 by a predetermined amount to the motor 401, the connection pipe 201 can be returned to the original position shown in FIG. 23.

Therefore, according to this embodiment, too, as with the above first embodiment, the endoscope body 101a can be washed and disinfected.

As mentioned above, according to the endoscope washing/disinfecting device 1B according to the third and the fourth embodiments, the connection pipe for supplying the washing liquid and the like to the pipelines 106 to 109 of the endoscope body 101a of the set endoscope 100a is surely brought into the close contact state and the washing liquid and the like can be supplied to the pipelines 106 to 109. Moreover, if an artificial muscle member is used for the packing and the actuator, the number of mechanically moving parts is reduced, and occurrence of failures or the like is also decreased. Furthermore, since a water-leakage sensor is provided in the pipeline automatic connecting unit 5A and inside of the pipeline automatic connecting unit 5A is pressurized, the failure occurrence rate is further decreased similarly.

Fifth Embodiment

An endoscope washing/disinfecting device according to a fifth embodiment of the present invention will be described using FIGS. 31 to 33. What is different from the first embodiment is that the packing 211 is provided in the endoscope body 101a. Therefore, the same components as those in the above third and the fourth embodiments, the same reference numerals are given and the description will be omitted.

Figure 31:
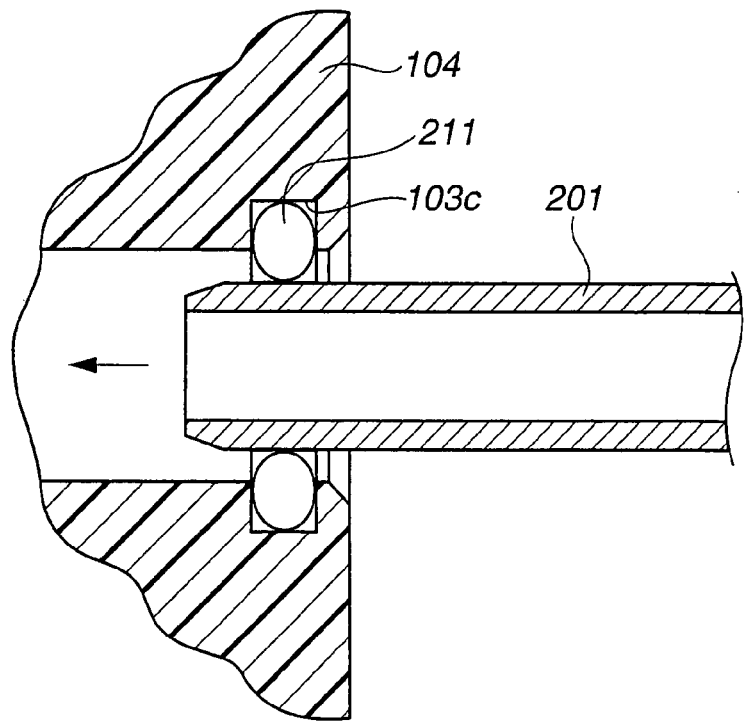
FIG. 31 is a partial sectional view for explaining a sealed state between a channel port and a connection pipe according to a fifth embodiment.
Figure 32:
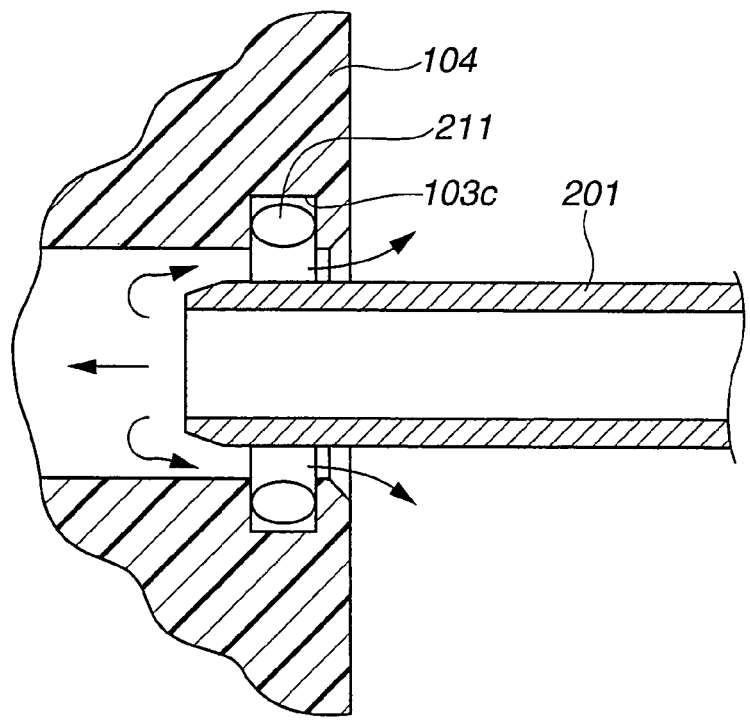
FIG. 32 is a partial sectional view for explaining a sealed state between a channel port and a connection pipe according to the fifth embodiment.

FIGS. 31 and 32 are partial sectional views for explaining a state where the packing 211 is provided in the operation portion 104 of the endoscope body 101a, and the channel port 103a and the connection pipe 201 are sealed. FIG. 31 shows a state where the connection pipe 201 is inserted into the channel port 103a by the actuator and the packing, which is an artificial muscle member, is stretched, and as a result, the inner diameter of the packing 211 is reduced and the space between the connection pipe 201 and the channel port 103a is sealed. FIG. 32 shows a state where the connection pipe 201 is inserted into the channel port 103a by the actuator, the packing 211 is not stretched and as a result, the inner diameter of the packing 211 is increased and a gap is generated between the connection pipe 201 and the channel port 103a.

The annular packing 211 is provided in a circumferential groove 103c formed in the channel inner wall close to the channel port 103a. When a predetermined voltage is applied to the packing 211, the packing 211 is stretched in the diameter expanding direction, but since deformation in the outer diameter direction is restricted by the circumferential groove 103c, it results in deformation in the direction where the inner diameter is reduced. By this, similarly to the third embodiment, by controlling application of a predetermined voltage to the packing 211, the space between the connection pipe 201 and the channel port 103a can be brought into two states, a sealed state or a non-sealed state.

At this time, in order that the power is supplied to the endoscope body 101a set in the washing/disinfecting tank 4, circuit portion for supplying power from the endoscope washing/disinfecting device 1B to the endoscope body 101a is provided at the endoscope washing/disinfecting device 1B and the endoscope body 101a, respectively.

Figure 33:
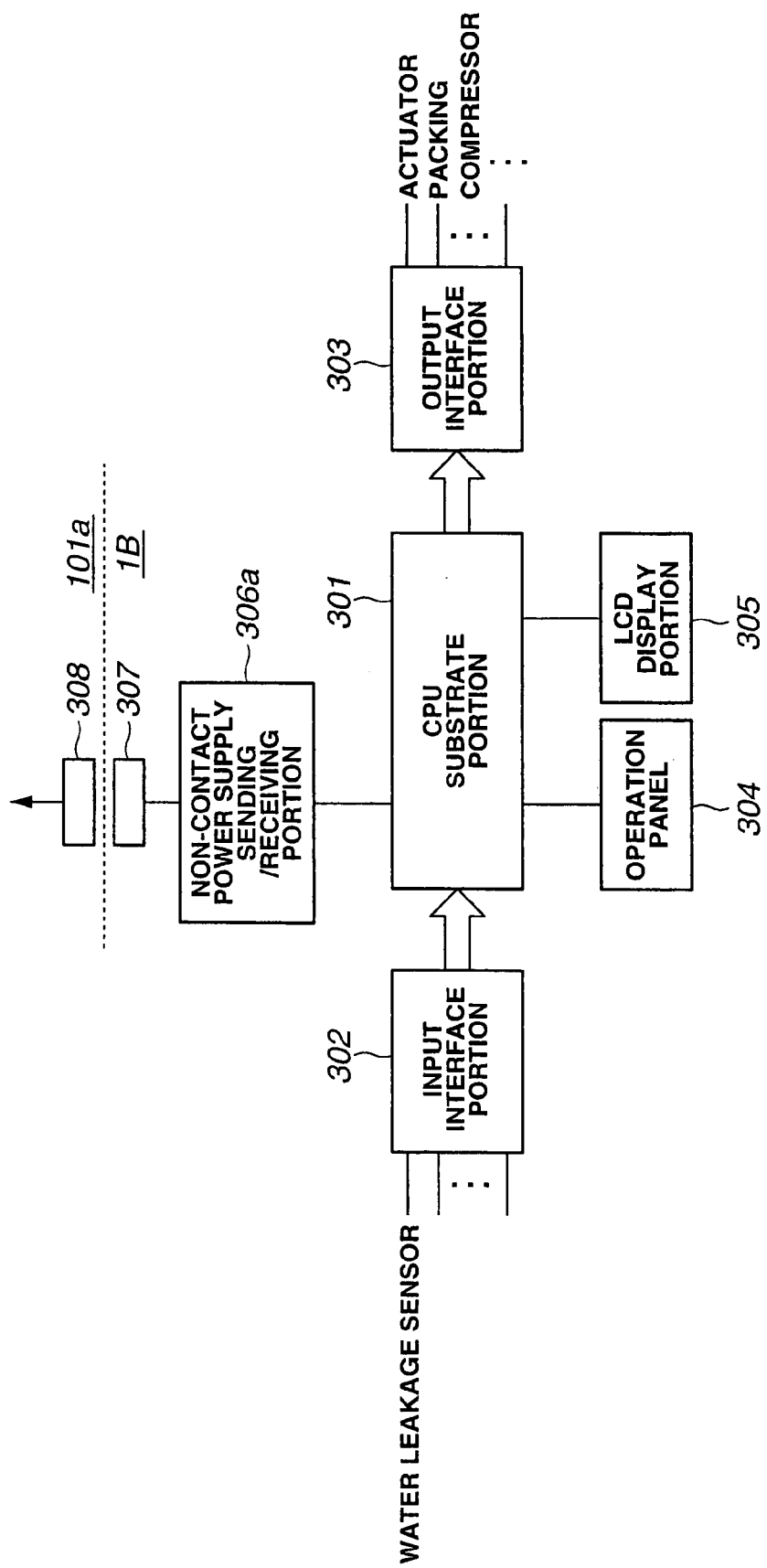
FIG. 33 is a block diagram showing an electrical constitution of the endoscope washing/disinfecting device according to the fifth embodiment.

FIG. 33 is a block diagram showing electric construction of the endoscope washing/disinfecting device 1B. As shown in FIG. 33, to the CPU substrate portion 301, a non-contact power supply sending/receiving portion 306a is connected. To the non-contact power supply sending/receiving portion 30a, a sending/receiving coil 307 is further connected. On the other hand, at the endoscope body 101a, a sending/receiving coil 308 is provided in the operation portion 104, for example, for receiving an electromagnetic wave from the sending/receiving coil 307 of the endoscope washing/disinfecting device 1B and generating a predetermined voltage based on the received electromagnetic wave.

The voltage generated at the sending/receiving coil 308 is used as power supply for generating a predetermined voltage to be applied to the above packing 211.

The CPU substrate portion 301 can stretch the packing 211 by sending a control signal to the non-contact power supply sending/receiving portion 306a at a predetermined timing in the above washing/disinfecting process. Thus, the CPU substrate portion 301 can bring the space between the connection pipe 201 and the channel port 103a into two states: a sealed state and a non-sealed state as with the third embodiment.

Therefore, according to this embodiment, too, the endoscope body 101a can be washed and disinfected as with the above third and the fourth embodiments.

As mentioned above, according to the endoscope washing/disinfecting device 1B according to the fifth embodiment, the connection pipe for supplying the washing liquid and the like to the pipelines 106 to 109 of the set endoscope body 101a can be surely brought into the close contact state and the washing liquid and the like can be supplied to the pipelines 106 to 109 as with the above third and the fourth embodiments.

Sixth Embodiment

Next, a sixth embodiment of the present invention will be described based on the attached drawings. In this embodiment, too, the same components as those in the above embodiments are given the same reference numerals and the description will be omitted.

Figure 34:
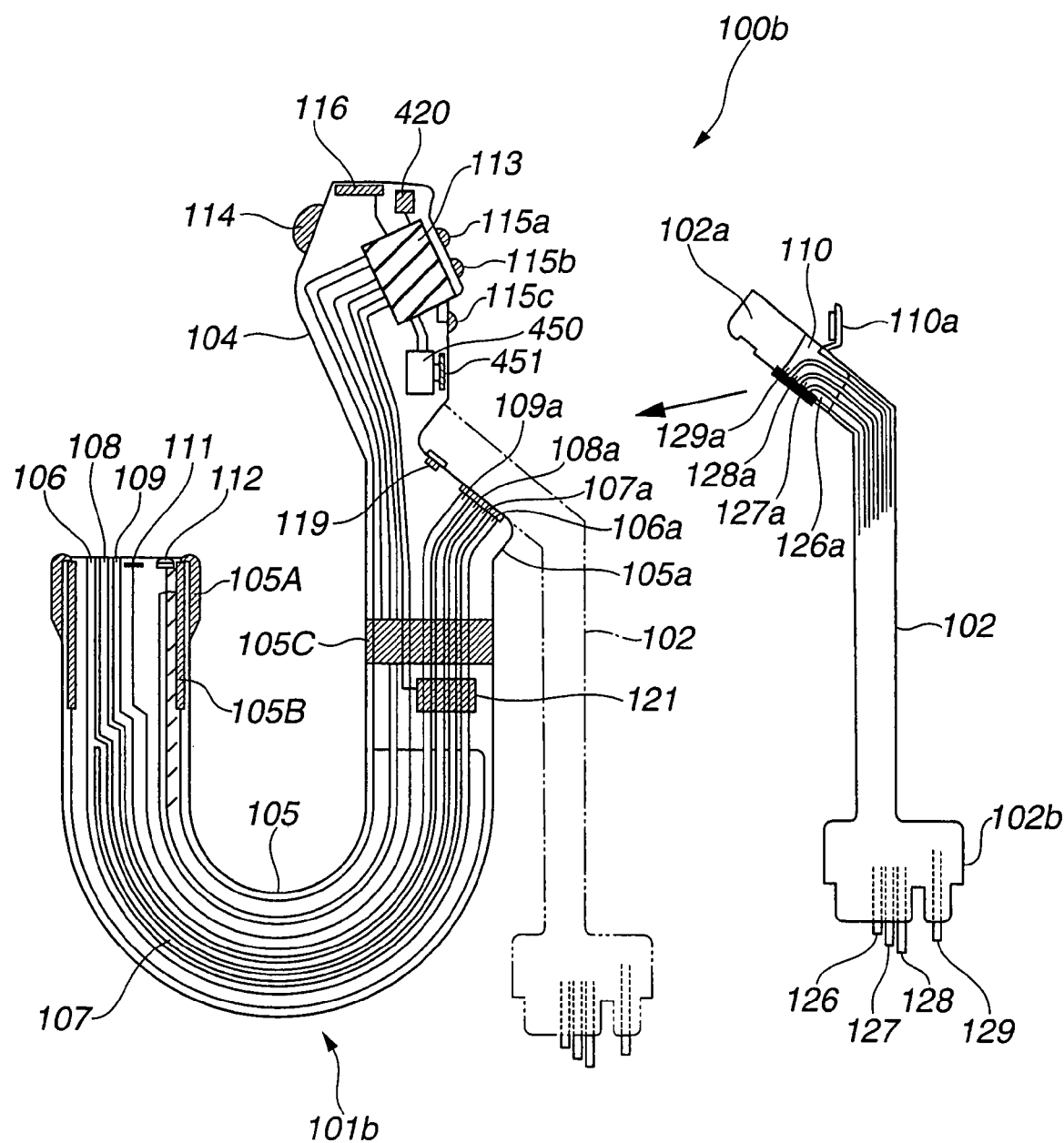
FIG. 34 is a view for explaining a construction of the endoscope of the endoscope washing/disinfecting device according to a sixth embodiment.
Figure 35:
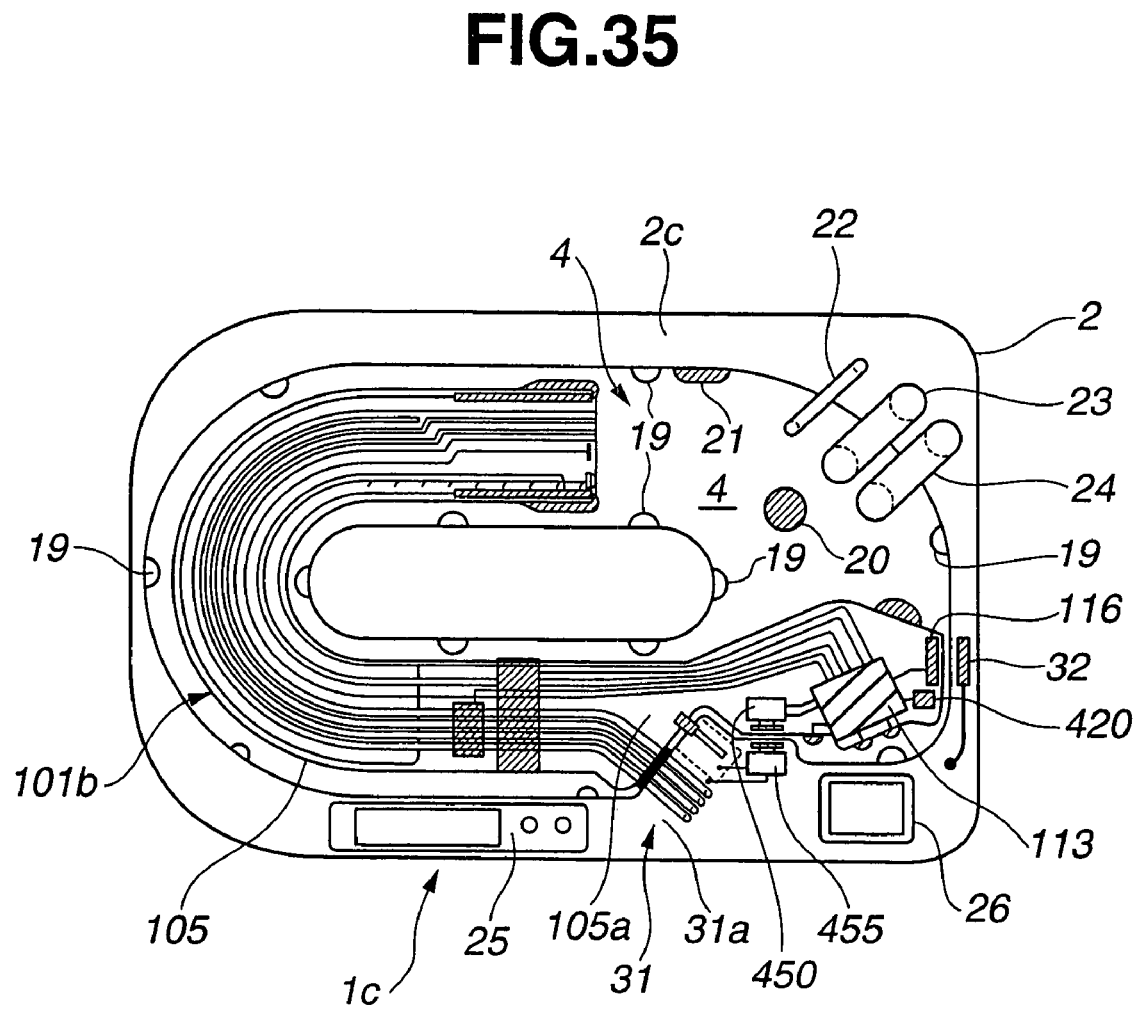
Figure 36:
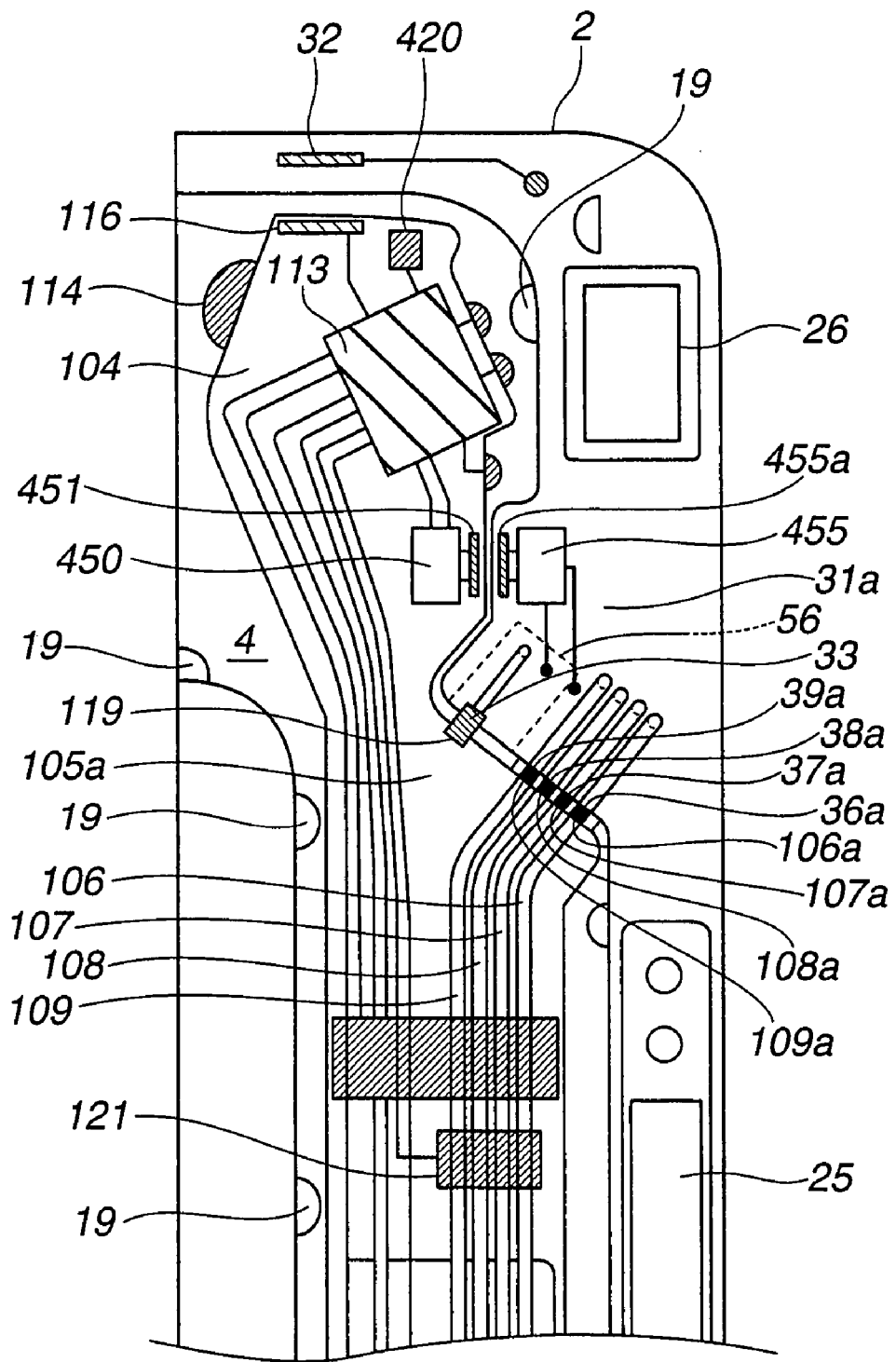
FIG. 36 is an enlarged view for explaining each connector portion of the washing/disinfecting tank and the endoscope according to the sixth embodiment.
Figure 37:
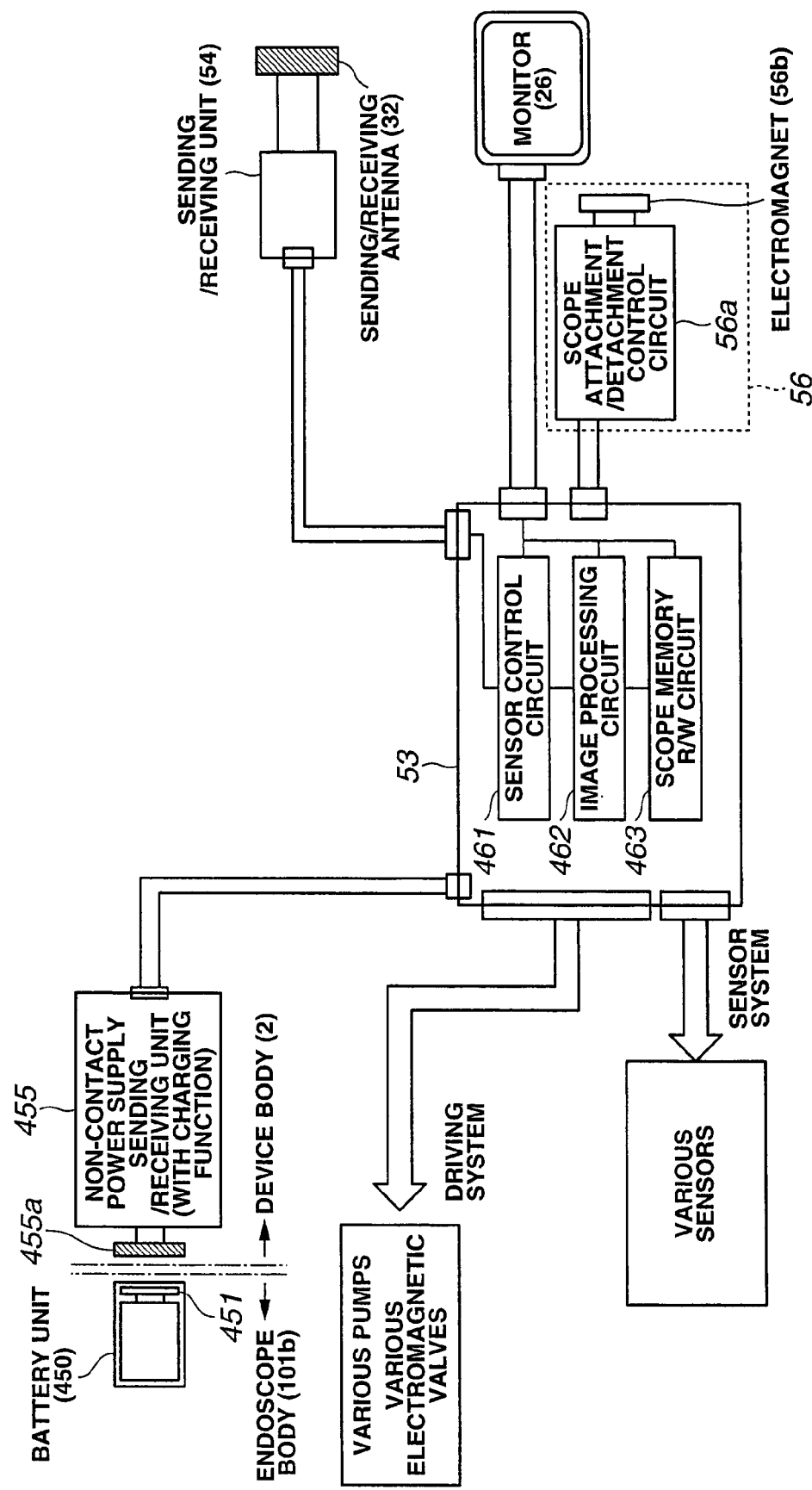
FIG. 37 is a block diagram showing a construction of a device-side control circuit in the device body according to the sixth embodiment.
Figure 38:
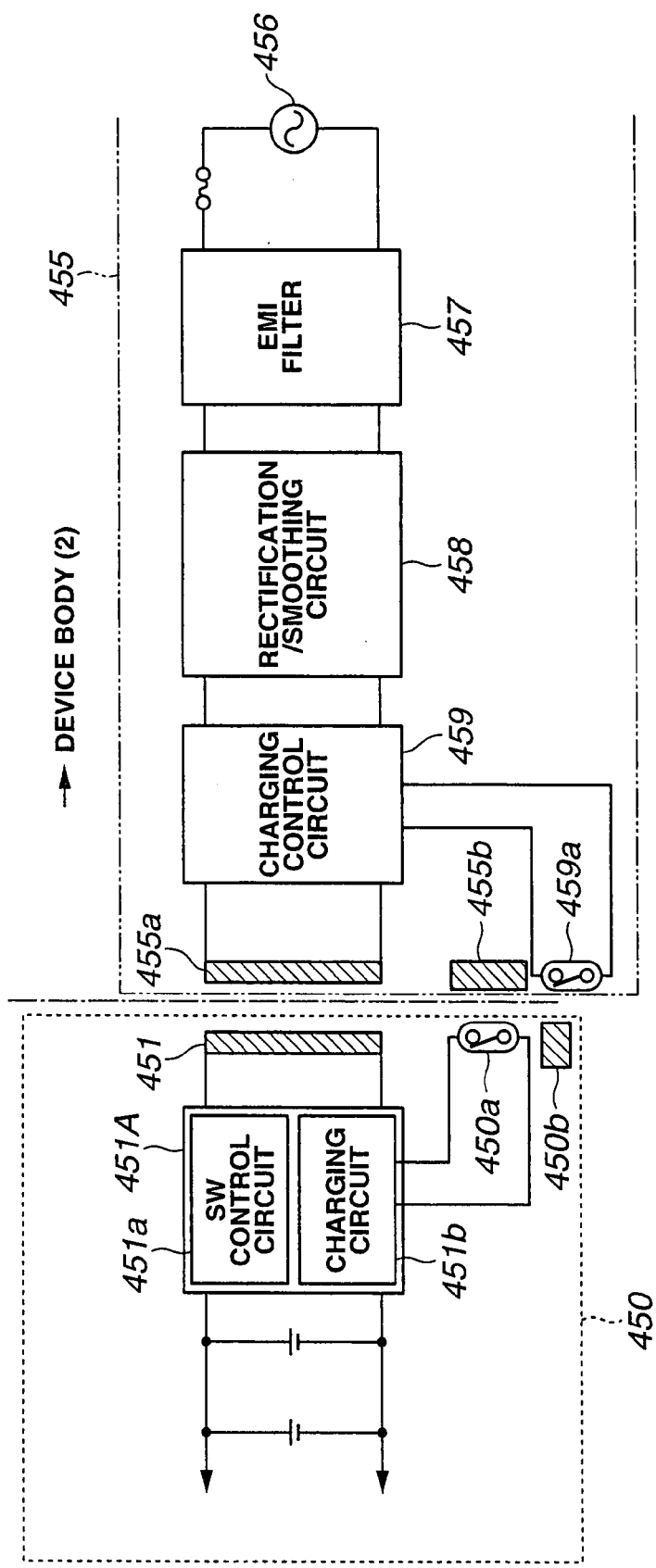
FIG. 38 is a block diagram showing a circuit construction of a battery unit and a non-contact power supply sending/receiving unit according to the sixth embodiment.
Figure 39:
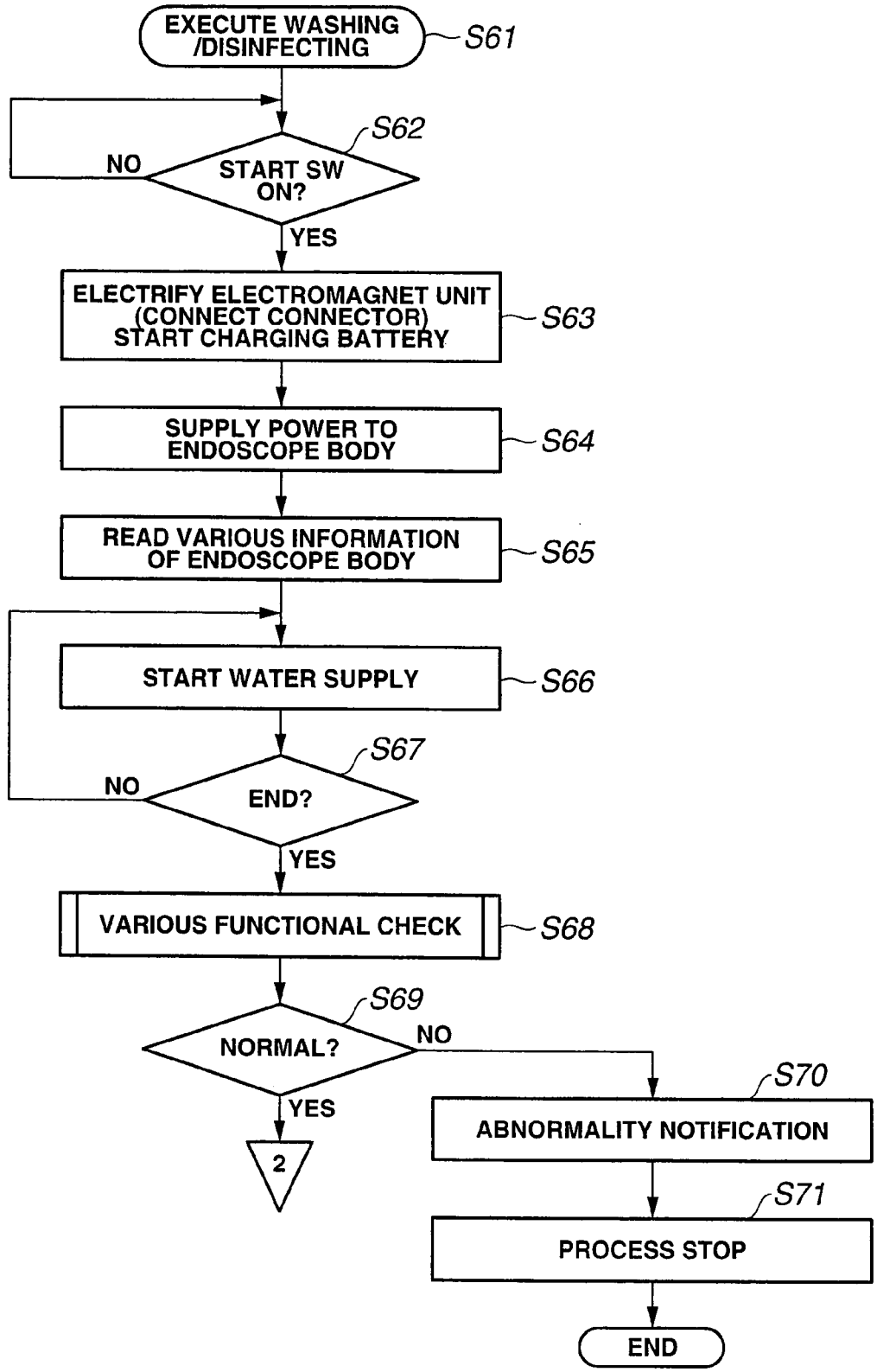
FIG. 39 is an operational flowchart of the endoscope washing/disinfecting device according to the sixth embodiment.
Figure 40:
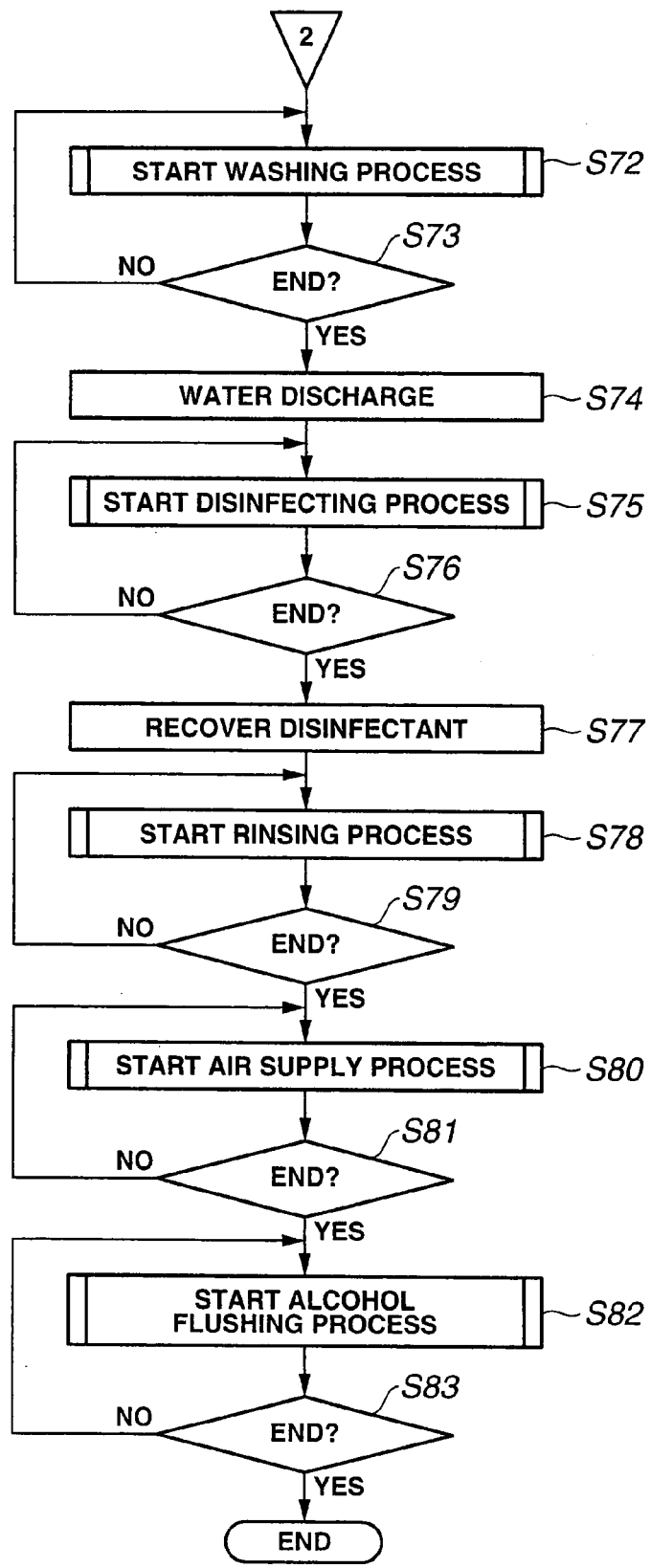
FIG. 40 is an operational flowchart of the endoscope washing/disinfecting device according to the sixth embodiment.
Figure 41:
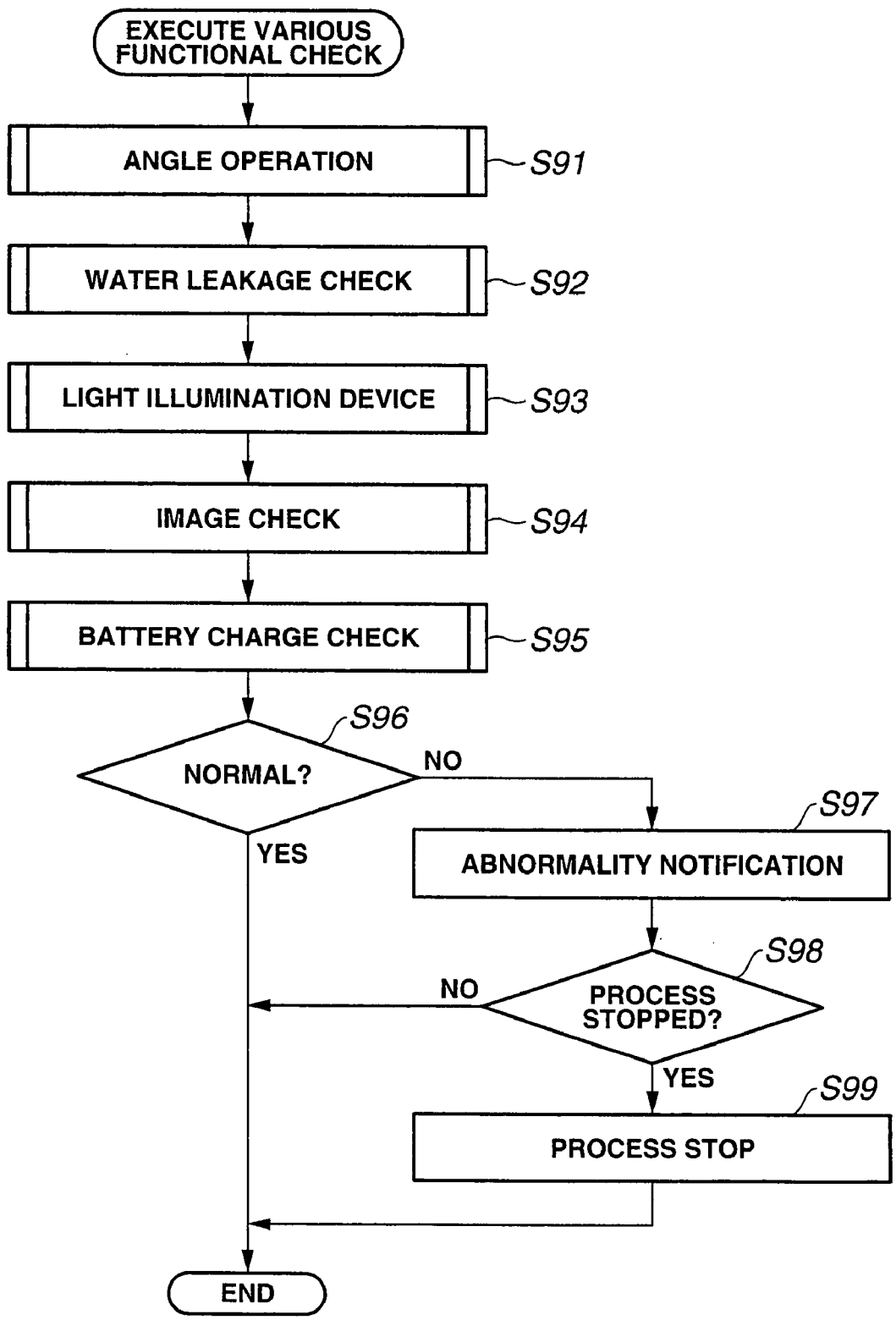
FIG. 41 is an operational flowchart of various functional checks of the endoscope body according to the sixth embodiment.

FIG. 34 is a view for explaining a construction of an endoscope of this embodiment, FIG. 35 is a view in which the endoscope is set at the washing/disinfecting tank of the endoscope washing/disinfecting device, FIG. 36 is an enlarged view for explaining the washing/disinfecting tank and each of the set connector portions of the endoscope, FIG. 37 is a block diagram showing a construction of the device-side control circuit in the device body, FIG. 38 is a block diagram showing a circuit configuration of a battery unit and a non-contact power supply sending/receiving unit, FIGS. 39 and 40 are operational flowcharts of the endoscope washing/disinfecting device, and FIG. 41 is an operation flowchart of various functional checks of the endoscope body.

First, an endoscope 100b employed in this embodiment shown in FIG. 34 is an endoscope in which a battery unit is mounted on the endoscope 100 of the first embodiment.

As shown in FIG. 34, in the operation portion 104 of the endoscope body 101b, a battery unit 450, which is connected to the endoscope-side control circuit 113 and is battery power supply portion for supplying a driving power to various equipment, is incorporated. This battery unit 450 has a sending/receiving coil 451, which is power transmission portion. This battery unit 450 is incorporated in the operation portion 104 so that one face of the sending/receiving coil 451 is arranged adjacently on one side face of the operation portion 104. Also, a pressure sensor 420 is disposed in the operation portion 104. The endoscope-side control circuit 113 checks if water leakage occurs in the endoscope body 101b on the basis of an internal pressure of the endoscope body 101b detected by the pressure sensor 420.

On an outer circumference at the tip end of the endoscope insertion portion 105 of the endoscope body 10b, a contact sensor 105A is disposed. This contact sensor 105A detects a contact pressure and the like at the tip end side of the endoscope insertion portion 105 with a body cavity wall, for example. Moreover, at the tip end portion of the endoscope insertion portion 105, an angle member 105B is disposed which is made of Electroactive Polymer (EPAM) for curved operation of the tip end portion of the endoscope insertion portion 105 according to operation of a track ball 114 of the operation portion 104.

At the endoscope insertion portion 105 of the endoscope body 101b, a hardness variable member 105C made of EPAM is disposed so that its flexibility can be freely changed. Also, at the endoscope-side control circuit 113, which is the power supply control portion of the endoscope body 101b, a memory device is provided, though not shown, and various information, recognition information and the like of the endoscope body 101b are stored in this memory device.

On the other hand, as shown in FIG. 35, a pipeline/leakage detection connector 31a of the endoscope connection portion 31 to be connected to the scope connector portion 105a of the endoscope body 101b is disposed at one side of the washing/disinfecting tank 4 provided at an endoscope washing/disinfecting device 1C. Moreover, as shown in FIG. 36, the device-side sending/receiving antenna 32 for receiving a signal from the sending/receiving antenna 116 provided at the endoscope body 101b or sending it to this sending/receiving antenna 116 is provided at the washing/disinfecting tank 4.

The pipeline/leakage detection connector 31a basically has the same construction as a code-side connector portion 102a provided at the above-mentioned universal cord 102. In detail, as shown in FIG. 36, bases 36a to 39a are provided at the tip end face of the pipeline/leakage detection connector 31a. Each of 36a to 39a is provided at a position corresponding to the bases 106a to 109a communicating with the base end of each of the pipelines 106 to 109 provided at the scope connector portion 105a of the endoscope body 101b, and when the scope connector portion 105a is connected to the pipeline/leakage detection connector 31a, bases 56a to 58a of the scope connector portion 105a are joined to the pipeline/leakage detection connector 31a. As shown in FIG. 36, the scope connector portion 105a of the endoscope body 101b is attracted and fixed to the pipeline/leakage detection connector 31a by a magnetic force of the electromagnet unit 56 provided at the pipeline/leakage detection connector 31a.

Moreover, the water-leakage detection base 119 of the scope connector portion 105a of the endoscope body 101b is joined to the device-side water-leakage detection base 33 disposed at the pipeline/leakage detection connector 31a. This device-side water-leakage detection base 33 is provided at a position of the pipeline/leakage detection connector 31a corresponding to the water-leakage detection base 119 of the scope connector portion 105a of the endoscope body 11b.

Also, a non-contact power supply sending/receiving unit 455 having a sending/receiving coil 455a, which is power transmission portion, is disposed at one side of the pipeline/leakage detection connector 31a. This sending/receiving coil 455a is disposed at a position corresponding to the sending/receiving coil 451 of the battery unit 450 provided at the operation potion 104 of the endoscope body 101b. At this time, the sending/receiving coil 451 of the endoscope body 101b and the sending/receiving coil 455a of the pipeline/leakage detection connector 31a are opposed to each other with the exterior of each of the endoscope body 101b and the pipeline/leakage detection connector 31a between them. The electric power to the power supply circuit provided at the endoscope-side control circuit 113 is supplied by the battery unit 450, and when the endoscope body 101b is set in the washing/disinfecting tank 4 of the endoscope washing/disinfecting device 1C, that is, when the scope connector portion 105a is connected to the pipeline/leakage detention connector 31a, the sending/receiving coil 455a is electromagnetically induced/coupled to the sending/receiving coil 451. Therefore, the power is supplied on the non-contact manner from the endoscope control unit side to the power supply circuit.

Next, the circuit configuration of the device-side control circuit 53 on the endoscope washing/disinfecting device 1C will be described referring to FIG. 37. FIG. 37 is a block diagram showing the circuit configuration of the endoscope washing/disinfecting device 1C.

As shown in FIG. 37, the device-side control circuit 53 is a CPU substrate, and a sensor control circuit 461, an image processing circuit and scope memory R/W (RECORD/WRITING) circuit 463 are disposed. The scope memory R/W circuit 463 has a memory device. To this device-side control circuit 53, a sending/receiving unit 53a, which is information transmission portion by electrically non-contact sending/receiving various signals to/from the device-side sending/receiving antenna 32, is connected. The device-side sending/receiving antenna 32 is disposed at the washing/disinfecting tank 4, and various information signals of the endoscope body 101b is received from the sending/receiving antenna 115 of the endoscope body 101b. These various information signals are supplied to the sensor control circuit 461 of the device-side control circuit 53 through the sending/receiving unit 54.

To the device-side control circuit 53, the monitor 26 of the washing/disinfecting tank 4 and the scope attachment/detachment control circuit 56a for generating a magnetic force at the electromagnet 56b of the pipeline/leakage detection connector 31a are connected. The monitor 26 displays an endoscopic image captured by the image pickup device 111 of the endoscope body 101b supplied to the image processing circuit 62. The monitor 26 can also display various recognition signals of the endoscope body 101b such as pipeline information from the pipeline sensor 121. The endoscope information, which is various recognition signals from the endoscope body 101b, is recorded in the scope memory R/W circuit 463. The various endoscope information can be called up as appropriate to the monitor 26 by panel operation on the operation panel 25. The various endoscope information of the endoscope body 101b is image information, sensor information, scope individual information and the like, for example.

The device-side control circuit 53 is connected to the power supply device (See FIG. 5) in the first embodiment, receives various signals from the operation panel 25 of the washing/disinfecting tank 4 and supplies driving electric power to various valves and electromagnetic valves, which constitute a driving system on the output side. Moreover, to the device-side control circuit 53, various detection signals from various sensors (pressure sensor, water level sensor, position detection sensor), which are input-side sensors, are supplied, and the driving system is controlled as appropriate based on the information of those detection signals. The sensors (pressure sensor, water level sensor, position detection sensor) are not shown but are provided at the washing/disinfecting tank 4.

The device-side control circuit 53 is also connected to the non-contact power supply sending/receiving unit 455. The non-contact power supply sending/receiving unit 455 supplies electric power from the device-side control circuit 53 to the sending/receiving coil 455a. The sending/receiving coil 455a supplies power to the sending/receiving coil 451 of the electromagnetically induced battery unit 450 in this way.

Next, the non-contact power supply sending/receiving unit 455 of the endoscope washing/disinfecting device 1C and the battery unit 450 of the endoscope body 101b will be described in detail referring to FIG. 38.

As shown in FIG. 38, the non-contact power supply sending/receiving unit 455 has an AC input 456, an Electro Magnetic Interference (EMI) filter, which is a noise filter, a rectification/smoothing circuit 458, a charging control circuit 459, and a device-side magnet 455b incorporated. The charging control circuit 459 is connected to a device-side magnet switch 459a and the sending/receiving coil 455a.

Also, as shown in FIG. 38, the battery unit 450 has a power supply circuit 451A, which is battery power supply control portion provided with a switching control circuit 451a and a charging circuit 451b and a battery-side magnet 450b incorporated. The power supply circuit 451A is connected to the battery-side magnet switch 450a. In the state where the scope connector portion 105a of the endoscope body 101b is set at the pipeline/leakage detection connector 31a of the washing/disinfecting tank 4, the device-side magnet switch 459a is disposed at a position corresponding to the battery-side magnet 450b, and the battery-side magnet switch 450a at a position corresponding to the device-side magnet 455b, respectively.

In the charging control circuit 459 of the non-contact power supply sending/receiving unit 455, the device-side magnet switch 459a is operated by receiving a magnetic force when the battery-side magnet 450b of the battery unit 450 approaches. The charging control circuit 459 which received an ON signal from the device-side magnet switch 459a supplies electric power from the AC input 456 to the sending/receiving coil 455a. The sending/receiving coil 451 of the battery unit 450 and the sending/receiving coil 455a of the non-contact power supply sending/receiving unit 455 are electromagnetically induced/coupled and the electric power supplied to the sending/receiving coil 455a is supplied to the sending/receiving coil 451 in the non-contact manner. The electric power of the sending/receiving coil 451 is supplied to the power supply circuit 451A by electromagnetic induction in this way.

In the switching control circuit 451a of the power supply circuit 451A, the battery-side magnet switch 450a is operated by receiving a magnetic force when the battery-side magnet switch 450a approaches the device-side magnet 455b of the non-contact power supply sending/receiving unit 455. The switching control circuit 451a which received the ON signal from the battery-side magnet switch 450a controls switching between charging operation by accumulated voltage of the battery unit 450 or power feed into the endoscope body 101b.

On the monitor 26, in addition to the endoscopic image and scope individual information, information on washing and disinfection of the endoscope body 101b such as washing/disinfecting remaining time is displayed. On the operation panel 25, other than start switches, various setting switches such as a mode selection switch are disposed.

Next, operation of washing and disinfection of the endoscope body 101b by the endoscope washing/disinfecting system of this embodiment constructed as above will be described.

After an endoscopic inspection is finished, the user removes the universal cord 102 from the endoscope body 101b of the endoscope 100b. This universal cord 102 is disposed of as appropriate. Then a user carries out simplified preliminary washing at bedside where a patient is laid. And the user fully washes the endoscope at a sink. In this way, the fully washed endoscope body 101b is set at the washing/disinfecting tank 4 of the endoscope washing/disinfecting device 1C.

First, the user opens the top cover 3 of the endoscope washing/disinfecting device 1C and sets the endoscope body 101b at the washing/disinfecting tank 4 provided on the upper face of the device body. At the bottom surface of the storing recess portion 4a of the washing/disinfecting tank 4, a holding net, not shown, is extended.

At this time, the user opposes the scope connector portion 105a of the endoscope body 101b to the pipeline/leakage detection connector 31a provided on the wall surface of the washing/disinfecting tank 4. The pipeline/leakage detection connector 31a basically has the same structure as the cord-side connector portion 102a of the universal cord 102 so that they can be joined to each other.

And the user sets the endoscope body 101*b* in the washing/disinfecting tank 4 as predetermined, sets the various programs for washing/disinfecting the endoscope body 101*b* on the operation panel and turns on the power switch. Then, the device-side control circuit 53 incorporated in the device body 2 is powered on, and the endoscope washing/disinfecting device 1C starts washing/disinfecting of the endoscope body 101*b*.

Next, various processes of the endoscope washing/disinfecting device 1C will be described using flowcharts in FIGS. 39 to 41.

At Step S61 shown in FIG. 39, input of the start switch is waited for, and when the start switch is turned on, the routine goes to Step S62.

At Step S62, the electromagnet 56*b* provided at the pipeline/leakage detection connector 31*a* is electrified and the electromagnet 56*b* is excited. That is, the scope connector portion 105*a* of the endoscope body 101*b* is attracted and connected by a magnetic force generated at the electromagnet 56*b* to the pipeline/leakage detection connector 31*a*. And each of the pipeline bases 106*a* to 109*a* provided at the scope connector portion 105*a* is automatically joined to each of the bases 36*a* to 39*a* provided at the pipeline/leakage connector 31*a*.

Therefore, in this embodiment, when the user sets the endoscope body 101*b* at the washing/disinfecting tank 4, there is no need to connect the pipelines 106 to 109 of the endoscope body to the washing/disinfecting pipelines on the endoscope washing/disinfecting device 1C side using a tube or the like. Thus, time required for connection of a tube or the like can be drastically reduced, wrong connection or defective connection of the tube will not occur but the pipelines 106 to 109 of the endoscope body 101*b* and the washing/disinfecting pipelines on the endoscope washing/disinfecting device 1C can be surely connected to each other.

At step S62, charging to the battery unit 450 provided at the endoscope body 10*b* is started. Electric power from the non-contact power supply sending/receiving unit 455 of the washing/disinfecting tank 4 to the battery unit 450 of the endoscope body 101*b* is supplied in the non-contact manner. That is, electric power is supplied by electromagnetic induction from the sending/receiving coil 455*a* of the non-contact power supply sending/receiving unit 455 to the sending/receiving coil 451 of the battery unit 450. In detail, with the charging control circuit 459 of the non-contact power supply sending/receiving unit 455, the device-side magnet switch 459*a* is operated by receiving a magnetic force when the battery-side magnet 450*b* of the battery unit 450 approaches. The sending/receiving coil 451 of the battery unit 450 and the sending/receiving coil 455*a* of the non-contact power supply sending/receiving unit 455 are electromagnetically induced/coupled and the electric power supplied to the sending/receiving coil 455*a* is supplied to the sending/receiving coil 451 in the non-contact manner. And the power of the sending/receiving coil 451 is supplied by electromagnetic induction to the power supply circuit 451A. At this time, in the switching control circuit 451*a* of the power supply circuit 451A, the battery-side magnet switch 450*a* is operated by receiving a magnetic force when the battery-side magnet switch 450*a* approaches the device-side magnet 455*b* of the non-contact power supply sending/receiving unit 455. The switching control circuit 451*a* controls switching between charging operation by accumulated voltage of the battery unit 450 or power feed into the endoscope body 101*b*. This charging operation is continued till the switching control circuit 451*a* determines that a predetermined accumulated voltage value is maintained.

Therefore, since the incorporated battery unit 450 is charged during washing/disinfection of the endoscope body 101*b*, the user does not have to carry out works for charging. Thus, time required for charging of the battery unit 450 can be reduced.

Next, the program goes on to Step S64, and power supply of a predetermined frequency of the endoscope body 101*b* is made valid by the switching control circuit 451*a* of the battery unit 450. Then, the endoscope-side control circuit 113 and the device-side control circuit 53 incorporated in the device body 2 are made capable of mutual wireless communication by the sending/receiving antenna 116 of the endoscope body 101*b* and the device-side sending/receiving antenna 32 provided at the washing/disinfecting tank 4.

Then, the program goes on to Step S65, and scope individual information including the model number of the endoscope body 101*b* and various history information such as repair history, washing number of times and the like stored in the memory device of the endoscope-side control circuit 113 are read out by wireless communication through the sending/receiving antenna 116 and the device-side sending/receiving antenna 32 and stored in the scope memory R/W circuit 463 through the device-side control circuit 53 provided at the device body 2.

After that, the program goes on to step S66, and tap water filtered at the water filter 14 is supplied from the water feed/circulation nozzle 24 to the washing/disinfecting tank 4. At Step S67, the water level of the washing/disinfecting tank 4 is detected by a water level sensor or the like, not shown, and finishing timing of the water feed is monitored. When the water level reserved in the washing/disinfecting tank 4 reaches the set water level, the water feed is finished, and the program goes on to Step S68.

At Step S68, various functional checks of the endoscope body 101*b* are carried out. Functional check items include basic items and model-specific items. The basic items are uniformly executed regardless of the model of the endoscope body 101*b* to be washed/disinfected, while the model-specific items are automatically set in correspondence to each endoscope 100*b* based on the read-out model number. The basic items include water leakage check, pipeline clogging check and the like.

For the water leakage check, first, the block valve 47 incorporated in the device body 2 is opened, and air from the water-leakage detection pump 46 is supplied into the endoscope body 101*b* from the water-leakage detection base 119 provided at the scope connector portion 105*a* of the endoscope body 101*b* connected to the device-side water-leakage detection base 33 shown in FIG. 36 so as to pressurize inside the endoscope body 101*b*. When a predetermined pressure is reached, the block valve 47 is closed, and pressure change inside the endoscope body 101*b* is measured. If the pressure change at this time is large, it is determined that a hole is opened on the outer surface of the endoscope body 101*b* and air is leaking. Alternately, if the pressure change is small, it is determined as normal. For the pipeline clogging check, first, the channel block 42 is operated and the circulation port 21 opened at the washing/disinfecting tank 4 is made to communicate with the pipeline/leakage detection connector 31*a*, and then, by driving the channel pump 43, the tap water reserved in the washing/disinfecting tank 4 is supplied to the pipeline/leakage detection connector 31*a*. And the tap water is supplied to each of the pipelines 106 to 109 of the endoscope body 101*b* through the pipeline/leakage detection connector 31*a* and the tap water is circulated. And the flow rate of the tap water flowing through each of the pipelines 106 to 109 at this time is measured by the pipeline sensor 121, the value and the reference value are compared and when the flow rate is less than the reference value, it is determined as the pipeline clogging. On the other hand, if the flow rate is at the reference or above, it is determined as normal.

On the other hand, the model-specific items are different among models, and as in this embodiment, for example, an apparatus provided with the illuminating device 112 at the tip end of the endoscope body 101b as the illuminating portion outputs an illumination driving signal from the endoscope-side control circuit 113 to the illuminating device 112, and the endoscopic image at that time is displayed on the monitor 26. The user checks if the illuminating device 112 is lighted or not from the brightness of the endoscopic image. In this case, lighting of the light emitting device may be automatically detected by comparing a light amount received by the image pickup device 111 with the reference value, for example, though it depends on man-made determination.

In the endoscope body 101b in which the tip end portion of the endoscope insertion portion 105 is curved-operated by the angle member 105B made by EPAM, an angle operation signal is outputted from the endoscope-side control circuit 113 to the angle member 105B, and the endoscopic image at that time is displayed on the monitor 26. The user checks if the operation is normal or not based on the fact that the endoscopic image is moving or not. In this case, too, continuous movement of an image in a specific pixel area of the endoscopic image captured by the image pickup device 111 is detected, this movement is compared with a driving signal outputted to the angle member 105B, and if they substantially correspond to each other, it is determined the angle member 105B is normal, though it depends on the man-made determination.

Moreover, charging voltage information from the power supply circuit 451A of the battery unit 450 incorporated in the endoscope body 101b is discriminated at the device-side control circuit 53 to check if battery charging has been completed or not.

Then, the routine goes on to Step S69, and if any one of the functional check results is determined as abnormal, the routine branches to Step S70, where the abnormality is notified by displaying that the endoscope body 101b is abnormal on the monitor 26 or the like and then, the routine goes on to Step S71, where the washing/disinfecting process of the endoscope washing/disinfecting device 1C is stopped and the routine is finished. In this case, the user can easily determine that abnormality occurs at the endoscope body 101b and report the situation of the abnormality to the manufacturer for request of repair.

On the other hand, when all the functional check items are determined as normal, the routine goes on to Step S72 shown in FIG. 40, and the washing process is started. In this embodiment, the top cover 3 is closed for automatic operation.

When the washing process is started, first, the liquid detergent reserved in the detergent tank 11 is discharged in an appropriate amount from the detergent nozzle 22 by driving of the detergent pump 27 and is mixed in tap water reserved in the washing/disinfecting tank 4 to generate washing water. In the washing process, the washing water reserved in the washing/disinfecting tank 4 is ejected from the high-pressure nozzle 19 at a high pressure provided on the outer circumferential wall surface and the inner circumferential wall surface of the storing recess portion 4a accommodating the endoscope body 101b to generate a water flow in the washing/disinfecting tank 4. And moreover, this water flow is vibrated by driving of the ultrasonic vibrator 49. As a result, the outer surface of the endoscope body 101b is washed by the water flow of the washing water and vibration.

Also, the three-way switching valve 29 and the channel block 42 are operated so that the circulation port 21 and the water-feed/circulation nozzle 24 and the pipeline/leakage detection connector 31a are made to communicate. As a result, by driving of the liquid pump 30 from the water-feed/circulation nozzle 24, the washing water is discharged and circulated. At the same time, the washing water is supplied by the discharge pressure of the channel pump 43 to each of the pipelines 106 to 109 of the endoscope body 101b via the pipeline/leakage detection connector 31a and each of the pipelines 106 to 109 is washed.

At each of the pipelines 106 to 109 of the endoscope body 101b employed in this embodiment, a valve or a mechanism for operating it is not incorporated and the pipelines are piped substantially in the straight state. As a result, the washing water can flow smoothly with little channel resistance and the inside of each of the pipelines 106 to 109 is washed thoroughly.

After that, the routine goes on to Step S73, where it is determined if the washing process is finished or not based on the fact if the washing time has reached a set time or not, and the washing process is continued till the set time is reached. And when the set time is reached, it is determined that the washing is finished, the routine goes on to Step S74, where the washing water is discharged. The discharge of the washing water is forced by operating the switching valve 52 provided at the discharge port 20 opened at the bottom portion of the washing/disinfecting tank 4 so as to make the discharge port 20 and the external discharge port 82 communicate with each other and by driving the discharge pump 34.

When the water discharge is finished as predetermined, the switching valve 52 is operated to block the discharge port 20, and moreover, the three-way switching valve 29 is operated to shut off the circulation port 21 and the water-feed/circulation nozzle 24, and the routine goes on to Step S15, where the disinfecting process is started.

When the disinfecting process is started, first, the disinfectant reserved in the disinfectant tank 12 is fed to the disinfectant nozzle 23 by driving the drug pump 28, and the disinfectant is supplied to the washing/disinfecting tank 4 from this disinfectant nozzle 23. In this state, since the circulation port 21 communicates with the pipeline/leakage detection connector 31a, the disinfectant reserved in the washing/disinfecting tank 4 is poured into each of the pipelines 106 to 109 of the endoscope body 101b by driving of the channel pump 43. And when the level of the disinfectant supplied to the washing/disinfecting tank 4 reaches the set level, the disinfectant is circulated for a set time.

After that, when the set time is reached, the driving of the channel pump 43 is stopped, the endoscope body 101b is soaked in the disinfectant for a set time. In this case, too, since each of the pipelines 106 to 109 of the endoscope body 101b of this embodiment is piped substantially in the straight state, the disinfectant can prevail through each of the pipelines thoroughly.

Then, a soaking time of the endoscope body 101b is measured at Step S76, and when the soaking time reaches the set time, it is determined that disinfection is finished, and the routine goes on to Step S77. At Step S77, the disinfectant is recovered. Since the disinfectant is used repeatedly several times, the switching valve 52 is operated to make the discharge port 20 communicate with the disinfectant tank 12, and the disinfectant reserved in the washing/disinfecting tank 4 is recovered into the disinfectant tank 12.

After the disinfectant is recovered in the disinfectant tank 12 as predetermined, the routine goes on to Step S78, and the rinsing process is started. When the rinsing process is started, first, the three-way switching valve 29 is driven, the water-feed/circulation nozzle 24 is made to communicate with the water filter 14 side, and the tap water filtered by the water filter 14 is supplied from the water-feed/circulation nozzle 24 to the washing/disinfecting tank 4. And after the set level is reached, the three-way switching valve 29 is closed, and as with the washing process, the tap water reserved in the washing/disinfecting tank 4 is circulated. And after the set time has elapsed, the water is discharged.

At Step S79, the number of rinsing times N is counted, and when the number of rinsing times N reaches the set number of times, it is determined that the rinsing is finished. And after the tap water used in the last rinsing process is discharged as predetermined, the routine goes on to Step S80, and an air supply process is started. When the air supply process is started, the channel block 42 is operated, the compressor 44 is made to communicate with the pipeline/leakage detection connector 31a, compressed air is supplied to each of the pipelines 106 to 109 of the endoscope body 101b, and the water in each of the pipelines 106 to 109 is removed and dried.

At step S81, air supply time by the compressor 44 is measured, and when a set time is reached, it is determined that the air supply process is finished, and after the compressor 44 is stopped, the routine goes on to Step S82.

At Step S82, an alcohol flushing process is started. In the alcohol flushing process, first, the channel block 42 is driven, the alcohol tank 13 is made to communicate with the pipeline/leakage detection connector 31a, and only a small amount of alcohol reserved in the alcohol tank 13 is fed to each of the pipelines 106 to 109 of the endoscope body 101b by driving of the alcohol pump 35. Then, the channel block, 42 is driven again, the pipeline/leakage detection connector 31a is made to communicate with the compressor 44, and compressed air is supplied to each of the pipelines 106 to 109 of the endoscope body 101b by driving of the compressor 44.

And alcohol is supplied together with the compressed air to each of the pipelines 106 to 109 of the endoscope body 101b to accelerate evaporation of slight moisture remaining in each of the pipelines 106 to 109 and dry them early.

At Step S83, the compressed air supply time is measured, and when the set time is reached, it is determined that the alcohol flushing process is finished, and all the processes are finished.

In this way, in this embodiment, when washing/disinfecting the used endoscope body 101b, the scope connector portion 105a formed in the endoscope body 101b is attached by one touch to the pipeline/leakage detection connector 31a of the device body 2, the connection can be completed. Thus, complicated connection work is not needed any more, and work efficiency can be improved. Also, by improving the work efficiency, time required for washing/disinfection is reduced, and operating efficiency of the endoscope 100b can be improved by that amount. Moreover, since the endoscope body 101b and the device body 2 are all in the non-contact manner except the portions where each of the pipelines 106 to 109 and the water-leakage detection base 119 are connected, liquid such as the washing water, the disinfectant and the like does not intrude into the endoscope body 101b during washing/disinfection, by which favorable waterproof can be obtained.

In various functional checks executed at Step S68 before the washing/disinfecting process of the endoscope body 101b by the endoscope washing/disinfecting device 1C shown in FIG. 39, in addition to the basic items, model-specific items are also checked, but the model-specific items may be checked in the background in a series of processes from the washing process to the disinfecting process.

Next, an example of the various functional check processes of the endoscope body 101b executed in the background is shown in FIG. 41.

In this routine, first, at Step S91, angle operation of the tip end portion operated by the angle member 105B is checked. As angle operation check, an angle operation signal is outputted from the endoscope-side control circuit 113 to the angle member 105B, and normal operation is checked by movement of the endoscopic image displayed on the monitor 26.

At Step S92, the block valve 47 incorporated in the device body 2 is opened, and air from the water-leakage detection pump 46 is supplied into the endoscope body 101b from the water-leakage detection base 119 provided at the body-side scope connector portion 105a of the endoscope body 101b connected to the base 40 through the water-leakage detection tube 41b and the base 40, and the inside of the endoscope body 101b is pressurized to check the water leakage in the endoscope body 101b.

At Step S93, a lighting signal is outputted from the endoscope-side control circuit 113 to the illuminating device 112, and the endoscopic image at that time is displayed on the monitor 26. The user checks if predetermined brightness is obtained on the monitor 26. At Step S94, by checking the endoscopic image displayed on the monitor 26, the user checks if the image pickup device 111 is normally operating or not.

Moreover, at Step S95, an information signal of the charged voltage value of the battery unit 450 incorporated in the endoscope body 101b is outputted from the power supply circuit 451A, a predetermined charged voltage value is discriminated by the device-side control circuit 53, and if the battery charging has been completed or not is checked. If the predetermined battery charged voltage value is detected, the routine goes on to Step S96.

Here, if the predetermined charged voltage value of the battery unit 450 in the endoscope body 101b is not detected, charging operation to the battery unit 450 is continued till the predetermined charged voltage value is detected. When the predetermined battery charged voltage value is detected by the device-side control circuit 53, the routine goes on to Step S96.

And at Step S96, if it is determined that all the operations are normal, the various functional checks are finished. On the other hand, if even one abnormality is detected, the routine branches to step S97, where abnormality is notified and then, the routine goes on to step. S98, and input is awaited to determine if the current process should be stopped or not. If the process is not stopped, the various functional checks are finished. On the other hand, if the process is to be stopped, the routine goes on to Step S99, where the current process is stopped and the various functional checks are finished.

In this way, the model-specific items of the endoscope body 101b are checked in the background of the process of the endoscope washing/disinfecting device 1C, and check can be made if the battery unit 450 of the endoscope body 101b is charged or not, and battery charging operation can be carried out during each process. Therefore, the battery charging work for the single endoscope body 101b is not necessary. As a result, time required for the washing/disinfecting of the endoscope body 101b can be further reduced, and operating efficiency of the endoscope 100b can be relatively improved.

Seventh Embodiment

In this embodiment an endoscope washing/disinfecting system corresponding to an endoscope 100c with a construction different from that of the endoscope 100b of the sixth embodiment and a seventh embodiment of the present invention will be described based on the attached drawings. The same constructions, actions, and effects as those of the endoscope washing/disinfecting device and the endoscope described in the first to the sixth embodiments are given the same reference numerals and the description will be omitted, while only the different constructions, actions, and effects will be mainly described.

Figure 42:
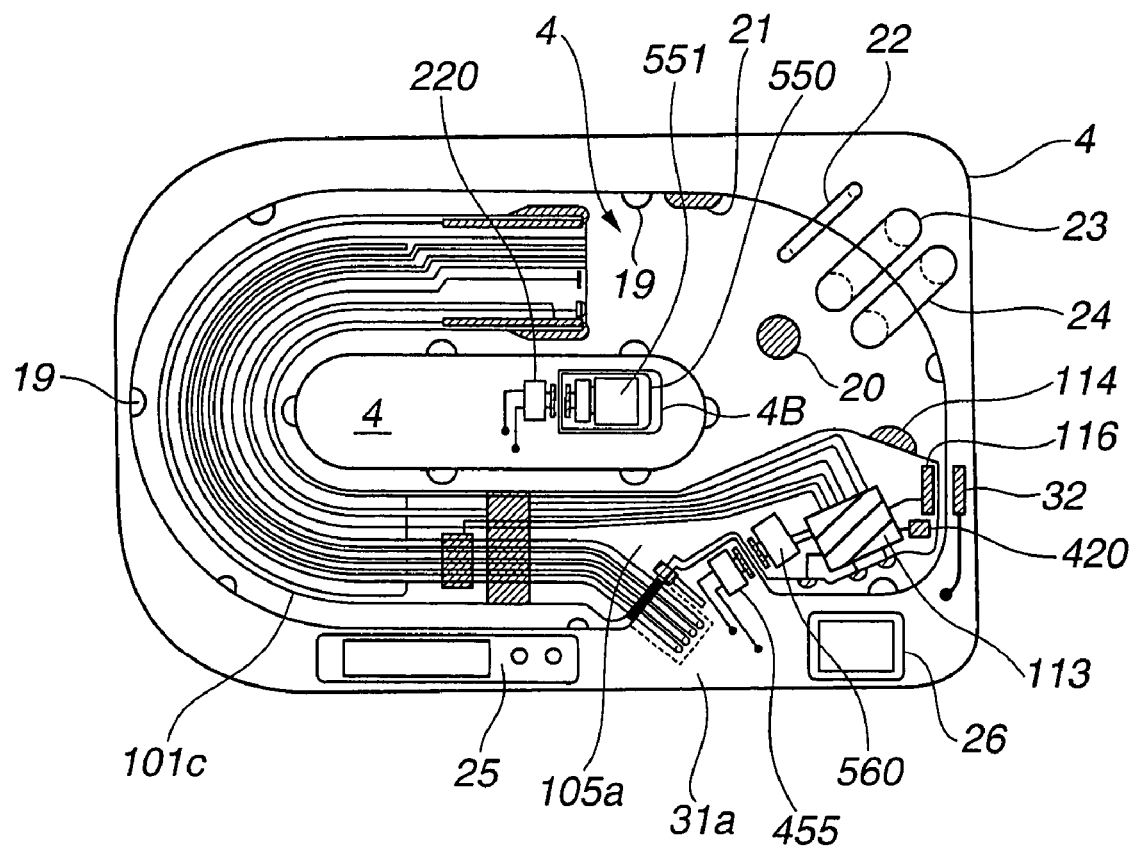
FIG. 42 is a view showing a state where the endoscope is set on the washing/disinfecting tank of the endoscope washing/disinfecting device according to a seventh embodiment.
Figure 43:
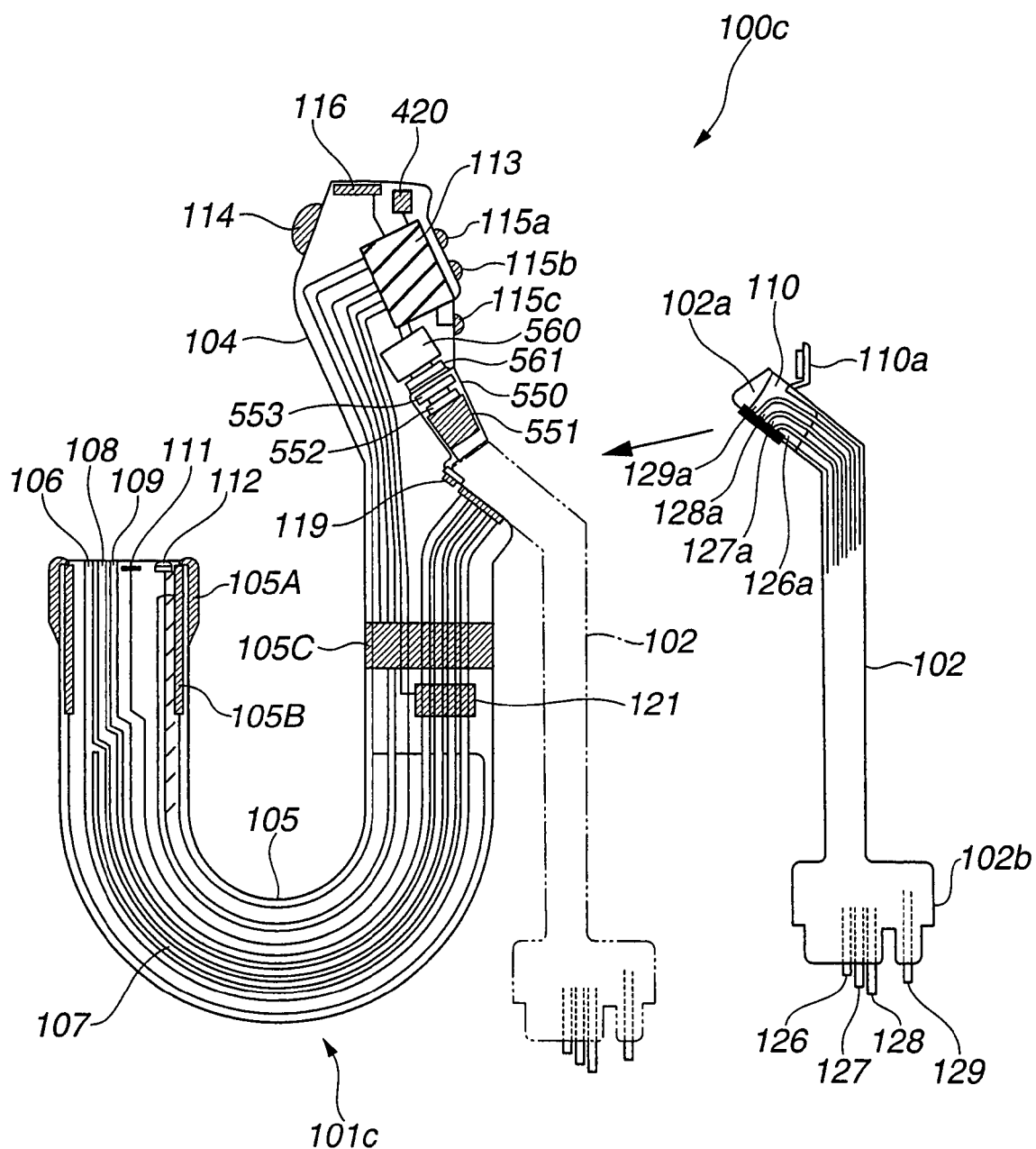
FIG. 43 is a view for explaining a construction of the endoscope according to the seventh embodiment.
Figure 44:
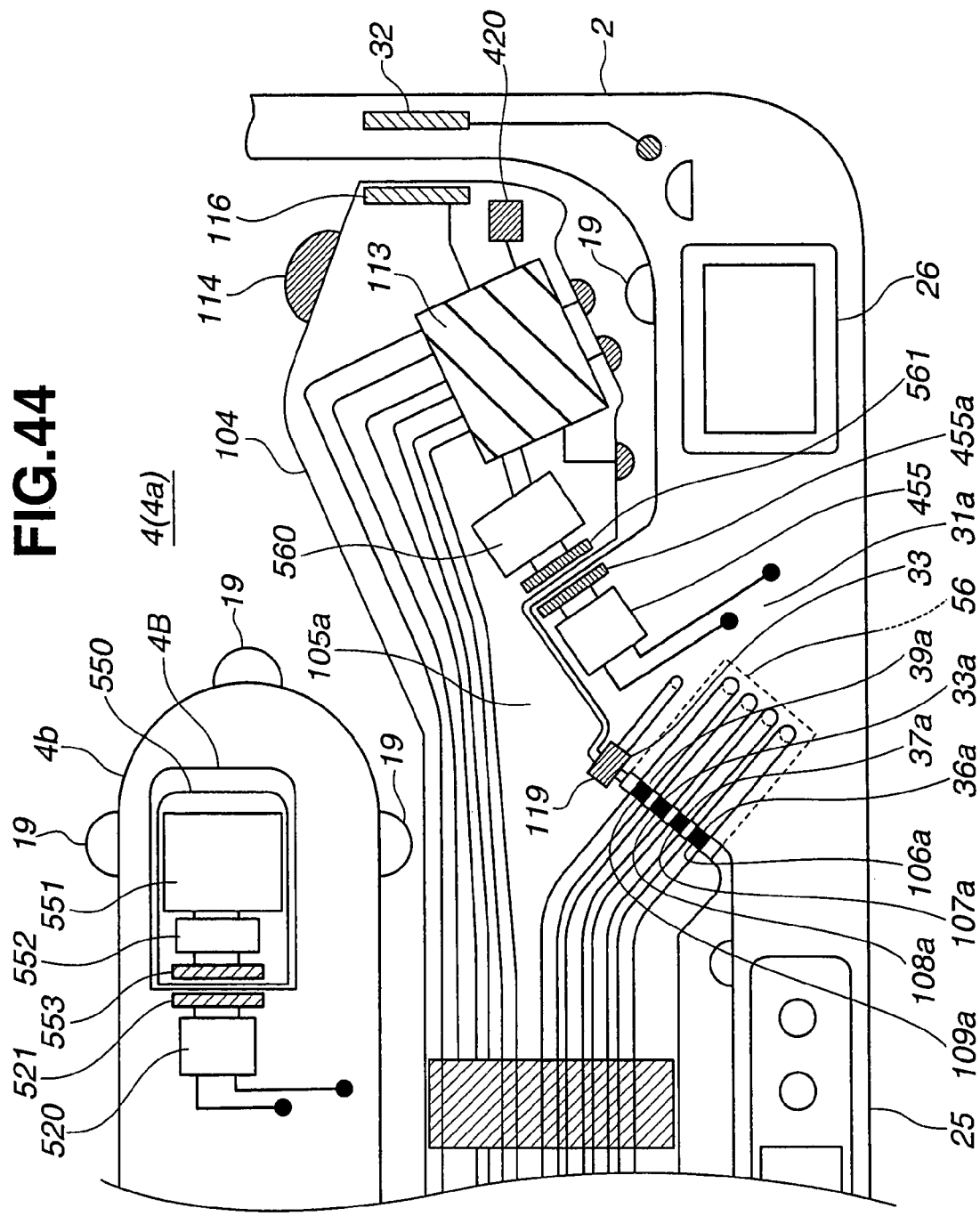
FIG. 44 is an enlarged view for explaining each connector portion of the washing/disinfecting tank and the endoscope according to the seventh embodiment.
Figure 45:
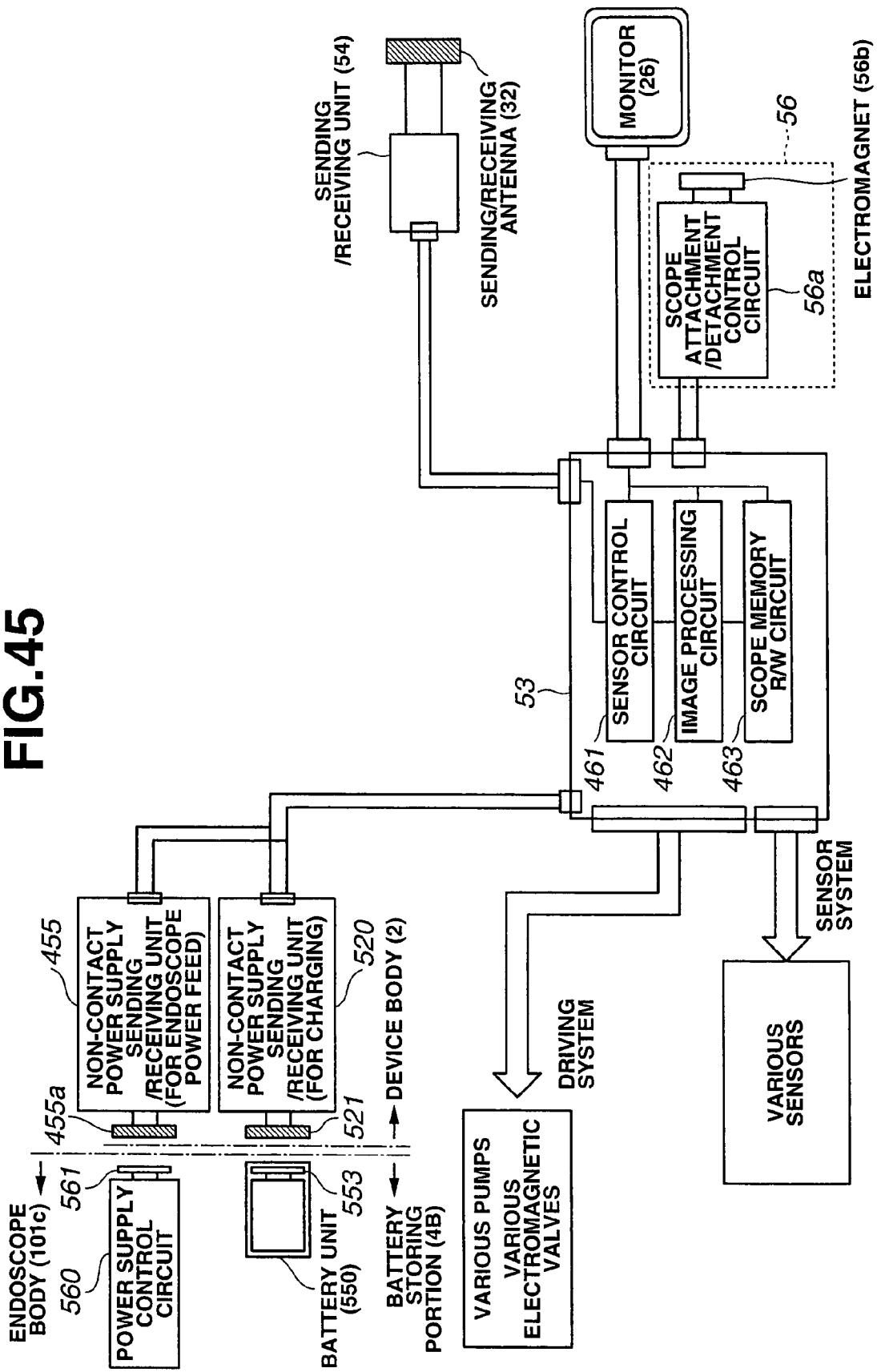
FIG. 45 is a block diagram showing a construction of the device-side control circuit in the device body according to the seventh embodiment.
Figure 46:
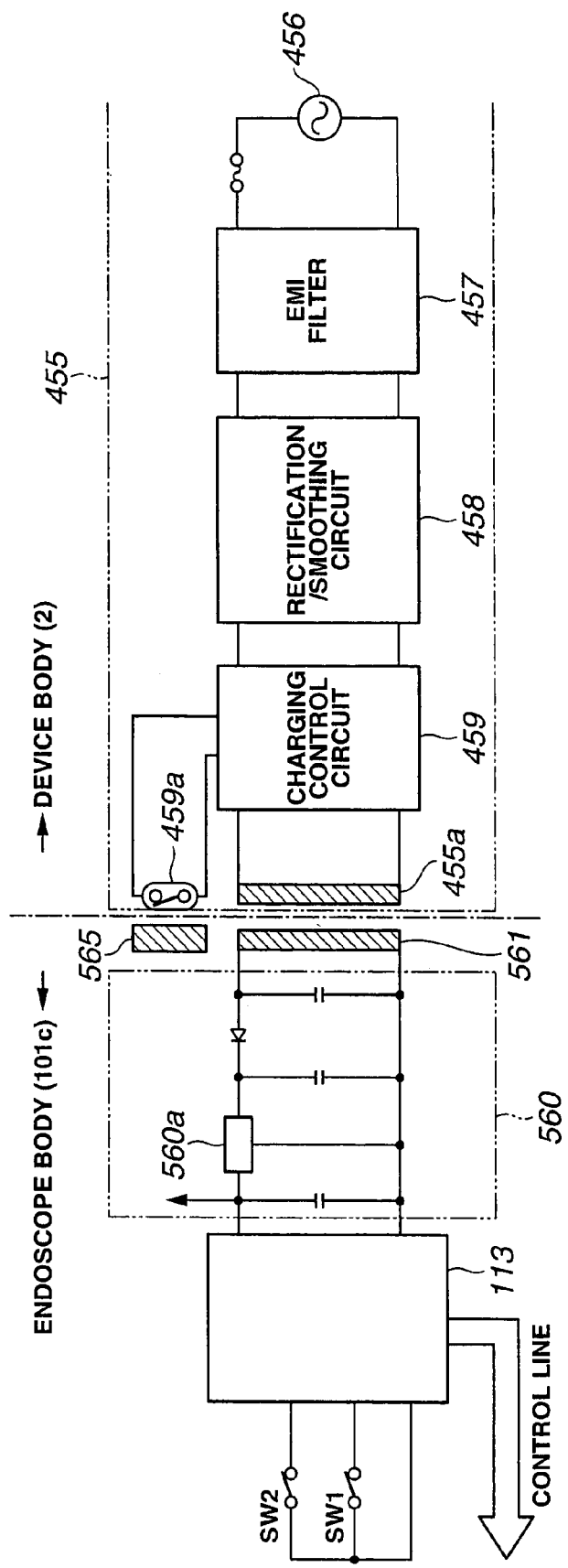
FIG. 46 is a block diagram showing a circuit construction of a scope-side power supply control circuit and a non-contact power supply sending/receiving unit according to the seventh embodiment.
Figure 47:
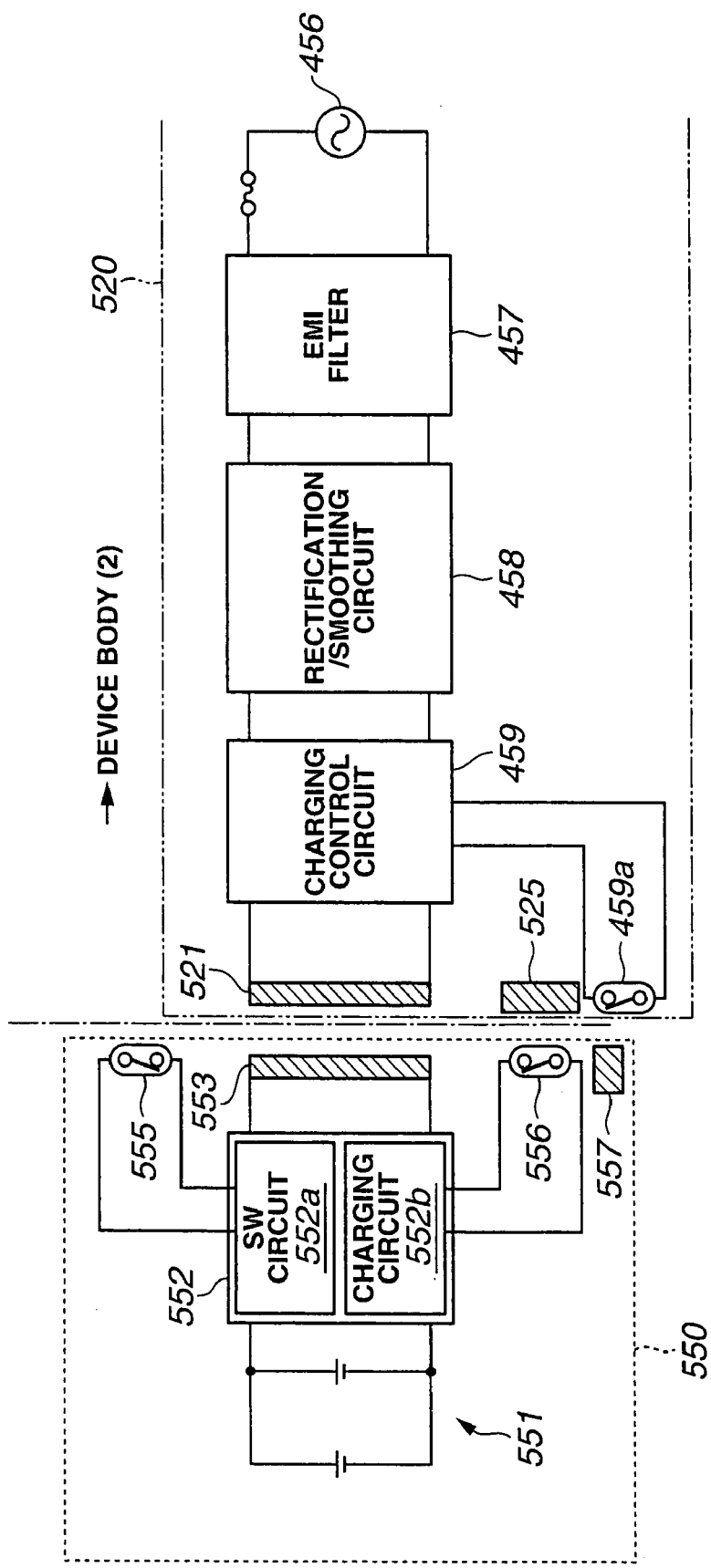
FIG. 47 is a block diagram showing a circuit construction of the battery unit and the non-contact power supply sending/receiving unit according to the seventh embodiment.

FIG. 42 is a view in which an endoscope is set at the washing/disinfecting tank of an endoscope washing/disinfecting device according to this embodiment, FIG. 43 is a view for explaining a construction of the endoscope, FIG. 44 is an enlarged view for explaining the washing/disinfecting tank and each connector portion of the endoscope, FIG. 45 is a block diagram showing a construction of a device-side control circuit in the device body, FIG. 46 is a block diagram showing a circuit configuration of a scope-side power supply control circuit and a non-contact power supply sending/receiving unit, and FIG. 47 is a block diagram showing a circuit configuration of a battery unit and the non-contact power supply sending/receiving unit.

As shown in FIG. 42, the endoscope body 101c is set at the washing/disinfecting tank 4 of the endoscope washing/disinfecting device 1C as in the sixth embodiment.

To the pipeline/leakage detection connector 31a of the washing/disinfecting tank 4, the non-contact power supply sending/receiving unit 455 having the sending/receiving coil 455a, which is power transmission portion, is disposed. This non-contact power supply sending/receiving unit 455 supplies electric power to the endoscope body 101c in the non-contact manner.

Also, in the storing projecting portion 4b at the center region of the washing/disinfecting tank 4, a battery storing portion 4B in which a battery unit 550, which is battery power supply portion, can be detachably attached to the endoscope body 101c, which will be described later, is provided. In this battery storing portion 4B, an electromagnet unit, not shown, is disposed, and the electromagnet is excited to attract and fix the battery unit 550 as predetermined. A non-contact power supply sending/receiving unit 520 is also disposed in this battery storing portion 4B so as to supply electric power for charging the battery unit 550 in the non-contact electromagnetic induction.

First, the construction of the endoscope 100c will be described based on FIG. 43. Since the endoscope 100c in this embodiment has the same construction as that of the endoscope 100b of the sixth embodiment other than the construction described below, the description will be omitted.

In the endoscope 100c, as in the sixth embodiment, the endoscope body 101c and the universal cord 102 can be separated from each other. Moreover, the endoscope body 101c has the detachable battery unit 550. This battery unit 550 has a sending/receiving coil 553, which is power transmission portion, a battery-side power supply control circuit 552, and a battery 551. That is, the battery unit 550 is battery power supply portion in the endoscope body 10c.

In the operation portion 104 of the endoscope body 101c, a scope-side power supply control circuit 560 for supplying power to the endoscope-side control circuit 113 is incorporated. This scope-side power supply control circuit 560 is connected to a sending/receiving coil 561, and electric power is supplied from the sending/receiving coil 553 of the battery unit 550 by non-contact electromagnetic induction. The power supply control circuit 560 rectifies power from the battery unit 550 as predetermined and supplies it to the endoscope-side control circuit 113.

Next, joining of the scope connector portion 105a of the endoscope body 101c and the pipeline/leakage detection connector 31a, and the battery unit 550 and the battery storing portion 4B of the storing projecting portion 4b will be described.

The joining between the scope connector portion 105a of the endoscope body 101c and the pipeline/leakage detection connector 31a shown in FIG. 44 basically has the same construction as that of the cord-side connector portion 102a of the universal cord 102, and they are in the structure capable of mutual joining. At this time, the non-contact power supply sending/receiving unit 455 of the pipeline/leakage detection connector 31a supplies electric power by non-contact electromagnetic induction to the sending/receiving coil 561 of the scope-side power supply control circuit 560 of the scope connector portion 105a from the sending/receiving coil 455a.

The joining between the battery unit 550 removed from the endoscope body 101c and the battery storing portion 4B basically has the same construction as a part of the scope connector portion 105a of the endoscope body 101c and they are in the structure capable of mutual joining. At this time, the non-contact power supply sending/receiving unit 520 of the battery storing portion 4B supplies electric power by non-contact electromagnetic induction to the sending/receiving coil 553 of the battery-side power supply control circuit 552 of the battery unit 550 from the sending/receiving coil 521. In detail, as shown in FIG. 45, the device-side control circuit 53 is connected to the non-contact power supply sending/receiving unit 455 having the sending/receiving coil 455a for power feed of the endoscope body 101c and the non-contact power supply sending/receiving unit 520 having the sending/receiving coil 521 for charging the battery unit 550. Therefore, the sending/receiving coil 561 of the scope-side power supply control circuit 560 of the endoscope body 101c is supplied with electric power from the device-side control circuit 53 by the sending/receiving coil 455a in the non-contact manner. Also, the sending/receiving coil 553 of the battery unit 550 of the battery storing portion 4B is supplied with power from the device-side control circuit 53 by the sending/receiving coil 521 in the non-contact manner.

Next, power feed to the endoscope body 101c and charging operation to the battery unit 550 will be described in detail referring to FIGS. 46 and 47.

First, power supply to the endoscope body 101c will be described using FIG. 46.

As shown in FIG. 46, the scope-side power supply control circuit 560 comprises electronic parts such as a power supply control IC 560a and connected to the sending/receiving coil 561. The scope-side magnet 565 is disposed at a position of the endoscope body 101c to which the device-side magnet switch 459a corresponds. The charging control circuit 459 of the non-contact power supply sending/receiving unit 455 receives an ON signal operated by the device-side magnet switch 459a having received a magnetic force caused by approach of the scope-side magnet 565 and supplies electric power to the sending/receiving coil 455a. The power supplied to the sending/receiving coil 455a is supplied to the sending/receiving coil 561 by non-contact electromagnetic induction to the sending/receiving coil 561 of the scope-side power supply control circuit 560.

And the power fed to the sending/receiving coil 561 is rectified to a predetermined power voltage by the scope-side power supply control circuit 560 and supplied to the endoscope-side control circuit 113. The endoscope-side control circuit 113 supplies driving signals to various driving equipment of the endoscope body 101c through control lines. The endoscope-side control circuit 113 has various switches SW1, SW2 and the like disposed.

Next, the battery unit 550 will be described using FIG. 47 for charging when it is installed at the battery storing portion 4B.

As shown in FIG. 47, the battery unit 550 comprises a battery-side magnet 557, a magnet switch 556 for charging, the sending/receiving coil 553, a magnet switch 555 for power feed, the battery-side power supply control circuit 552, and various electronic parts constituting the battery 551. The battery-side magnet 557 is disposed at a position corresponding to the device-side magnet switch 459a and the charging magnet switch 556 to the device-side magnet 525 of the non-contact power supply sending/receiving unit 520.

The magnet switch 555 for power feed is a switch disposed at a position corresponding to the scope-side magnet 565 shown in FIG. 46 when the battery unit 550 is joined to the endoscope body 101c and operated by receiving a magnetic force caused by approach of the scope-side magnet 565. By operation of the power feed magnet switch 555, the battery unit 550 feeds power to the endoscope body 101c, and power is supplied to various equipment of the endoscope body 101c.

The battery-side power supply control circuit 552 has a SW (switch) circuit 552a and a charging circuit 552b and is connected to the power feed magnet switch 555 and the charging magnet switch 556.

As for the charging operation to the battery unit 550, the device-side magnet 525 of the non-contact power supply sending/receiving unit 520 is operated upon receipt of a magnetic force by approach to the charging magnet switch 556, and an ON signal is supplied to the charging circuit 552b of the battery-side power supply control circuit 552. And the battery-side power supply control circuit 552 switches the SW circuit 552a so that power is supplied to the battery 551 side. At this time, the device-side magnet switch 459a of the charging control circuit 459 of the non-contact power supply sending/receiving unit 520 receives the magnetic force by approach to the battery-side magnet 557, and electric power is supplied from the charging control circuit 459 to the sending/receiving coil 521 by the ON signal. And the power of the sending/receiving coil 521 is supplied to the sending/receiving coil 553 of the battery unit 550 by electromagnetic induction. Next, the power supplied to the sending/receiving coil 553 charges the battery 551 to a predetermined voltage through the battery-side power supply control circuit 552.

Next, the washing and disinfecting operation of the endoscope body 101c by the endoscope washing/disinfecting system of this embodiment constructed as above is carried out in the same way as the flowchart (FIGS. 39 top 41) described in the sixth embodiment.

At Step S63 shown in FIG. 39, charging of the battery unit 550 provided at the battery storing portion 4B of the washing/disinfecting tank 4 is started, and at Step S64, a power supply at a predetermined frequency of the endoscope body 101c is made valid by the scope-side power supply control circuit 560 of the endoscope body 101c. The battery charging check at Step S94 in FIG. 41 is charging check of the battery unit 550.

The endoscope washing/disinfecting device 1C of this embodiment constructed as above has the effects of the sixth embodiment and can also support the endoscope 100c provided with the detachable battery unit 550. Also, since the battery unit 550 is installed at the battery storing portion 4B of the washing/disinfecting tank 4, it is capable of washing and disinfection as well as the charging operation.

In the sixth and the seventh embodiments, the endoscope washing/disinfecting device 1C may have a function for charging only the battery units 450, 550 and this charging function may be started by operation of the operation panel 25.

The present invention is not limited to the above-mentioned first to the seventh embodiments, but various changes, modifications and the like can be made in a range not departing from the gist of the present invention.

What is claimed is:

1. An endoscope washing/disinfecting device for washing and disinfecting an endoscope set in a washing tank, the endoscope washing/disinfecting device comprising:
a connection pipe to which at least a washing liquid is supplied;
a moving mechanism for moving the connection pipe in a direction of a channel port of the endoscope set in the washing tank; and
a seal member for sealing a space between the connection pipe and the channel port;
a bulkhead provided outside of a side wall of the washing tank and forming a sealed space in which the moving mechanism and a part of the connection pipe are provided, the sealed space being formed as a result of connection of the channel and the connection pipe and different from a flowing passage through which the washing liquid is flown;
a water leakage sensor provided in the bulkhead; and
a control circuit for driving and controlling the moving mechanism according to a washing/disinfecting program for the endoscope, the control circuit monitoring an input of signal from the water leakage sensor all the time during execution of the washing/disinfecting program and executing error processing when receiving a signal indicating water leakage.

2. The endoscope washing/disinfecting device according to claim 1, further comprising a pressurizing portion for pressurizing inside of the bulkhead when liquid is in the washing tank.

3. The endoscope washing/disinfecting device according to claim 1, wherein the seal member configured to expand or contract in a radial direction crossing an axial direction of the connection pipe to controllably seal the space between the connection pipe and the channel port without a gap or with a gap.

4. The endoscope washing/disinfecting device according to claim 3, wherein the seal member is comprised of an artificial muscle member.

5. The endoscope washing/disinfecting device according to claim 1, wherein the moving mechanism is comprised of an artificial muscle member.

* * * * *